US008598179B2

(12) United States Patent
Nazaré et al.

(10) Patent No.: US 8,598,179 B2
(45) Date of Patent: Dec. 3, 2013

(54) PYRAZOLE-CARBOXAMIDE DERIVATIVES AS P2Y12 ANTAGONISTS

(75) Inventors: Marc Nazaré, Frankfurt am Main (DE); Gernot Zech, Frankfurt am Main (DE); Jochen Goerlitzer, Frankfurt am Main (DE); Melitta Just, Langen (DE); Tilo Weiss, Frankfurt am Main (DE); Gerhard Hessler, Frankfurt am Main (DE); Werngard Czechtizky, Frankfurt am Main (DE); Sven Ruf, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/817,868

(22) Filed: Jun. 17, 2010

(65) Prior Publication Data

US 2011/0039829 A1 Feb. 17, 2011

Related U.S. Application Data

(63) Continuation of application No. PCT/EP2008/010573, filed on Dec. 12, 2008.

(30) Foreign Application Priority Data

Dec. 26, 2007 (EP) .................................. 07291628

(51) Int. Cl.
| | | |
|---|---|---|
| *A61K 31/496* | (2006.01) | |
| *C07D 231/22* | (2006.01) | |
| *C07D 413/12* | (2006.01) | |
| *C07D 417/12* | (2006.01) | |
| *A61K 31/454* | (2006.01) | |
| *A61K 31/506* | (2006.01) | |
| *C07D 401/12* | (2006.01) | |
| *C07D 401/04* | (2006.01) | |

(52) U.S. Cl.
USPC .................. 514/254.02; 514/254.05; 544/369; 544/371; 544/367; 544/319; 546/198; 546/211; 540/575

(58) Field of Classification Search
None
See application file for complete search history.

(56) References Cited

FOREIGN PATENT DOCUMENTS

| EP | 1 473 302 A1 | 11/2004 |
| EP | 1 698 626 A1 | 9/2006 |
| WO | WO 2005/00281 A2 | 1/2005 |
| WO | WO 20051002574 A1 | 1/2005 |
| WO | WO 20061114774 A2 | 11/2006 |
| WO | WO 2007/092681 A2 | 8/2007 |

OTHER PUBLICATIONS

Littke, Adam F. et al., "Palladium-Catalyzed Coupling Reactions of Aryl Chlorides," Angewandte Chemie International Edition (2002), vol. 41, pp. 4176-4211.
Muci, Alex R. et al., "Practical Palladium Catalysts for C-N and C-O Bond Formation," Topics in Current Chemistry (2002), vol. 219, pp. 131-209.
Tunoori, Ashok Rao et al., "Polymer-Bound Triphenylphosphine as Traceless Reagent for Mitsunobu Reactions in Combinatorial Chemistry: Synthesis of Aryl Ethers from Phenols and Alcohols," Tetrahedron Letters (1998), vol. 39, pp. 8751-8754.
Booker-Milburn, Kevin I., "A Convenient Method for the Synthesis of C-5 Substituted 1-Tosyloyrazoles," Synlett (1992), pp. 327-328.
Bravo, Pierfrancesco et al., "An Efficient Entry to Perfluoroalkyl Substituted Azoles Starting from B-Perfluoroalkyl-B-dicarbonyl Compounds," Tetrahedron (1994), vol. 50, No. 29, pp. 8827-8836.
Yang, Bryant H. et al., "Palladium-catalyzed amination of aryl halides and sulfonates," Journal of Organometallic Chemistry (1999), vol. 576, pp. 125-146.
Gachet, Christian et al., "Purinoceptors on blood platelets: further pharmacological and clinical evidence to suggest the presence of two ADP receptors," British Journal of Haematology (1995), vol. 91, pp. 434-444.

(Continued)

*Primary Examiner* — Emily Bernhardt
(74) *Attorney, Agent, or Firm* — Scully, Scott, Murphy & Presser, P.C.

(57) ABSTRACT

The present invention relates to compounds of the formula I,

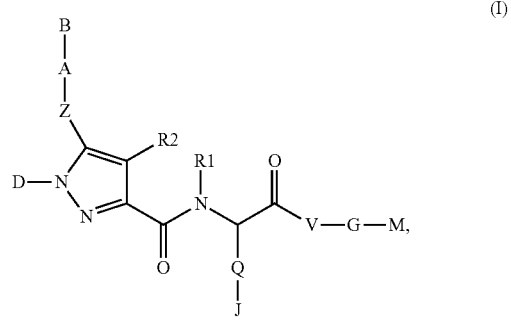

(I)

wherein
R1; R2; Z; A; B; D; Q; J; V; G and M have the meanings indicated in the claims. The compounds of the formula I are valuable pharmacologically active compounds. They exhibit a strong anti-aggregating effect on platelets and thus an anti-thrombotic effect and are suitable, e.g., for the therapy and prophylaxis of cardio-vascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

8 Claims, No Drawings

(56) References Cited

OTHER PUBLICATIONS

Butler, Donald E. et al., "New General Methods for the Substitution of 5-Chloropyrazoles. The Synthesis of 1,3-Dialkyl-5-chloropyrazol-4-yl Aryl Ketones and New 1,3-Dialkyl-2-pyrazolin-5-ones," Journal of Organic Chemistry (1971), vol. 36, No. 17, pp. 2542-2547.

Hughes, D. L. et al., "A Mechanistic Study of the Mitsunobu Esterification Reaction," Journal of the American Chemical Society (1988), vol. 110, pp. 6487-6491.

Mills, David C.B., "ADP Receptors on Platelets," Thrombosis and Haemostasis (1996), vol. 76, pp. 835-856.

Camp Davdea "Mechanism of the Mitsunobu Esterification Reacton 1. The Involvement of Phosphoranes and Oxyphosphonium Salts," Journal of Organic Chemistry (1989), vol. 54, pp. 3045-3049.

Crich, David et al., "Some Observations on the Mechanism of the Mitsunobu Reaction," Journal of Organic Chemistry (1989), vol. 54, pp. 257-259.

Bundgaard, Hans, "Design of prodrugs: Bioreversible derivatives for various functional groups and chemical entities," Elsevier (1985), pp. 1-92.

Nichols, David E. et al., "1-(2,5-Dimethoxy-4-(trifluoromethyl)phenyl)-2-aminopropane: A Potent Serotonin 5-HT2A/2C Agonist," Journal of Medicinal Chemistry (1994), vol. 37, pp. 4346-4351.

Chan, Dominic M.T. et al., "New N- an O-Arylations with Phenylboronic Acids and Cupric Acetate," Tetrahedron Letters (1998), vol. 39, pp. 2933-2936.

Elnagdi, Mohamed Hilmy et al., "Recent Developments in the Synthesis of Pyrazole Derivatives," Heterocycles (1985), vol. 23, No. 12, pp. 3121-3153.

Qing, Feng-Ling et al., "First synthesis of ortho-trifluoromethylated aryl triflates," Jounal of the Chemical Society, Perkin Trans. 1 (1997), pp. 3053-3057.

Fleisher, David et al., "Improved oral drug delivery: solubility limitations overcome by the use of prodrugs," Advanced Drug Delivery Reviews (1996), vol. 19, pp. 115-130.

Foti, Francesco et al., "First Synthesis of a Bromonitrilimine. Direct Formation of 3-Bromopyrazole Derivatives," Tetrahedron Letters (1999), vol. 40, pp. 2605-2606.

Bundgaard, Hans, "Novel chemical approaches in prodrug design," Drugs of the Future (1991), vol. 16, No. 5, pp. 443-458.

Haque, Tasir S. et al., "Parallel Synthesis of Potent, Pyrazole-Based Inhibitors of Helicobacter pylori Dihydroorotate Dehydrogenase," Journal of Medicinal Chemistry (2002), vol. 45, pp. 4669-4678.

Huang, Ying R. et al., "Regioselective Synthesis of 1,3,5-Triaryl-4-alkylpyrazoles: Novel Ligands for the Estrogen Receptor," Organic Letters (2000), vol. 2, No. 18, pp. 2833-2835.

Elguero, Jose, "Pyrazoles," Comprehensive Heterocyclic Chemistry II (1996), vol. 3, pp. 1-75.

Testa, Bernard et al., "Hydrolysis in Drug and Prodrug Metabolism: Chemistry, Biochemistry, and Enzymology," Wiley VCH (2003), pp. 1-9.

Hartwig, John F. "Ubergangsmeall-katalysierte Synthese von Arylaminen und Arylethen aus Arylhalogeniden und-triflaten: Anwendungen und Reaktionsmechanismus," Angewandte Chemie (1998), vol. 110, pp. 2154-2177.

Herbert, J.M. et al., "Inhibitory Effect of Clopidogrel on Platelet Adhesion and Intimal Proliferation After Arterial Injury in Rabbits," Arteriosclerosis and Thrombosis (1993), vol. 13, pp. 1171-1179.

Herbert, J.M. et al., "Clopidogrel, A Novel Antiplatelet and Antithrombotic Agent," Cardiovascular Drug Reviews (1993), vol. 11, No. 2, pp. 180-198.

Maffrand, J.P. et al., "ADP Plays a Key Role in Thrombogenesis in Rats," Thrombosis and Haemostasis (1988), vol. 59, pp. 225-230.

Pelletier, Jeffrey C. et al., "Mitsunobu reaction modifications allowing product isolation without chromatography: application to a small parallel library," Tetrahedron Letters (2000), vol. 41, pp. 797-800.

Jeon, Dong Ju et al., "Synthesis of New 4-Benzoyl-5-hydroxy-3-Trifluoromethylpyrazole Derivatives via [1,3] Rearrangements of Benzoyl Group Using tert—Butylilthium," Synthetic Communications (1998), vol. 28, pp. 2159-2166.

Folts, J.D. et al., "Platelet aggregation in partially obstructed vessels and its elimination with aspirin," Circulation (1976), vol. 54, pp. 365-370.

Wolfe, John P. et al., "Simple, Efficient Catalyst System for the Palladium-Catalyzed Amination of Aryl Chlorides, Bromides, and Triflates," Journal of Organic Chemistry (2000), vol. 65, pp. 1158-1174.

Jones, R.G. et al., "vic-Dicarboxylic Acid Derivatives of Pyrazole, Isoxazole, and Pyrimidine," Journal of Organic Chemistry (1955), vol. 20, pp. 1342-1347.

Makino, Kenzi et al., "Selective Fluorination of Ethyl 1-Methylpyrazole-4-carboxylates with Poly(Hydrogen Fluoride)-Amine Complex under Electrolytic Anodic Oxidation," Journal of Fluorine Chemistry (1988), vol. 39, pp. 435-440.

Huisgen, Rolf et al., "Diazocarbonyl Compounds and 1-Diethylaminopropyne," Journal of the American Chemical Society (1979), vol. 101, pp. 3647-3648.

Kudo, Noriaki et al., "Synthesis and Herbicidal Activity of 1,5-Diarylpyrazole Derivatives," Chemical and Pharmaceutical Bulletin (1999), vol. 47, pp. 857-868.

Ochi, Hisao et al., "Synthesis of 2-Substituted 2,6-Dihydro-3-hydroxy-7H-pyrazolo[4,3-d]pyrimidin-7-ones," Chemical and Pharmaceutical Bulletin (1983), vol. 31, pp. 1228-1234.

Heinisch, Gottfried et al., "Pyridazines, 71. A Novel Type of 1,2-Diazine→1,2-Diazole Ring Contraction," Heterocycles (1994), vol. 38, No. 9, pp. 2081-2089.

Beller, Matthias et al., "Transition Metals for Organic Synthesis," Wiley-VCH (1998), vol. 1, pp. 1-13.

Netherton, Matthew R. et al., "Palladium-Catalyzed Cross-Coupling Reactions of Unactivated Alkyl Electrophiles with Organometallic Compounds," Topics in Organometallic Chemistry (2005), vol. 14, pp. 85-108.

Washizuka, Ken-Ichi et al., "Novel generation of azomethine imines from alpha-silylnitrosamines by 1,4-silatropic shift and their cycloaddition," Tetrahedron Letters (1999), vol. 40, pp. 8849-8853.

Gradner, Derek V. et al., "A Versatile Approach to Analogues of the Cannabinoid-like Anti-emetic Nonabine (BRL 4664)," Jounal of Heterocyclic Chemistry (1984), vol. 21, pp. 121-127.

Takasaki, Jun et al., "Moecular Cloning of the Plaee P2TAC ADP Receptor: Pharmacological Comparison with Another ADP Receptor, the P2Y1 Receptor," Molecular Pharmacology (2001), vol. 60, pp. 432-439.

Sakamoto, Takao et al., "Palladium-catalyzed cyanation of aryl and heteroaryl iodides with copper(I) cyanide," Journal of the Chemical Society Perkin Trans. 1 (1999), pp. 2323-2326.

Umemoto, Teruo et al., "Power and Structure-Variable Fluorinating Agents. The N-Fluoropyridinium Salt System," Journal of the American Chemical Society (1990), vol. 112, pp. 8563-8575.

Urata, Hisao et al., "A Novel and Convenient Method for Trifluoromethylation of Organic Halides Using CF3SiR'3/KF/Cu(I) System," Tetrahedron Letters (1991), vol. 32, pp. 91-94.

Kang, Suk-ku et al., "Copper-catalyzed N-Arylation of Aryl Iodides with Benzamides or Nitrogen Heterocycles in the Presence of Ethylenediamine," Synlett (2002), vol. 3, pp. 427-430.

Klapars, Artis et al., "A General and Efficient Copper Catalyst for the Amidation of Aryl Halides and the N-Arylation of Nitrogen Heterocycles," Journal of the American Chemical Society (2001), vol. 123, pp. 7727-7729.

Sauer, Daryl R. et al., "The Synthesis of 3(5)-[(2-Hydroxyethoxy)methyl]pyrazole-5(3)-carboxamide, an Acyclic Analogue of 4-Deoxypyrazofurin," Journal of Organic Chemistry (1990), vol. 55, pp. 5535-5538.

Kwong, Fuk Yee et al., "Copper-Catalyzed Coupling of Alkylamines and Aryl Iodides: An Efficient System Even in an Air Atmosphere," Organic Letters (2002), vol. 4, No. 4, pp. 581-584.

Rodriguez-Franco, Maria Isabel et al., "A mild and efficient method for the regionselective iodination of pyrazoles," Tetrahedron Letters (2001), vol. 42, pp. 863-865.

(56) References Cited

OTHER PUBLICATIONS

Humphries, R.G. et al., "Pharmacological profile of the novel P2T-purinoceptor antagonist, FPL 67085 in vitro and in the anaesthetized rat in vivo," British Journal of Pharmacology (1995), vol. 115, pp. 1110-1116.
Storer, Richard et al., "The Synthesis and Antiviral Activity of 4-Fluoro-1-B-D-Ribofuranosyl-1H-Pyrazole-3-Carboxamide," Nucleotides & Nucleotides (1999), vol. 18, pp. 203-216.
Su, De-Bao et al., "Methyl Chlorodifluoroacetate a Convenient Trifluoromethylating Agent," Tetrahedron Letters (1991), vol. 32, pp. 7689-7690.
Pilling, Garry M. et al., "The Synthesis of 1H-Pyrazol-4-OLS From 2-(2-Alkylidenehydrazino) Acetic Acids," Tetrahedron Letters (1988), vol. 29, No. 12, pp. 1341-1342.
Pawlas, Jan et al., "Synthesis of 1-Hydroxy-Substituted Pyrazolo[3,4-c]- and Pyrazolo[4,3-c]quinolines and -isoquinolines from 4- and 5-Aryl-Substituted 1-Benzyloxypyrazoles," Journal of Organic Chemistry (2000), vol. 65, pp. 9001-9006.
Lam, Patrick Y.S. et al., "New Aryl/Heteroaryl C-N Bond Cross-coupling Reactions via Arylboronic Acid/Cupric Acetate Arylation," Tetrahedron Letters (1998), vol. 39, pp. 2941-2944.
Andre, Patrick et al., "P2Y12 regulates platelet adhesion/activation, thrombus growth, and thrombus stability in injured arteries," Journal of Clinical Investigation (2003), vol. 112, pp. 398-406.
Patel, Himatkumar V. et al., "Concise and Efficient Synthesis of 1H-Pyrazoles: Reaction of [Hydroxy(tosyloxy)iodo] benzene with Ethyl 2,3-Dioxobutanoate-2-arylhydrazones," Synthetic Communications (1991), vol. 21, pp. 1583-1588.
Nagai, Toshikazu et al., "Recent Progress in the Preparation and Synthetic Uses of the Reactions of 3H-Pyrazoles. A Review," Organic Preparations and Procedures Int. (1993), vol. 25, pp. 403-435.
Mitsunobu, Oyo, "The Use of Diethyl Azodicarboxylate and Triphenylphosphine in Synthesis and Transformation of Natural Products," Synthesis (1981), pp. 1-28.
Martins, Marcros A.P. et al., "1,1,1-Trichioro-4,4-diethoxy-3-buten-2-one and its Trichloroaceylacetate Derivatives: Synthesis and Applications in Regiospecific Preparation of Azoles," Synthesis (2003), No. 15, pp. 2353-2357.
Martins, Marcos A.P. et al., "One-Pot Synthesis of 3(5)-Ethoxycarbonyipyrazoles," Synthesis (1995), vol. 12, pp. 1491-1492.
Mustard, J. Fraser et al., "[1] Isolation of Human Platelets from Plasma by Centrifugation and Washing," Methods in Enzymology (1989), vol. 169, pp. 3-11.
XP002485258, Chemical Abstracts, Columbus, OH. May 12, 2007.

Sucrow, Wolfgang et al., "Stable Pyrazolium Betaines by Addition of 1,1-Dialkyl-hydrazines to Acetylenecarboxylic Esters," Angewandte Chemie International Edition (1975), vol. 14, No, 8, pp. 560-561.
International Search Report dated Jul. 7, 2009, for EP 07291628.
European Search Report dated Jul. 7, 2008.
Ashton W.T. et al., "A Regioselective Route to 3-Alkyl-1-Aryl-1H-Pyrazole-5-Carboxylates: Synthetic Studies and Structural Assignments", Journal of Heterocyclic Chemistry 30:307-311 (Mar.-Apr. 1993).
Auzzi G. et al., "Halogenation of Some Pyrazolo[1,5-a]Pyrimidine Derivatives", Farmaco, Ed. Sci. 34(9):743-750 (1979), together with an English-language abstract.
Baldoli C. et al., "A Novel Synthesis of 5-Chloro-3-Methoxycarbonyl-1-Arylpyrazoles from Arylazomethylenetriphenylphosphoranes", Journal of Heterocyclic Chemistry 26:241-244 (Jan.-Feb. 1989).
Dangelmaier C. et al., "Potentiation of Thromboxane A2-Induced Platelet Secretion by Gi Signaling Through the Phosphoinositide-3 Kinase Pathway", Journal of Thrombosis and Haemostasis 85:341-348 (2001).
Farina F. et al., "1,3-Dipolar Cycloadditions With Methyl 4-Oxo- and 4-Hydroxy-2-Butynoates. Synthesis of Functionalized Pyrazoles and Triazoles", Heterocycles 29(5):967-974 (1989).
Gachet C., "ADP Receptors of Platelets and Their Inhibition", Journal of Thrombosis and Haemostasis 86:222-232 (2001).
Holzer W. et al., "N1-Substituted 3,5-Dimethoxy-4-Halogeno-1H-Pyrazoles: Synthesis and NMR Study", Journal of Heterocyclic Chemistry 32:1351-1354 (Jul.-Aug. 1995).
Makino K. et al., "Synthesis of Pyrazoles and Condensed Pyrazoles", Journal of Heterocyclic Chemistry 36:321-332 (Mar.-Apr. 1999).
Makino K. et al., "Synthesis of Pyrazoles", Journal of Heterocyclic Chemistry 35:489-497 (May-Jun. 1998).
Markova N.K. et al., "Study of the Reaction of 1-Dialkylamino(Alkoxy)-1-Buten-3-Ones With Some 1,3-Dipolar Systems", Zh. Org. Khimii 19(11):2281-2285 (1983), together with an English-language abstract.
Morimoto K. et al., "Synthesis of Halosulfuron-Methyl Via Selective Chlorination at 3-and/or 5-Position of Pyrazole-4- Carboxylates", Journal of Heterocyclic Chemistry 34:537-540 (Mar.-Apr. 1997).
Savi P. et al., "Identification and Biological Activity of the Active Metabolite of Clopidogrel", Journal of Thrombosis and Haemostasis 84:891-896 (2000).
Database Registry, Chemical Abstracts Service, (Dec. 5, 2007), retrieved from STN for RN 956728-06-6.
Extended European Search Report dated Jul. 7, 2008 received from related Application No. 07291628.1.
International Search Report and Written Opinion dated Jul. 7, 2009 received from the European Patent Office from related Application No. PCT/EP2008/010573.

PYRAZOLE-CARBOXAMIDE DERIVATIVES AS P2Y12 ANTAGONISTS

FIELD OF THE INVENTION

The present invention relates to compounds of the formula I,

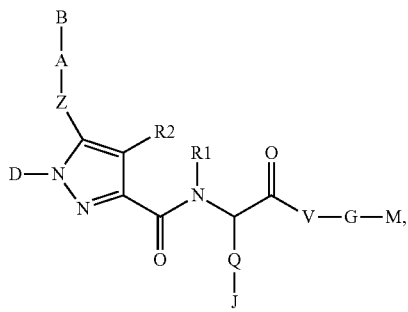

wherein
R1; R2; Z; A; B; D; Q; J; V; G and M have the meanings indicated below. The compounds of the formula I are valuable pharmacologically active compounds. They exhibit a strong anti-aggregating effect on platelets and thus an anti-thrombotic effect and are suitable e.g. for the therapy and prophylaxis of cardio-vascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

BACKGROUND OF THE INVENTION

In the industrialized world thrombotic complications are one of the major causes of death. Examples of conditions associated with pathological thrombus formation include deep vein thrombosis, venous and arterial thromboembolism, thrombophlebitis, coronary and cerebral arterial thrombosis, cerebral embolism, renal embolism and pulmonary embolism, disseminated intravascular coagulation, transient ischemic attacks, strokes, acute myocardial infarction, unstable angina, chronic stable angina, peripheral vascular disease, preeclampsia/eclampsia, and thrombotic cytopenic purpura. Also during or following invasive procedures, including insertion of endovascular devices and protheses, carotid endarterectomy, angioplasty, CABG (coronary artery bypass graft) surgery, vascular graft surgery, and stent placements, thrombotic and restenotic complications could occur.

Platelet adhesion and aggregation play a critical role in these intravascular thrombotic events. Platelets can be activated by mediators released from circulating cells and damaged endothelial cells lining the vessel or by exposed subendothelial matrix molecules such as collagen, or by thrombin, which is formed in the coagulation cascade. Furthermore platelets can be activated under conditions of high shear blood flow in diseased vessels. Following activation, platelets, which normally circulate freely in the vasculature, and other cells, accumulate at the site of a vessel injury to form a thrombus and recruit more platelets to the developing thrombus. During this process, thrombi can grow to a sufficient size to partly or completely block arterial blood vessels.

In veins thrombi can also form in areas of stasis or slow blood flow. These venous thrombi can create emboli that travel through the circulatory system, as they easily detach portions of themselves. These traveling emboli can block other vessels, such as pulmonary or coronary arteries, which can result in the above-mentioned pathological outcomes such as pulmonary or coronary embolism.

In summary, for venous thrombi, morbidity and mortality arise primarily after embolization or distant blockade of vessels, whereas arterial thrombi cause serious pathological conditions by local blockade.

It was demonstrated by many studies that ADP (adenosine 5'-diphosphate) is an important mediator of platelet activation and aggregation. It therefore plays a key role in the initiation and progression of arterial thrombus formation (Maffrand, et al., Thromb. Haemostas. (1988); 59: 225-230; Herbert, et al., Arterioscl. Thromb. (1993), 13: 1171-1179).

Upon activation by various agents, such as collagen and thrombin, ADP is released from blood platelets in the vasculature, as well as from damaged blood cells, endothelium or tissues. The ADP-induced platelet aggregation is triggered by its binding to two specific G protein-coupled receptors expressed on the plasma membrane of human platelets: P2Y1, and P2Y12. ADP binding to these receptors induces inhibition of adenylyl cyclase and modulation of intracellular signaling pathways such as influx and mobilization of intracellular $Ca^{2+}$, activation of phosphoinositide-3 kinase (PI3K), shape change, secretion of other mediators, and platelet aggregation (Dangelmaier, et al. Thromb. Haemost. (2001), 85: 341-348). Activation by ADP results in the recruitment of more platelets and stabilization of existing platelet aggregates. Activation of the $P2Y_1$ receptor leads to calcium mobilization from intracellular stores, platelet shape change and initiation of aggregation.

Activation of the P2Y12 receptor (also referred to as HORK3, P2RY12, SP1999, P2TAC, P2T or P2YAC) by ADP, leads to inhibition of adenylyl cyclase and activation of PI3K. Activation of P2Y12 is required for platelet secretion and stabilization of platelet aggregates (Gachet, Thromb. Haemost. (2001), 86, 222-232; Andre, et al., J. Clin. Invest., (2003), 112, 398-406).

There are several reports about directly or indirectly acting synthetic inhibitors of ADP-dependent platelet aggregation, which show antithrombotic activity.

The orally active thienopyridines, ticlopidine and clopidogrel, react covalently with the $P2Y_{12}$ receptor and lead to an irreversible platelet inhibition in vivo. They also inhibit binding of radiolabeled ADP receptor agonist 2-methylthioadenosine 5'-diphosphate to platelets, and other ADP-dependent events (Savi, et al., Thromb Haemost. (2000), 84: 891-896).

Houille et al. (WO 2005/000281 and WO 2005/002574) disclose pyrazolidinedione derivatives, useful as antithrombotic agents via inhibition of the platelet ADP receptor. Caroff et al. (WO2006/114774) disclose pyrimidine derivatives and their use as P2Y12 receptor antagonists.

However, besides being effective P2Y12 antagonists, which antagonize the effect of endogenous ADP on its platelet ADP receptor, it is desirable that such antagonists also have further advantageous properties, for instance stability in plasma and liver and selectivity versus other receptors whose agonism or antagonism is not intended. There is an ongoing need for further low molecular weight P2Y12 antagonist, which are effective and have the above advantages as well.

The present invention satisfies the above needs by providing novel pyrazole derivatives of the formula I, which exhibit better P2Y12 antagonistic activity and are favorable agents with high bioavailability.

DESCRIPTION OF THE INVENTION

Thus, the present invention relates to compounds of formula I,

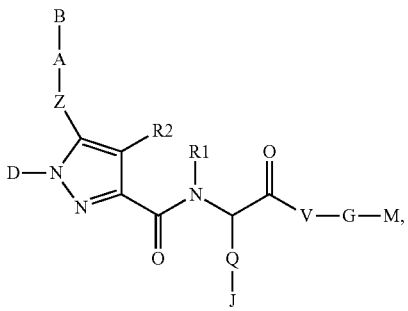

wherein

D is 1) 3- to 15-membered heterocyclic residue, containing 1, 2, or 3 heteroatoms chosen from nitrogen, sulfur or oxygen, wherein said heterocyclic residue is monocyclic or bicyclic and wherein said heterocyclic residue is unsubstituted or substituted 1, 2, 3, 4, 5 or 6 times by R4,
2) —$(C_6-C_{14})$-aryl, wherein aryl is unsubstituted or substituted 1, 2, 3, 4, 5 or 6 times by R4,
3) —$(C_3-C_8)$-cycloalkyl, wherein cycloalkyl is unsubstituted or substituted 1, 2, 3, 4, 5 or 6 times by R4, or
4) —$(C_1-C_6)$-alkyl, wherein alkyl is unsubstituted or substituted 1, 2, 3, 4, 5 or 6 times by R4, Q is 1) —$(C_0-C_4)$-alkylene-O—$(C_0-C_4)$-alkylene-,
2) —$(C_0-C_4)$-alkylene-O—C(O)—N(R10)-$(C_0-C_4)$-alkylene-,
3) —$(C_0-C_4)$-alkylene-C(O)—$(C_0-C_4)$-alkylene-,
4) —$(C_0-C_4)$-alkylene-C(O)—O—$(C_0-C_4)$-alkylene-, wherein alkylene is unsubstituted or mono-, di- or trisubstituted independently of one another by R13,
5) —$(C_0-C_4)$-alkylene-C(O)—N(R10)-,
6) —$(C_0-C_4)$-alkylene-N(R10)-$(C_0-C_4)$-alkylene-,
7) —$(C_0-C_4)$-alkylene-N(R10)-C(O)—$(C_0-C_4)$-alkylene-,
8) —$(C_0-C_4)$-alkylene-N(R10)-C(O)—O—$(C_0-C_4)$-alkylene-,
9) —$(C_0-C_4)$-alkylene-N(R10)-C(O)—N(R10)-$(C_0-C_4)$-alkylene-,
10) —$(C_0-C_4)$-alkylene-N(R10)-SO$_2$—$(C_0-C_4)$-alkylene-,
11) —$(C_0-C_4)$-alkylene-N(R10)-SO$_2$—NR$^{10}$—$(C_0-C_4)$-alkylene-,
12) —$(C_0-C_4)$-alkylene-S(O)—$(C_0-C_4)$-alkylene-,
13) —$(C_0-C_4)$-alkylene-SO$_2$—$(C_0-C_4)$-alkylene-,
14) —$(C_0-C_4)$-alkylene-SO$_2$—N(R10)-$(C_0-C_4)$-alkylene-, or
15) —$(C_0-C_4)$-alkylene-heterocyclyl-$(C_0-C_4)$-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, and wherein said heterocyclyl is unsubstituted or mono-, di- or trisubstituted independently of one another by R14; and wherein the alkyl residues are unsubstituted or mono-, di- or trisubstituted independently of one another by halogen, —NH$_2$, —OH; or —$(C_3-C_6)$-cycloalkyl, wherein cycloalkyl is unsubstituted or mono-, di- or trisubstituted independently of one another by halogen, —NH$_2$ or —OH, J is 1) hydrogen atom,
2) —$(C_1-C_6)$-alkyl, wherein alkyl is unsubstituted or mono-, di- or trisubstituted independently of one another by R13,
3) —$(C_0-C_4)$-alkylene-O—CH$_2$—$(C_1-C_3)$-fluoroalkylene-CH$_2$—O—$(C_1-C_4)$-alkyl,
4) —$(C_0-C_4)$-alkylene-C(O)—R11,
5) —$(C_0-C_4)$-alkylene-C(O)—O—R11,
6) —$(C_0-C_4)$-alkylene-C(O)—O—$(C_1-C_4)$-alkylene-O—C(O)—R17, wherein —$(C_1-C_4)$-alkylene is unsubstituted or mono-, di- or trisubstituted independently of one another by R15,
7) —$(C_0-C_4)$-alkylene-C(O)—O—$(C_1-C_4)$-alkylene-O—C(O)—O—R17, wherein —$(C_1-C_4)$-alkylene is unsubstituted or mono-, di- or trisubstituted independently of one another by R15,
8) —$(C_0-C_4)$-alkylene-C(O)—N(R11)-R13
9) —$(C_0-C_4)$-alkylene-N(R11)-R13,
10) —$(C_0-C_4)$-alkylene-N(R10)-SO$_2$—R10,
11) —$(C_0-C_4)$-alkylene-S—R10,
12) —$(C_0-C_4)$-alkylene-SO$_s$—R11, wherein s is 1 or 2,
13) —$(C_0-C_4)$-alkylene-SO$_t$—N(R11)-R12, wherein t is 1 or 2,
14) —$(C_0-C_4)$-alkylene-SO$_w$—N(R11)-R13, wherein w is 1 or 2,
15) —$(C_0-C_4)$-alkylene-R22,
16) —$(C_0-C_4)$-alkylene-$(C_3-C_8)$-cycloalkyl, wherein cycloalkyl is unsubstituted or mono-, di- or trisubstituted independently of one another by R13,
17) —$(C_0-C_4)$-alkylene-$(C_3-C_7)$-cycloalkenyl, wherein cycloalkyl is unsubstituted or mono-, di- or trisubstituted independently of one another by R14,
18) —$(C_0-C_4)$-alkylene-$(C_6-C_{14})$-aryl, wherein aryl is mono-, di- or trisubstituted independently of one another by R13, or
19) —$(C_0-C_4)$-alkylene-$(C_3-C_{15})$-heterocyclyl, wherein heterocyclyl is un-substituted or mono-, di- or trisubstituted independently of one another by R13, Z is 1) —$(C_0-C_4)$-alkylene-O—$(C_0-C_4)$-alkylene-,
2) —$(C_0-C_4)$-alkylene-O—$(C_0-C_4)$-alkylene-C(O)—$(C_0-C_4)$-alkylene-,
3) —$(C_0-C_4)$-alkylene-O—$(C_0-C_4)$-alkylene-C(O)—N(R10)-$(C_0-C_4)$-alkylene-,
4) —$(C_0-C_4)$-alkylene-C(O)—$(C_0-C_4)$-alkylene-,
5) —$(C_0-C_4)$-alkylene-N(R10)-$(C_0-C_4)$-alkylene-,
6) —$(C_0-C_4)$-alkylene-N(R10)-C(O)—$(C_0-C_4)$-alkylene-,
7) —$(C_0-C_4)$-alkylene-N(R10)-C(O)—O—$(C_0-C_4)$-alkylene-,
8) —$(C_0-C_4)$-alkylene-N(R10)-C(O)—N(R10)-$(C_0-C_4)$-alkylene-,
9) —$(C_0-C_4)$-alkylene-N(R10)-SO$_2$—$(C_0-C_4)$-alkylene-,
10) —$(C_0-C_4)$-alkylene-N(R10)-SO$_2$—N(R10)-$(C_0-C_4)$-alkylene-,
11) —$(C_0-C_4)$-alkylene-S—$(C_0-C_4)$-alkylene-,
12) —$(C_0-C_4)$-alkylene-S(O)—$(C_0-C_4)$-alkylene-,
13) —$(C_0-C_4)$-alkylene-SO$_2$—$(C_0-C_4)$-alkylene-,
14) —$(C_0-C_4)$-alkylene-SO$_2$—N(R10)-$(C_0-C_4)$-alkylene-, or
15) —$(C_0-C_4)$-alkylene-$(C_3-C_8)$-cycloalkyl-$(C_0-C_4)$-alkylene-, A is 1) a covalent bond,
2) —$(C_1-C_8)$-alkylene-,
3) —$(C_2-C_{10})$-alkenylene-, or
4) —$(C_3-C_8)$-cycloalkylene-, B is 1) hydrogen atom,
2) —($C_1$-$C_6$)-alkyl,
3) —($C_2$-$C_{10}$)-alkenyl, wherein alkenyl is un-substituted or mono-, di- or trisubstituted independently of one another by halogen,
4) —($C_2$-$C_{10}$)-alkynyl,
5) —($C_1$-$C_3$)-fluoroalkyl,
6) —($C_0$-$C_4$)-alkylene-CH(OH)—($C_0$-$C_4$)-alkyl,
7) —($C_0$-$C_4$)-alkylene-O—($C_0$-$C_4$)-alkyl,
8) —($C_0$-$C_4$)-alkylene-O—C(O)—N(R10)-($C_0$-$C_4$)-alkyl,
9) —($C_0$-$C_4$)-alkylene-C(O)—($C_1$-$C_4$)-alkyl,
10) —($C_0$-$C_4$)-alkylene-C(O)—O—($C_0$-$C_4$)-alkyl,
11) —($C_0$-$C_4$)-alkylene-C(O)—N(R10)-($C_0$-$C_4$)-alkyl,
12) —($C_0$-$C_4$)-alkylene-N(R10)-($C_0$-$C_4$)-alkyl,
13) —($C_0$-$C_4$)-alkylene-N(R10)-C(O)—($C_0$-$C_4$)-alkyl,
14) —($C_0$-$C_4$)-alkylene-N(R10)-C(O)—O—($C_0$-$C_4$)-alkyl,
15) —($C_0$-$C_4$)-alkylene-N(R10)-C(O)—N(R10)-($C_0$-$C_4$)-alkyl,
16) —($C_0$-$C_4$)-alkylene-N(R10)-$SO_2$—($C_0$-$C_4$)-alkyl,
17) —($C_0$-$C_4$)-alkylene-N(R10)-$SO_2$—N(R10)-($C_0$-$C_4$)-alkyl,
18) —($C_0$-$C_4$)-alkylene-S—($C_0$-$C_4$)-alkyl,
19) —($C_0$-$C_4$)-alkylene-S(O)—($C_0$-$C_4$)-alkyl,
20) —($C_0$-$C_4$)-alkylene-$SO_2$—($C_0$-$C_4$)-alkyl,
21) —($C_0$-$C_4$)-alkylene-$SO_2$—N(R10)-($C_0$-$C_4$)-alkyl, or
22) —($C_0$-$C_4$)-alkylene-($C_3$-$C_8$)-cycloalkyl-($C_0$-$C_4$)-alkyl, and
each of B is further unsubstituted or mono-, di- or trisubstituted independently of one another by R3,
V is a monocyclic or bicyclic 3- to 15-membered heterocyclyl, wherein heterocyclyl is unsubstituted or mono-, di- or trisubstituted independently of one another by R14,
G is 1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N($R^{10}$)—($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N($R^{10}$)—($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, wherein heterocyclyl is unsubstituted or mono-, di- or trisubstituted independently of one another by R14; and wherein the alkylene residue is unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

M is 1) hydrogen atom,
2) —($C_1$-$C_8$)-alkyl, wherein alkyl is unsubstituted or mono-, di- or trisubstituted independently of one another by R14,
3) —($C_1$-$C_8$)-alkylen-N(R10)$_2$,
4) —C(O)—O—R12,
5) —C(O)—N(R11)-R12,
6) —($C_3$-$C_8$)-cycloalkyl, wherein said cycloalkyl is unsubstituted or mono-, di- or trisubstituted independently of one another by R14,
7) —($C_6$-$C_{14}$)-aryl, wherein aryl is unsubstituted or mono-, di- or trisubstituted independently of one another by R14, or
8) a monocyclic or bicyclic 3- to 15-membered heterocyclyl, wherein heterocyclyl is unsubstituted or mono-, di- or trisubstituted independently of one another by R14,
R1 is hydrogen atom, halogen or —($C_1$-$C_4$)-alkyl, wherein alkyl is unsubstituted or substituted one to three times by R13; —($C_1$-$C_3$)-alkylene-C(O)—NH—R10 or —($C_1$-$C_3$)-alkylene-C(O)—O—R10,
R2 is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl, or
6) phenyl, wherein phenyl is unsubstituted or mono-, di- or trisubstituted independently of one another by R13, or
if two —OR10 residues are attached to adjacent atoms they can form together with the atoms which they are attached to a 5- or 6-membered ring, which is unsubstituted or substituted one, two, three or four times by R13,
if two —($C_1$-$C_6$)-alkyl residues are attached to adjacent atoms they can form together with the atoms which they are attached to a 5- or 6-membered cycloalkyl ring, which is unsubstituted or substituted one, two, three or four times by R13,
R3 is 1) hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-O—R19, wherein R19 is
a) hydrogen atom,
b) —($C_1$-$C_4$)-alkyl, wherein alkyl is unsubstituted or mono-, di- or trisubstituted independently of one another by R13,
c) —($C_3$-$C_8$)-cycloalkyl, wherein alkyl is unsubstituted or mono-, di- or trisubstituted independently of one another by R13,
d) phenyl, wherein phenyl is unsubstituted or mono-, di- or trisubstituted independently of one another by R13,
e) —$CF_3$, or
f) —$CHF_2$, 7) —NO$_2$,
8) —CN,
9) —(C$_0$-C$_4$)-alkylene-O—CH$_2$—(C$_1$-C$_3$)-fluoroalkylene-CH$_2$—O—(C$_1$-C$_4$)-alkyl,
10) —(C$_0$-C$_4$)-alkylene-C(O)—R11,
11) —(C$_0$-C$_4$)-alkylene-C(O)—O—R11,
12) —(C$_0$-C$_4$)-alkylene-C(O)—O—(C$_1$-C$_4$)-alkylene-O—C(O)—R17, wherein —(C$_1$-C$_4$)-alkylene is unsubstituted or mono-, di- or trisubstituted independently of one another by R15,
13) —(C$_0$-C$_4$)-alkylene-C(O)—O—(C$_1$-C$_4$)-alkylene-O—C(O)—O—R17, wherein —(C$_1$-C$_4$)-alkylene is unsubstituted or mono-, di- or trisubstituted independently of one another by R15,
14) —(C$_0$-C$_4$)-alkylene-C(O)—N(R11)-R12,
15) —(C$_0$-C$_4$)-alkylene-C(O)—N(R11)-R13,
16) —(C$_0$-C$_4$)-alkylene-C(O)—N[(C$_0$-C$_4$)-alkylene]-R13, wherein alkyl and cycloalkyl are unsubstituted or mono-, di- or trisubstituted independently of one another by R13,
17) —(C$_0$-C$_4$)-alkylene-C(O)—N[(C$_0$-C$_4$)-alkylene-(C$_3$-C$_8$)-cycloalkyl]-R13, wherein alkyl and cycloalkyl is unsubstituted or mono-, di- or trisubstituted independently of one another by R13,
18) —(C$_0$-C$_4$)-alkylene-N(R11)-R12,
19) —(C$_0$-C$_4$)-alkylene-N(R11)-R13,
20) —(C$_0$-C$_4$)-alkylene-N(R10)-SO$_2$—R10,
21) —(C$_0$-C$_4$)-alkylene-S—R10,
22) —(C$_0$-C$_4$)-alkylene-SO$_s$—R11, wherein s is 1 or 2,
23) —(C$_0$-C$_4$)-alkylene-SO$_t$—N(R11)-R12, wherein t is 1 or 2,
24) —(C$_0$-C$_4$)-alkylene-SO$_w$—N(R11)-R13, wherein w is 1 or 2,
25) —(C$_0$-C$_4$)-alkylene-SO$_u$—(C$_0$-C$_4$)-alkylene-C(O)—O—R10, wherein u is 1 or 2,
26) —(C$_0$-C$_4$)-alkylene-(C$_3$-C$_8$)-cycloalkyl, wherein cycloalkyl is unsubstituted or mono-, di- or trisubstituted independently of one another by R13,
27) —(C$_0$-C$_4$)-alkylene-(C$_6$-C$_{14}$)-aryl, wherein aryl is mono-, di- or trisubstituted independently of one another by R13,
28) —(C$_0$-C$_4$)-alkylene-(C$_3$-C$_{15}$)-heterocyclyl-(C$_0$-C$_4$)-alkylene-, wherein heterocyclyl is mono-, di- or trisubstituted independently of one another by R13,
29) —(C$_0$-C$_4$)-alkylene-O—(C$_0$-C$_4$)-alkylene-(C$_6$-C$_{14}$)-aryl, wherein aryl is mono-, di- or trisubstituted independently of one another by R13,
30) —(C$_0$-C$_4$)-alkylene-O—(C$_0$-C$_4$)-alkylene-(C$_3$-C$_{15}$)-heterocyclyl, wherein heterocyclyl is unsubstituted or mono-, di- or trisubstituted independently of one another by R13,
31) —(C$_0$-C$_4$)-alkylene-N(R13)—(C$_0$-C$_4$)-alkylene-(C$_6$-C$_{14}$)-aryl, wherein aryl is mono-, di- or trisubstituted independently of one another by R13, or
32) —(C$_0$-C$_4$)-alkylene-N(R13)—(C$_0$-C$_4$)-alkylene-(C$_3$-C$_{15}$)-heterocyclyl, wherein heterocyclyl is un-substituted or mono-, di- or trisubstituted independently of one another by R13, R4 is 1) hydrogen atom,
2) —(C$_0$-C$_6$)-alkyl, wherein alkyl is unsubstituted or mono-, di- or trisubstituted independently of one another by R13,
3) —(C$_0$-C$_4$)-alkylene-O—R10,
4) halogen,
5) —(C$_1$-C$_3$)-fluoroalkyl, or
6) —CN,
7) —NO$_2$,
8) —S—CH$_3$,
9) —SO$_2$—NH$_2$,
10) phenyl, wherein phenyl is unsubstituted or mono-, di- or trisubstituted independently of one another by R13, R10 is hydrogen atom, —(C$_1$-C$_4$)-alkyl, —(C$_1$-C$_4$)-alkyl-OH, —(C$_1$-C$_3$)-fluoroalkyl or —(C$_0$-C$_4$)-alkylene-O—(C$_1$-C$_4$)-alkyl, R11 and R12 are independently of one another identical or different and are
1) hydrogen atom,
2) —(C$_1$-C$_6$)-alkyl, wherein alkyl is unsubstituted or mono-, di- or trisubstituted independently of one another by R13,
3) —O—R17,
4) —SO$_t$—R10, wherein t is 1 or 2,
5) —(C$_1$-C$_3$)-fluoroalkyl,
6) —(C$_0$-C$_6$)-alkylene-(C$_3$-C$_8$)-cycloalkyl, wherein alkylene and cycloalkyl independently from one another are unsubstituted or mono-, di- or trisubstituted independently of one another by R13,
7) —(C$_0$-C$_6$)-alkylene-(C$_6$-C$_{14}$)-aryl, wherein alkylene and aryl independently from one another are unsubstituted or mono-, di- or trisubstituted by R13, or
8) —(C$_0$-C$_4$)-alkylene-heterocyclyl-(C$_0$-C$_4$)-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, wherein said heterocyclyl is unsubstituted or mono-, di- or trisubstituted independently of one another by R13, or R11 and R12 form together with the nitrogen atom to which they are attached a 4-, 5-, 6-, 7- or 8-membered monocyclic heterocyclic ring which in addition to the nitrogen atom can contain one or two identical or different ring heteroatoms chosen from oxygen, sulfur and nitrogen, and wherein said ring is unsubstituted or substituted depending on the number of ring atoms one, two, three or four times by R13, R13 is hydrogen atom, —(C$_1$-C$_8$)-alkyl, —(C$_2$-C$_{10}$)-alkenyl-, —(C$_2$-C$_{10}$)-alkynyl, —(C$_3$-C$_8$)-cycloalkyl, —(C$_0$-C$_4$)-alkylene-R22, —(C$_1$-C$_8$)-alkoxy, phenyl, phenyloxy-, —(C$_1$-C$_8$)-alkoxy-phenyl, —(C$_0$-C$_4$)-alkylene-O—R10, —OH, —O—R15, —C(O)—R10, halogen, —C(O)—O—R10, —C(O)—N(R10)-R20, —N(R10)-R20, —NH—C(O)—O—R10, —(C$_1$-C$_3$)-fluoroalkyl, NH—C(O)—NH—R10, —NO$_2$, —CN, =O, —CF$_3$, —O—CF$_3$, —Si—(CH$_3$)$_3$,
S—R10, —N(R10)-S(O)$_u$—R10, wherein u is 1 or 2, —S(O)$_v$—N(R10)-R20, wherein v is 1 or 2, —SO$_r$R10, wherein r is 1 or 2, —(C$_0$-C$_4$)-alkylene-C(O)—O—C(R15, R16)-O—C(O)—R17 or —(C$_0$-C$_4$)-alkylene-C(O)—O—C(R15, R16)-O—C(O)—O—R17, R14 is hydrogen, halogen, —OH, =O, —NO$_2$, —CN, —NH$_2$, —S—R18, —(C$_1$-C$_6$)-alkyl, —(C$_2$-C$_{10}$)-alkenyl, —(C$_2$-C$_{10}$)-alkynyl, —(C$_1$-C$_4$)-alkoxy, —C(O)—O—(C$_1$-C$_4$)-alkyl, —(C$_1$-C$_4$)-alkylene-C(O)—OH, —(C$_1$-C$_4$)-alkylene-C(O)—NH$_2$, —(C$_1$-C$_3$)-fluoroalkyl, —(C$_0$-C$_8$)-alkylene-SO$_2$—(C$_1$-C$_4$)-alkyl, —(C$_0$-C$_8$)-alkylene-SO$_2$—(C$_1$-C$_3$)-fluoroalkyl, —(C$_0$-C$_8$)-alkylene-SO$_2$—N(R18)-R21, —(C$_1$-C$_4$)-alkylene-C(O)—NH—(C$_1$-C$_8$)-alkyl, —(C$_1$-C$_4$)-alkylene-C(O)—N—[(C$_1$-C$_8$)-alkyl]$_2$, —N(R18)-C(O)—NH—(C$_1$-C$_8$)-alkyl or —N(R18)-C(O)—NH—[(C$_1$-C$_8$)-alkyl]$_2$,
wherein R18 and R21 are independently from each other hydrogen atom, —(C$_1$-C$_3$)-fluoroalkyl or —(C$_1$-C$_6$)-alkyl, R15 and R16 are independently of one another hydrogen atom, —($C_1$-$C_6$)-alkyl, or together with the carbon atom to which they are bonded form a —($C_3$-$C_6$)-cycloalkyl, which is unsubstituted or mono, di- or trisubstituted by R10, R17 is hydrogen atom, —($C_1$-$C_6$)-alkyl, —($C_1$-$C_6$)-alkyl-OH, —($C_1$-$C_6$)-alkylene-O—($C_1$-$C_6$)-alkyl, —($C_1$-$C_6$)-alkylene-O—($C_1$-$C_6$)-alkylene-($C_3$-$C_8$)-cycloalkyl, or —($C_0$-$C_6$)-alkylene-($C_3$-$C_8$)-cycloalkyl, wherein each cycloalkyl ring is unsubstituted or substituted one, two or three times by —OH, —O—($C_1$-$C_4$)-alkyl or R10, R20 is hydrogen atom, —($C_1$-$C_4$)-alkyl, —($C_1$-$C_4$)-alkyl-OH, —($C_1$-$C_3$)-fluoroalkyl or —($C_0$-$C_4$)-alkylene-O—($C_1$-$C_4$)-alkyl, and R22 is a residue from the following list:

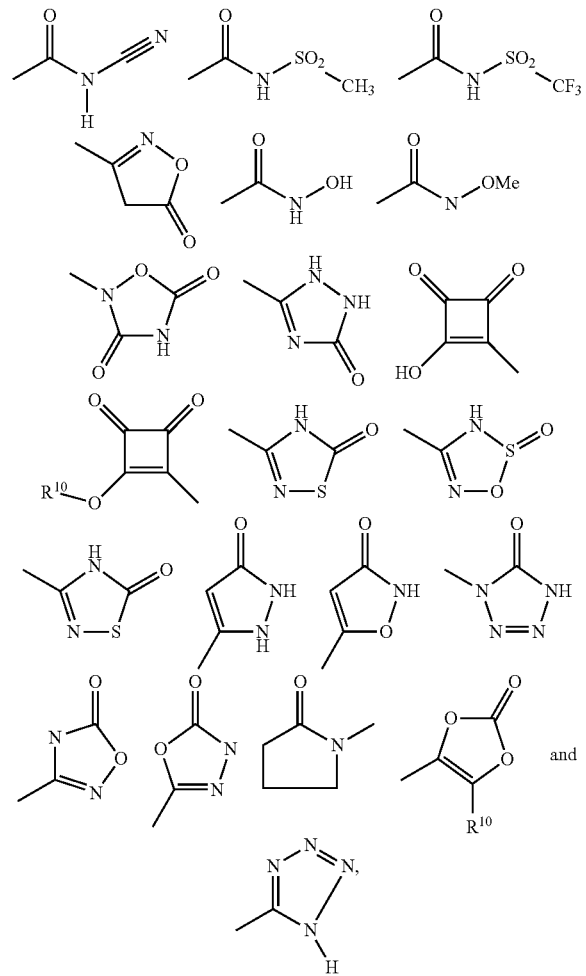

wherein Me is methyl, in all its stereoisomeric forms and mixtures thereof in any ratio, and its physiologically tolerable salts.

2) The present invention also relates to compounds of the formula I, wherein

D is 1) 3- to 15-membered heterocyclic residue selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzofuranyl, benzoimidazolyl, benzoisothiazolyl, benzoisoxazolyl, benzotetrazolyl, benzothiazolyl, benzothiofuranyl, benzothiophenyl, benzotriazolyl, benzoxazolyl, carbazolyl, 4aH-carbazolyl, carbolinyl, chromanyl, chromenyl, cinnolinyl, decahydroquinolinyl, diaza-bicyclohexanyl, diaza-bicycloheptanyl, 2,5-Diaza-bicyclo[2.2.1]heptanyl, 1,2-diazapanyl, diazaspirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, dioxazolyl, dioxazinyl, 1,3-dioxolanyl, 1,3-dioxolenyl, 3,3-dioxo[1,3,4]oxathiazinyl, 6H-1,5,2-dithiazinyl, furyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, wherein said heterocyclic residue is unsubstituted or substituted 1, 2, 3, 4, 5 or 6 times by R4, 2) —($C_6$-$C_{14}$)-aryl, wherein aryl is selected from phenyl, naphthyl, biphenylyl, indanyl, anthryl or fluorenyl, wherein said aryl residue is unsubstituted or substituted 1, 2, 3, 4, 5 or 6 times by R4, 3) —($C_3$-$C_8$)-cycloalkyl, wherein cycloalkyl is unsubstituted or substituted 1, 2, 3, 4, 5 or 6 times by R4, or 4) —($C_1$-$C_6$)-alkyl, wherein alkyl is unsubstituted or substituted 1, 2, 3, 4, 5 or 6 times by R4, Q is 1) —($C_0$-$C_4$)-alkylene-O—($C_0$-$C_4$)-alkylene-,
2) —($C_0$-$C_4$)-alkylene-O—C(O)—N(R10)-($C_0$-$C_4$)-alkylene-,
3) —($C_0$-$C_4$)-alkylene-C(O)—($C_0$-$C_4$)-alkylene-,
4) —($C_0$-$C_4$)-alkylene-C(O)—O—($C_0$-$C_4$)-alkylene-, wherein alkylene is unsubstituted or mono-, di- or trisubstituted independently of one another by R13,
5) —($C_0$-$C_4$)-alkylene-C(O)—N(R10)-,
6) —($C_0$-$C_4$)-alkylene-N(R10)-($C_0$-$C_4$)-alkylene-,
7) —($C_0$-$C_4$)-alkylene-N(R10)-C(O)—($C_0$-$C_4$)-alkylene-,
8) —($C_0$-$C_4$)-alkylene-N(R10)-C(O)—O—($C_0$-$C_4$)-alkylene-,
9) —($C_0$-$C_4$)-alkylene-N(R10)-C(O)—N(R10)-($C_0$-$C_4$)-alkylene-,
10) —($C_0$-$C_4$)-alkylene-N(R10)-$SO_2$—($C_0$-$C_4$)-alkylene-,
11) —($C_0$-$C_4$)-alkylene-N(R10)-$SO_2$—$NR^{10}$—($C_0$-$C_4$)-alkylene-,
12) —($C_0$-$C_4$)-alkylene-S(O)—($C_0$-$C_4$)-alkylene-,
13) —($C_0$-$C_4$)-alkylene-$SO_2$—($C_0$-$C_4$)-alkylene-,
14) —($C_0$-$C_4$)-alkylene-$SO_2$—N(R10)-($C_0$-$C_4$)-alkylene-, or
15) —($C_0$-$C_4$)-alkylene-heterocyclyl-($C_0$-$C_4$)-alkylene-, wherein heterocyclyl is as defined above, and wherein said heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH, J is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—$CH_2$—($C_1$-$C_3$)-fluoroalkylene-$CH_2$—O—($C_1$-$C_4$)-alkyl,
4) —($C_0$-$C_4$)-alkylene-C(O)—R11,
5) —($C_0$-$C_4$)-alkylene-C(O)—O—R11,
6) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
7) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
8) —($C_0$-$C_4$)-alkylene-C(O)—N(R11)-R13
9) —($C_0$-$C_4$)-alkylene-N(R11)-R13,
10) —($C_0$-$C_4$)-alkylene-N(R10)-$SO_2$—R10,
11) —($C_0$-$C_4$)-alkylene-S—R10,
12) —($C_0$-$C_4$)-alkylene-$SO_s$—R11, wherein s is 1 or 2,
13) —($C_0$-$C_4$)-alkylene-$SO_t$—N(R11)-R12, wherein t is 1 or 2,
14) —($C_0$-$C_4$)-alkylene-$SO_w$—N(R11)-R13, wherein w is 1 or 2,
15) —($C_0$-$C_4$)-alkylene-($C_3$-$C_8$)-cycloalkyl, wherein cycloalkyl is unsubstituted or mono-, di- or trisubstituted independently of one another by R13,
16) —($C_0$-$C_4$)-alkylene-($C_3$-$C_7$)-cycloalkenyl, wherein cycloalkyl is unsubstituted or mono-, di- or trisubstituted independently of one another by R14,
17) —($C_0$-$C_4$)-alkylene-($C_6$-$C_{14}$)-aryl, wherein aryl as defined above and is mono-, di- or trisubstituted independently of one another by R13, or
18) —($C_0$-$C_4$)-alkylene-($C_3$-$C_{16}$)-heterocyclyl, wherein heterocyclyl is as defined above and is un-substituted or mono-, di- or trisubstituted independently of one another by R13, Z is 1) —($C_0$-$C_4$)-alkylene-O—($C_0$-$C_4$)-alkylene-,
2) —($C_0$-$C_4$)-alkylene-O—($C_0$-$C_4$)-alkylene-C(O)—($C_0$-$C_4$)-alkylene-,
3) —($C_0$-$C_4$)-alkylene-O—($C_0$-$C_4$)-alkylene-C(O)—N(R10)-($C_0$-$C_4$)-alkylene-,
4) —($C_0$-$C_4$)-alkylene-C(O)—($C_0$-$C_4$)-alkylene-,
5) —($C_0$-$C_4$)-alkylene-N(R10)-($C_0$-$C_4$)-alkylene-,
6) —($C_0$-$C_4$)-alkylene-N(R10)-C(O)—($C_0$-$C_4$)-alkylene-,
7) —($C_0$-$C_4$)-alkylene-N(R10)-C(O)—O—($C_0$-$C_4$)-alkylene-,
8) —($C_0$-$C_4$)-alkylene-N(R10)-C(O)—N(R10)-($C_0$-$C_4$)-alkylene-,
9) —($C_0$-$C_4$)-alkylene-N(R10)-$SO_2$—($C_0$-$C_4$)-alkylene-,
10) —($C_0$-$C_4$)-alkylene-N(R10)-$SO_2$—N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-S(O)—($C_0$-$C_4$)-alkylene-,
13) —($C_0$-$C_4$)-alkylene-$SO_2$—($C_0$-$C_4$)-alkylene-,
14) —($C_0$-$C_4$)-alkylene-$SO_2$—N(R10)-($C_0$-$C_4$)-alkylene-, or
15) —($C_0$-$C_4$)-alkylene-($C_3$-$C_8$)-cycloalkyl-($C_0$-$C_4$)-alkylene-, A is 1) a covalent bond,
2) —($C_1$-$C_8$)-alkylene-,
3) —($C_2$-$C_{10}$)-alkenylene-, or
4) —($C_3$-$C_8$)-cycloalkylene-, B is 1) hydrogen atom,
2) —($C_1$-$C_6$)-alkyl,
3) —($C_2$-$C_{10}$)-alkenyl, wherein alkenyl is un-substituted or mono-, di- or trisubstituted independently of one another by halogen,
4) —($C_2$-$C_{10}$)-alkynyl,
5) —($C_1$-$C_3$)-fluoroalkyl,
6) —($C_0$-$C_4$)-alkylene-CH(OH)—($C_0$-$C_4$)-alkyl,
7) —($C_0$-$C_4$)-alkylene-O—($C_0$-$C_4$)-alkyl,
8) —($C_0$-$C_4$)-alkylene-O—C(O)—N(R10)-($C_0$-$C_4$)-alkyl,
9) —($C_0$-$C_4$)-alkylene-C(O)—($C_1$-$C_4$)-alkyl,
10) —($C_0$-$C_4$)-alkylene-C(O)—O—($C_0$-$C_4$)-alkyl,
11) —($C_0$-$C_4$)-alkylene-C(O)—N(R10)-($C_0$-$C_4$)-alkyl,
12) —($C_0$-$C_4$)-alkylene-N(R10)-($C_0$-$C_4$)-alkyl,
13) —($C_0$-$C_4$)-alkylene-N(R10)-C(O)—($C_0$-$C_4$)-alkyl,
14) —($C_0$-$C_4$)-alkylene-N(R10)-C(O)—O—($C_0$-$C_4$)-alkyl,
15) —($C_0$-$C_4$)-alkylene-N(R10)-C(O)—N(R10)-($C_0$-$C_4$)-alkyl,
16) —($C_0$-$C_4$)-alkylene-N(R10)-$SO_2$—($C_0$-$C_4$)-alkyl,
17) —($C_0$-$C_4$)-alkylene-N(R10)-$SO_2$—N(R10)-($C_0$-$C_4$)-alkyl,
18) —($C_0$-$C_4$)-alkylene-S—($C_0$-$C_4$)-alkyl,
19) —($C_0$-$C_4$)-alkylene-S(O)—($C_0$-$C_4$)-alkyl,
20) —($C_0$-$C_4$)-alkylene-$SO_2$—($C_0$-$C_4$)-alkyl,
21) —($C_0$-$C_4$)-alkylene-$SO_2$—N(R10)-($C_0$-$C_4$)-alkyl, or
22) —($C_0$-$C_4$)-alkylene-($C_3$-$C_8$)-cycloalkyl-($C_0$-$C_4$)-alkyl, and each of B is further unsubstituted or mono-, di- or trisubstituted independently of one another by R3, V is a monocyclic or bicyclic 3- to 15-membered heterocyclyl, wherein heterocyclyl is as defined above and is unsubstituted or mono-, di- or trisubstituted independently of one another by R14, G is 1) a covalent bond,
2) —($C_2$-$C_{10}$)-alkenyl-,
3) —($C_2$-$C_{10}$)-alkynyl-, 4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is as defined above and is unsubstituted or mono-, di- or trisubstituted independently of one another by R14; and wherein the alkylene residue is unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

M is 1) a hydrogen atom,
2) —($C_1$-$C_8$)-alkyl, wherein alkyl is unsubstituted or mono-, di- or trisubstituted independently of one another by R14,
3) —($C_1$-$C_8$)-alkylene-N(R10)$_2$,
4) —C(O)—O—R12,
5) —C(O)—N(R11)-R12,
6) —($C_3$-$C_8$)-cycloalkyl, wherein said cycloalkyl is unsubstituted or mono-, di- or trisubstituted independently of one another by R14,
7) —($C_6$-$C_{14}$)-aryl, wherein aryl is unsubstituted or mono-, di- or trisubstituted independently of one another by R14, or
8) a monocyclic or bicyclic 3- to 15-membered heterocyclyl, wherein heterocyclyl is as defined above and is unsubstituted or mono-, di- or trisubstituted independently of one another by R14, R1 is hydrogen atom, halogen or —($C_1$-$C_4$)-alkyl, wherein alkyl is unsubstituted or substituted one to three times by R13; —($C_1$-$C_3$)-alkylene-C(O)—NH—R10 or —($C_1$-$C_3$)-alkylene-C(O)—O—R10, R2 is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl, or
6) phenyl, wherein phenyl is unsubstituted or mono-, di- or trisubstituted independently of one another by R13, or if two —OR10 residues are attached to adjacent atoms they can form together with the atoms which they are attached to a 5- or 6-membered ring, which is unsubstituted or substituted one, two, three or four times by R13, if two —($C_1$-$C_6$)-alkyl residues are attached to adjacent atoms they can form together with the atoms which they are attached to a 5- or 6-membered cycloalkyl ring, which is unsubstituted or substituted one, two, three or four times by R13, R3 is 1) hydrogen atom,
2) halogen,
3) —($C_1$-$C_6$)-alkyl, wherein alkyl is unsubstituted or mono-, di- or trisubstituted independently of one another by R13,
4) —($C_0$-$C_4$)-alkylene-O—R19, wherein R19 is
  a) hydrogen atom,
  b) —($C_1$-$C_4$)-alkyl, wherein alkyl is unsubstituted or mono-, di- or trisubstituted independently of one another by R13,
  c) —($C_3$-$C_8$)-cycloalkyl, wherein alkyl is unsubstituted or mono-, di- or trisubstituted independently of one another by R13,
  d) phenyl, wherein phenyl is unsubstituted or mono-, di- or trisubstituted independently of one another by R13,
  e) —$CF_3$, or
  f) —$CHF_2$,
5) —($C_0$-$C_4$)-alkylene-C(O)—O—R11, or
6) —($C_0$-$C_4$)-alkylene-($C_6$-$C_{14}$)-aryl, wherein aryl is as defined above and is mono-, di- or trisubstituted independently of one another by R13, R4 is 1) hydrogen atom,
2) —($C_0$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl, or
6) —CN,
7) —$NO_2$,
8) —S—$CH_3$,
9) —$SO_2$—$NH_2$,
10) phenyl, wherein phenyl is unsubstituted or mono-, di- or trisubstituted independently of one another by R13, R10 is hydrogen atom, —($C_1$-$C_4$)-alkyl, —($C_1$-$C_4$)-alkyl-OH, —($C_1$-$C_3$)-fluoroalkyl or —($C_0$-$C_4$)-alkylene-O—($C_1$-$C_4$)-alkyl, R11 and R12 are independently of one another identical or different and are
1) hydrogen atom,
2) —($C_1$-$C_6$)-alkyl, wherein alkyl is unsubstituted or mono-, di- or trisubstituted independently of one another by R13,
3) —O—R17,
4) —$SO_t$—R10, wherein t is 1 or 2,
5) —($C_1$-$C_3$)-fluoroalkyl,
6) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13,
7) —($C_0$-$C_6$)-alkylene-($C_6$-$C_{14}$)-aryl, wherein alkylene and aryl independently from one another are unsubstituted or mono-, di- or trisubstituted by R13, or
8) —($C_0$-$C_4$)-alkylene-heterocyclyl-($C_0$-$C_4$)-alkylene-, wherein heterocyclyl is as define above and is unsubstituted or mono-, di- or trisubstituted independently of one another by R13, or R11 and R12 form together with the nitrogen atom to which they are attached a 4-, 5-, 6-, 7- or 8-membered monocyclic heterocyclic ring selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane, and wherein said ring is unsubstituted or substituted depending on the number of ring atoms one, two, three or four times by R13, R13 is hydrogen atom, —($C_1$-$C_8$)-alkyl, —($C_2$-$C_{10}$)-alkenyl-, —($C_2$-$C_{10}$)-alkynyl, —($C_3$-$C_8$)-cycloalkyl, —($C_1$-$C_8$)-alkoxy, phenyl, phenyloxy-, —($C_1$-$C_8$)-alkoxy-phenyl, —($C_0$-$C_4$)-alkylene-O—R10, —OH, —O—R15, —C(O)—R10, halogen, —C(O)—O—R10, —C(O)—N(R10)-R20, —N(R10)-R20, —NH—C(O)—O—R10, —($C_1$-$C_3$)-fluoroalkyl, NH—C(O)—NH—R10, —$NO_2$, —CN, =O, —$CF_3$, —O—$CF_3$, —Si—$(CH_3)_3$, S—R10, —N(R10)-S(O)$_u$—R10, wherein u is 1 or 2, —S(O)$_v$—N(R10)-R20, wherein v is 1 or 2, —$SO_r$R10, wherein r is 1 or 2, —($C_0$-$C_4$)-alkylene-C(O)—O—C(R15, R16)-O—C(O)—R17 or —($C_0$-$C_4$)-alkylene-C(O)—O—C(R15, R16)-O—C(O)—O—R17, R14 is hydrogen atom, halogen, —OH, =O, —$NO_2$, —CN, —$NH_2$, —S—R18, —($C_1$-$C_8$)-alkyl, —($C_2$-$C_{10}$)-alkenyl, —($C_2$-$C_{10}$)-alkynyl, —($C_1$-$C_4$)-alkoxy, —C(O)—O—($C_1$-$C_4$)-alkyl, —($C_1$-$C_4$)-alkylene-C(O)—OH, —($C_1$-$C_4$)-alkylene-C(O)—$NH_2$, —($C_1$-$C_3$)-fluoroalkyl, —($C_0$-$C_8$)-alkylene-$SO_2$—($C_1$-$C_4$)-alkyl, —($C_0$-$C_8$)-alkylene-$SO_2$—($C_1$-$C_3$)-fluoroalkyl, —($C_0$-$C_8$)-alkylene-$SO_2$—N(R18)-R21, —($C_1$-$C_4$)-alkylene-C(O)—NH—($C_1$-$C_8$)-alkyl, —($C_1$-$C_4$)-alkylene-C(O)—N—[($C_1$-$C_8$)-alkyl]$_2$, —N(R18)-C(O)—NH—($C_1$-$C_8$)-alkyl or —N(R18)-C(O)—NH—[($C_1$-$C_8$)-alkyl]$_2$, wherein R18 and R21 are independently from each other hydrogen atom, —($C_1$-$C_3$)-fluoroalkyl or —($C_1$-$C_6$)-alkyl, R15 and R16 are independently of one another hydrogen atom, —($C_1$-$C_6$)-alkyl, or together with the carbon atom to which they are bonded form a —($C_3$-$C_6$)-cycloalkyl, which is unsubstituted or mono, di- or trisubstituted by R10, R17 is hydrogen atom, —($C_1$-$C_6$)-alkyl, —($C_1$-$C_6$)-alkyl-OH, —($C_1$-$C_6$)-alkylene-O—($C_1$-$C_6$)-alkyl, —($C_1$-$C_6$)-alkylene-O—($C_1$-$C_6$)-alkylene-($C_3$-$C_8$)-cycloalkyl, or —($C_0$-$C_6$)-alkylene-($C_3$-$C_8$)-cycloalkyl, wherein each cycloalkyl ring is unsubstituted or substituted one, two or three times by —OH, —O—($C_1$-$C_4$)-alkyl or R10, and R20 is hydrogen atom, —($C_1$-$C_4$)-alkyl, —($C_1$-$C_4$)-alkyl-OH, —($C_1$-$C_3$)-fluoroalkyl or —($C_0$-$C_4$)-alkylene-O—($C_1$-$C_4$)-alkyl, in all its stereoisomeric forms and mixtures thereof in any ratio, and its physiologically tolerable salts.

3) The present invention also relates to compounds of the formula I, wherein

D is 1) 3- to 15-membered heterocyclic residue selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzofuranyl, benzoimidazolyl, benzoisothiazolyl, benzoisoxazolyl, benzotetrazolyl, benzothiazolyl, benzothiofuranyl, benzothiophenyl, benzotriazolyl, benzoxazolyl, carbazolyl, 4aH-carbazolyl, carbolinyl, chromanyl, chromenyl, cinnolinyl, decahydroquinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, dihydrofuro[2,3-b]etrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triazaspirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, wherein said heterocyclic residue is unsubstituted or substituted 1, 2, 3, 4, 5 or 6 times by R4, 2) —($C_6$-$C_{14}$)-aryl, wherein aryl is selected from phenyl or naphthyl, wherein said aryl residue is unsubstituted or substituted 1, 2, 3 or 4 times by R4, 3) —($C_3$-$C_8$)-cycloalkyl, wherein cycloalkyl is unsubstituted or substituted 1, 2, 3, 4, 5 or 6 times by R4, or
4) —($C_1$-$C_6$)-alkyl, wherein alkyl is unsubstituted or substituted 1, 2, 3, 4, 5 or 6 times by R4, Q is 1) —($C_0$-$C_4$)-alkylene-C(O)—O—($C_0$-$C_4$)-alkylene-, wherein alkylene is unsubstituted or mono-, di- or trisubstituted independently of one another by R13,
2) —($C_0$-$C_4$)-alkylene-C(O)—N(R10)-,
3) —($C_0$-$C_4$)-alkylene-N(R10)-($C_0$-$C_4$)-alkylene-,
4) —($C_0$-$C_4$)-alkylene-N(R10)-C(O)—($C_0$-$C_4$)-alkylene-, or
5) —($C_0$-$C_4$)-alkylene-N(R10)-C(O)—O—($C_0$-$C_4$)-alkylene-, J is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—O—R11,
4) —($C_0$-$C_4$)-alkylene-$SO_s$—R11, wherein s is 1 or 2,
5) —($C_0$-$C_4$)-alkylene-($C_3$-$C_8$)-cycloalkyl, wherein cycloalkyl is unsubstituted or mono-, di- or trisubstituted independently of one another by R13, or
6) —($C_0$-$C_4$)-alkylene-($C_3$-$C_7$)-cycloalkenyl, wherein cycloalkyl is unsubstituted or mono-, di- or trisubstituted independently of one another by R14, Z is 1) —($C_0$-$C_4$)-alkylene-O—($C_0$-$C_4$)-alkylene-,
2) —($C_0$-$C_4$)-alkylene-O—($C_0$-$C_4$)-alkylene-C(O)—($C_0$-$C_4$)-alkylene-, or
3) —($C_0$-$C_4$)-alkylene-O—($C_0$-$C_4$)-alkylene-C(O)—N(R10)-($C_0$-$C_4$)-alkylene-, A is 1) a covalent bond,
2) —($C_1$-$C_8$)-alkylene-,
3) —($C_2$-$C_{10}$)-alkenylene-, or
4) —($C_3$-$C_8$)-cycloalkylene-, B is 1) hydrogen atom,
2) —($C_1$-$C_6$)-alkyl,
3) —($C_2$-$C_{10}$)-alkenyl, wherein alkenyl is un-substituted or mono-, di- or trisubstituted independently of one another by halogen,
4) —($C_1$-$C_3$)-fluoroalkyl,
5) —($C_0$-$C_4$)-alkylene-O—($C_0$-$C_4$)-alkyl,
6) —($C_0$-$C_4$)-alkylene-C(O)—($C_1$-$C_4$)-alkyl,
7) —($C_0$-$C_4$)-alkylene-C(O)—O—($C_0$-$C_4$)-alkyl,
8) —($C_0$-$C_4$)-alkylene-C(O)—N(R10)-($C_0$-$C_4$)-alkyl,
9) —($C_0$-$C_4$)-alkylene-N(R10)-C(O)—($C_0$-$C_4$)-alkyl,
10) —($C_0$-$C_4$)-alkylene-S—($C_0$-$C_4$)-alkyl, or
11) —($C_0$-$C_4$)-alkylene-($C_3$-$C_8$)-cycloalkyl-($C_0$-$C_4$)-alkyl, and each of B is further unsubstituted or mono-, di- or trisubstituted independently of one another by R3, V is a monocyclic or bicyclic 3- to 15-membered heterocyclyl, wherein heterocyclyl is as defined above and is unsubstituted or mono-, di- or trisubstituted independently of one another by R14, G is 1) a covalent bond,
2) —($C_0$-$C_4$)-alkylene-C(O)—($C_0$-$C_4$)-alkylene-,
3) —($C_0$-$C_4$)-alkylene-C(O)—O—($C_0$-$C_4$)-alkylene-, or
4) —($C_0$-$C_4$)-alkylene-S—($C_0$-$C_4$)-alkylene-, M is 1) a hydrogen atom,
2) —($C_1$-$C_8$)-alkyl, wherein alkyl is unsubstituted or mono-, di- or trisubstituted independently of one another by R14,
3) —C(O)—O—R12,
4) —($C_3$-$C_8$)-cycloalkyl, wherein said cycloalkyl is unsubstituted or mono-, di- or trisubstituted independently of one another by R14,
5) phenyl, wherein phenyl is unsubstituted or mono-, di- or trisubstituted independently of one another by R14, or
6) a monocyclic or bicyclic 3- to 15-membered heterocyclyl, wherein heterocyclyl is as defined above and is unsubstituted or mono-, di- or trisubstituted independently of one another by R14, R1 is hydrogen atom,
R2 is hydrogen atom, if two —OR10 residues are attached to adjacent atoms they can form together with the atoms which they are attached to a 5- or 6-membered ring, which is unsubstituted or substituted one, two, three or four times by R13, if two —($C_1$-$C_6$)-alkyl residues are attached to adjacent atoms they can form together with the atoms which they are attached to a 5- or 6-membered cycloalkyl ring, which is unsubstituted or substituted one, two, three or four times by R13, R3 is 1) hydrogen atom,
2) halogen,
3) —($C_1$-$C_6$)-alkyl, wherein alkyl is unsubstituted or mono-, di- or trisubstituted independently of one another by R13,
4) —($C_0$-$C_4$)-alkylene-O—R19, wherein R19 is
  a) hydrogen atom,
  b) —($C_1$-$C_4$)-alkyl, wherein alkyl is unsubstituted or mono-, di- or trisubstituted independently of one another by R13,
  c) —($C_3$-$C_8$)-cycloalkyl, wherein alkyl is unsubstituted or mono-, di- or trisubstituted independently of one another by R13,
  d) phenyl, wherein phenyl is unsubstituted or mono-, di- or trisubstituted independently of one another by R13,
  e) —$CF_3$, or
  f) —$CHF_2$,
5) —($C_0$-$C_4$)-alkylene-C(O)—O—R11, or
6) —($C_0$-$C_4$)-alkylene-phenyl, wherein phenyl is mono-, di- or trisubstituted independently of one another by R13, R4 is 1) hydrogen atom,
2) —($C_0$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl, or
6) —CN,
7) —$NO_2$,
8) —S—$CH_3$, or
9) —$SO_2$—$NH_2$, R10 is hydrogen atom, —($C_1$-$C_4$)-alkyl or —($C_1$-$C_3$)-fluoroalkyl, R11 and R12 are independently of one another identical or different and are
1) hydrogen atom,
2) —($C_1$-$C_6$)-alkyl, wherein alkyl is unsubstituted or mono-, di- or trisubstituted independently of one another by R13,
3) —($C_1$-$C_3$)-fluoroalkyl, or
4) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13, or R11 and R12 form together with the nitrogen atom to which they are attached a 4-, 5-, 6-, 7- or 8-membered monocyclic heterocyclic ring selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane, and wherein said ring is unsubstituted or substituted depending on the number of ring atoms one, two, three or four times by R13, R13 is hydrogen atom, —($C_1$-$C_8$)-alkyl, —($C_3$-$C_8$)-cycloalkyl, —($C_1$-$C_8$)-alkoxy, phenyl, halogen, —C(O)—O—R10, —C(O)—N(R10)-R20, or —($C_1$-$C_3$)-fluoroalkyl, R14 is hydrogen atom, halogen, —OH, =O, —$NO_2$, —CN, —$NH_2$, —S—R18, —($C_1$-$C_8$)-alkyl, —($C_1$-$C_4$)-alkoxy, —C(O)—O—($C_1$-$C_4$)-alkyl, —($C_1$-$C_4$)-alkylene-C(O)—OH, or —($C_1$-$C_3$)-fluoroalkyl,
wherein R18 is hydrogen atom, —($C_1$-$C_3$)-fluoroalkyl or —($C_1$-$C_6$)-alkyl, and R20 is hydrogen atom, —($C_1$-$C_4$)-alkyl or —($C_1$-$C_3$)-fluoroalkyl, in all its stereoisomeric forms and mixtures thereof in any ratio, and its physiologically tolerable salts.

4) The present invention also relates to compounds of the formula I, wherein

D is 1) thiazolyl
  2) —($C_6$-$C_{14}$)-aryl, wherein aryl is selected from phenyl or naphthyl, wherein said aryl residue is unsubstituted or substituted 1 or 2 times by R4,
  3) —($C_3$-$C_6$)-cycloalkyl, or
  4) —($C_1$-$C_4$)-alkyl, Q is 1) —($C_0$-$C_4$)-alkylene-C(O)—O—($C_0$-$C_2$)-alkylene-, wherein alkylene is unsubstituted or mono- or disubstituted independently of one another by R13,
  2) —($C_1$-$C_4$)-alkylene-C(O)—N(R10)-,
  3) —($C_1$-$C_4$)-alkylene-N(R10)-,
  4) —($C_1$-$C_4$)-alkylene-N(R10)-C(O)—, or
  5) —($C_1$-$C_4$)-alkylene-N(R10)-C(O)—O—, J is 1) hydrogen atom,
  2) —($C_1$-$C_4$)-alkyl, wherein alkyl is unsubstituted or mono- or disubstituted independently of one another by R13,
  3) —($C_0$-$C_4$)-alkylene-C(O)—O—R11,
  4) —($C_0$-$C_4$)-alkylene-$SO_s$—R11, wherein s is 1 or 2,
  5) —($C_0$-$C_4$)-alkylene-($C_3$-$C_6$)-cycloalkyl, wherein cycloalkyl is unsubstituted or mono-, di- or trisubstituted independently of one another by R13, or
  6) —($C_0$-$C_4$)-alkylene-($C_3$-$C_6$)-cycloalkenyl, wherein cycloalkyl is unsubstituted or mono-, di- or trisubstituted independently of one another by R14, Z-A form a residue selected from —O—($C_1$-$C_8$)-alkylene- or —O—($C_3$-$C_8$)-cycloalkylene-, wherein said residue is bound via the oxygen atom to pyrazole residue and by the alkylene or cycloalkylene carbon atom to B, B is 1) hydrogen atom,
  2) —($C_1$-$C_6$)-alkyl,
  3) —($C_2$-$C_{10}$)-alkenyl, wherein alkenyl is un-substituted or mono-, di- or trisubstituted independently of one another by halogen,
  4) —($C_1$-$C_3$)-fluoroalkyl,
  5) —($C_0$-$C_4$)-alkylene-O—($C_0$-$C_4$)-alkyl,
  6) —($C_0$-$C_4$)-alkylene-C(O)—($C_1$-$C_4$)-alkyl,
  7) —($C_0$-$C_4$)-alkylene-C(O)—O—($C_0$-$C_4$)-alkyl,
  8) -($C_0$-$C_4$)-alkylene-C(O)—N(R10)-$C_0$-$C_4$)-alkyl,
  9) —($C_0$-$C_4$)-alkylene-N(R10)-C(O)—($C_0$-$C_4$)-alkyl,
  10) —($C_0$-$C_4$)-alkylene-S—($C_0$-$C_4$)-alkyl, or
  11) —($C_0$-$C_4$)-alkylene-($C_3$-$C_8$)-cycloalkyl-($C_0$-$C_4$)-alkyl, and each of B is further unsubstituted or mono-, di- or trisubstituted independently of one another by R3, V is heterocyclyl selected from azetidinyl, pyrrolidinyl, piperazinyl, piperidinyl, diazepanyl, imidazolidinyl or triazinanyl and wherein heterocyclyl is unsubstituted or mono-, di- or trisubstituted independently of one another by R14, G is 1) a covalent bond,
  2) —($C_0$-$C_4$)-alkylene-C(O)—,
  3) —($C_0$-$C_4$)-alkylene-C(O)—O—, or
  4) —S—, M is 1) a hydrogen atom,
  2) —($C_1$-$C_6$)-alkyl, wherein alkyl is unsubstituted or mono-, di- or trisubstituted independently of one another by R14,
  3) —C(O)—O—R12,
  4) —($C_3$-$C_8$)-cycloalkyl, wherein said cycloalkyl is unsubstituted or mono-, di- or trisubstituted independently of one another by R14,
  5) phenyl, wherein phenyl is unsubstituted or mono-, di- or trisubstituted independently of one another by R14, or
  6) a heterocyclyl selected from benzoisoxazolyl, furanyl, isoxazolyl, pyridyl, pyrimidinyl, pyrrolidinyl, tetrahydrofuranyl, thiadiazolyl or thiazolyl, wherein heterocyclyl is unsubstituted or substituted by R14, R1 is a hydrogen atom,
R2 is a hydrogen atom,
R3 is 1) hydrogen atom,
  2) halogen,
  3) —($C_1$-$C_6$)-alkyl, wherein alkyl is unsubstituted or mono-, di- or trisubstituted independently of one another by R13,
  4) —($C_0$-$C_4$)-alkylene-O—R19, wherein R19 is hydrogen atom or —($C_1$-$C_4$)-alkyl, wherein alkyl is unsubstituted or mono-, di- or trisubstituted independently of one another by R13,
  5) —($C_0$-$C_4$)-alkylene-C(O)—O—R11, or
  6) —($C_0$-$C_4$)-alkylene-phenyl, wherein phenyl is mono-, di- or trisubstituted independently of one another by R13, R4 is 1) hydrogen atom,
  2) —($C_0$-$C_6$)-alkyl, wherein alkyl is unsubstituted or mono-, di- or trisubstituted independently of one another by R13,
  3) —($C_0$-$C_4$)-alkylene-O—R10,
  4) halogen,
  5) —($C_1$-$C_3$)-fluoroalkyl, or
  6) —CN,
  7) —$NO_2$,
  8) —S—$CH_3$, or
  9) —$SO_2$—$NH_2$, R10 is hydrogen atom, —($C_1$-$C_4$)-alkyl or —($C_1$-$C_3$)-fluoroalkyl, R11 and R12 are independently of one another identical or different and are
1) hydrogen atom,
2) —$(C_1$-$C_6)$-alkyl, wherein alkyl is unsubstituted or mono-, di- or trisubstituted independently of one another by R13,
3) —$(C_1$-$C_3)$-fluoroalkyl, or
4) —$(C_0$-$C_6)$-alkylene-$(C_3$-$C_8)$-cycloalkyl, wherein alkylene and cycloalkyl independently from one another are unsubstituted or mono-, di- or trisubstituted independently of one another by R13, or R11 and R12 form together with the nitrogen atom to which they are attached a heterocyclic ring selected from azetidine, piperidine or pyrrolidine, and wherein said ring is unsubstituted or substituted one, two or three times by R13, R13 is hydrogen atom, —$(C_1$-$C_8)$-alkyl, —$(C_3$-$C_8)$-cycloalkyl, —$(C_1$-$C_8)$-alkoxy, phenyl, halogen, —C(O)—O—R10, —C(O)—N(R10)-R20, or —$(C_1$-$C_3)$-fluoroalkyl, R14 is hydrogen atom, halogen, —OH, =O, —$NO_2$, —CN, —$NH_2$, —S—R18, —$(C_1$-$C_8)$-alkyl, —$(C_1$-$C_4)$-alkoxy, —C(O)—O—$(C_1$-$C_4)$-alkyl, —$(C_1$-$C_4)$-alkylene-C(O)—OH, or —$(C_1$-$C_3)$-fluoroalkyl,
wherein R18 is hydrogen atom, —$(C_1$-$C_3)$-fluoroalkyl or —$(C_1$-$C_6)$-alkyl, and R20 is hydrogen atom or —$(C_1$-$C_4)$-alkyl,
in all its stereoisomeric forms and mixtures thereof in any ratio, and its physiologically tolerable salts.

As used herein, the term alkyl is a hydrocarbon residue, which can be linear, e.g. straight-chain, or branched. Examples of "—$(C_1$-$C_8)$-alkyl" or "—$(C_1$-$C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, hexylene, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, secondary-butyl, tertiary-butyl, tertiary-pentyl, secondary-butyl. The terms "—$(C_0$-$C_8)$-alkyl" or "—$(C_0$-$C_8)$-alkylene" are each hydrocarbon residues containing 1, 2, 3, 4, 5, 6, 7 or 8 carbon atoms as defined for —$(C_1$-$C_8)$-alkyl or —$(C_1$-$C_8)$-alkylene and the terms "—$C_0$-alkyl" or "—$C_0$-alkylene" are understood as meaning each a covalent bond. The terms "—$(C_2$-$C_{10})$-alkenyl" or "—$(C_2$-$C_{10})$-alkenylene" are understood as meaning alkyl residues containing 2, 3, 4, 5, 6, 7, 8, 9 or 10 carbon atoms are, wherein said alkyl residues depending on the chain length contain 1, 2 or 3 double bonds. Examples of such residues are residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

The terms "—$(C_2$-$C_{10})$-alkynyl" or "—$(C_2$-$C_{10})$-alkynylene" are understood as meaning alkyl residues containing 2, 3, 4, 5, 6, 7, 8, 9 or 10 carbon atoms are, wherein said alkyl residues depending on the chain length contain 1, 2 or 3 triple bonds, such as ethynyl, 1-propynyl, 2-propynyl (=propargyl) or 2-butynyl.

The term "—$(C_3$-$C_8)$-cycloalkyl" is understood as meaning cycloalkyl residues containing 3, 4, 5, 6, 7 or 8 ring carbon atoms like cyclopropyl, cyclobutyl, cyclopentyl, cyclohexyl, cyloheptyl or cyclooctyl.

The term "—$(C_3$-$C_7)$-cycloalkenyl" is understood as meaning cycloalkyl residues having one double bond and containing 3, 4, 5, 6 or 7 ring carbon atoms like cyclopropenyl, cyclobutenyl, cyclopentenyl, cyclohexenyl or cycloheptenyl or cyclooctyl.

The terms "6- to 14-membered aryl" or "—$(C_6$-$C_{14})$-aryl" are understood as meaning a mono- or bicyclic-aromatic hydrocarbon radicals containing from 6 to 14 carbon atoms in the ring. Examples are phenyl, naphthyl, for example 1-naphthyl and 2-naphthyl, biphenylyl, for example 2-biphenylyl, 3-biphenylyl and 4-biphenylyl, indanyl, anthryl or fluorenyl. Biphenylyl radicals, naphthyl radicals and, in particular, phenyl radicals are preferred aryl radicals.

The term "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxa-thiepane, 1,2-oxathiolane, 1,4-oxazepane, 1,2-oxazine, 1,3-oxazine, 1,4-oxazine, oxazolone, oxazole, [1,3,4]oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole or 1,2,4-triazole.

The term "mono- bi- or tricyclic 4- to 15-membered heteroaryl" or "—$(C_4$-$C_{15})$-heteroaryl" refers to an aromatic $(C_4$-$C_{15})$-aryl ring system in which one or more of the 4 to 15 ring carbon atoms are replaced by heteroatoms such as nitrogen, oxygen or sulfur. Examples are azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, β-carbolinyl, carbazolyl, 4aH-carbazolyl, chromanyl, chromenyl, cinnolinyl, furyl, fuarzanyl, imidazolyl, 1H-indazolyl, indolizinyl, indolyl, isobenzofuranyl, isochromanyl, isoindazolyl, isoindolyl, isoquinolinyl isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyrazolyl, pyridazinyl, pryidooxazole, pyridoimidazole, pyridothiazole, pyridinyl, pyridyl, pyrimidinyl, pyrrolyl, quinazolinyl, quinolinyl, quinoxalinyl, quinuclidinyl, tetrahydrofuranyl, 1,2,3-thiadiazolyl, 1,2,4-thiadiazolyl, 1,2,5-thiadiazolyl, 1,3,4-thiadiazolyl, thiazolyl, thienyl, tetrazolyl and xanthenyl.

The terms "mono- or bicyclic 3- to 15-membered heterocyclyl" or "—$(C_3$-$C_{15})$-heterocyclyl" refers to heterocycles wherein one or more of the 3 to 15 ring carbon atoms are replaced by heteroatoms such as nitrogen, oxygen or sulfur such as acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, azaspirohexanyl, aza-spirooctanyl, aza-spiropentanyl, azepinyl, azetidinyl, aziridinyl, benzofuranyl, benzoimidazolyl, benzoisothiazolyl, benzoisoxazolyl, benzotetrazolyl, benzothiazolyl, benzothiofuranyl, benzothiophenyl, benzotriazolyl, benzoxazolyl, carbazolyl, 4aH-carbazolyl, carbolinyl, chromanyl, chromenyl, cinnolinyl, decahydro-quinolinyl, diazabicyclohexanyl, diaza-bicycloheptanyl, 2,5-diaza-bicyclo[2.2.1]heptanyl, 1,2-diazapanyl, diaza-spirohexanyl, diazaspirooctanyl, diaza-spiropentanyl, diaza-spiroheptanyl, 1,3- diazepanyl, 1,4-diazepanyl, 1,2-diazepinyl, 1,3-diazepinyl, 1,4-diazepinyl, dihydroazepinyl, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, dioxazolyl, dioxazinyl, 1,3-dioxolanyl, 1,3-dioxolenyl, 3,3-dioxo[1,3,4]oxathiazinyl, 6H-1,5,2-dithiazinyl, furyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydroisoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl.

The term "R11 and R12 together with the nitrogen atom to which they are bonded can form a 4-, 5-, 6-, 7- or 8-membered monocyclic heterocyclic ring which in addition to the nitrogen atom can contain one or two identical or different ring heteroatoms chosen from oxygen, sulfur and nitrogen" refer to structures of heterocycles such as aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane.

The term "—$(C_1$-$C_3)$-fluoroalkyl" is a partial or totally fluorinated alkyl-residue consisting of 1 to 3 carbon atoms, which can be derived from residues such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—$(C_1$-$C_3)$-fluoroalkylene" is a partial or totally fluorinated alkylene-residue, residue consisting of 1 to 3 carbon atoms, which can be derived from residues such as —$CF_2$—, —CHF—, —CHF—$CHF_2$—, —CHF—CHF—, —$CH_2$—$CF_2$—, —$CH_2$—CHF—, —$CF_2$—$CF_2$—, —$CF_2$—CHF—, —$CH_2$—CHF—$CF_2$—, —$CH_2$—CHF—CHF—, —$CH_2$—$CH_2$—$CF_2$—, —$CH_2$—$CH_2$—CHF, —$CH_2$—$CF_2$—$CF_2$—, —$CH_2$—$CF_2$—CHF—, —CHF—CHF—$CF_2$—, —CHF—CHF—CHF—, —CHF—$CH_2$—$CF_2$—, —CHF—$CH_2$—CHF—, —CHF—$CF_2$—$CF_2$—, —CHF—$CF_2$—CHF—, —$CF_2$—CHF—$CF_2$—, —$CF_2$—CHF—CHF—, —$CF_2$—$CH_2$—$CF_2$—, —$CF_2$—$CH_2$—CHF—, —$CF_2$—$CF_2$—$CF_2$—, or —$CF_2$—$CF_2$—CHF.

The term "if two —$(C_1$-$C_6)$-alkyl residues are attached to adjacent atoms they can form together with the atoms which they are attached to a 5- or 6-membered cycloalkyl ring" refers to residues such as cyclopentyl and cyclohexyl.

The term "if two —OR10 residues are attached to adjacent atoms they can form together with the atoms which they are attached to a 5- or 6-membered ring" refers to structures such as 1,3-dioxole ring and 2,3-dihydro-[1,4]dioxine ring.

The term "=O" refers to residues such as carbonyl (—C(O)—) or nitroso (—N=O). Halogen is fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example a guanidino group and a carboxyl group, can also be present as zwitterions (betaines) which are likewise included in the present invention.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I, which can be converted into compounds of the formula I under physiological conditions. Suitable prodrugs for the compounds of the formula I, i.e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443; or Hydrolysis in Drug and Prodrug Metabolism, B. Testa, J. M. Mayer, Wiley-VCH, 2003, which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogen atoms on nitrogen atoms in such groups are replaced with an acyl group or a carbamate, preferably a —(C1-C6)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1-C_{18})$-alkyl, $(C_3-C_8)$-cycloalkyl, $(C_3-C_8)$-cycloalkyl-$(C_1-C_4)$-alkyl-, $(C_6-C_{14})$-aryl, het-, $(C_6-C_{14})$-aryl-$(C_1-C_4)$-alkyl- or het-$(C_1-C_4)$-alkyl- and in which $R^{p2}$ has the meanings indicated for $R^{p1}$ with the exception of hydrogen.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I, all residues that are present more than one time in the molecule are independent of each other and can be identical or different.

The compounds of the formula I can be prepared by utilizing procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formula I can be prepared, for example in the course of a convergent synthesis, by linking two or more fragments which can be derived retrosynthetically from the formula I. More specifically, suitably substituted starting pyrazole derivatives are employed as building blocks in the preparation of the compounds of formula I. If not commercially available, such pyrazole derivatives can be prepared according to the well-known standard procedures for the formation of the pyrazole ring system. By choosing suitable precursor molecules, these pyrazole syntheses allow the introduction of a variety of substituents into the various positions of the pyrazole system, which can be chemically modified in order to finally arrive at the molecule of the formula I having the desired substituent pattern. As one of the comprehensive reviews in which numerous details and literature references on the chemistry of pyrazole and on synthetic procedures for their preparation can be found J. Eiguero in "Comprehensive Heterocyclic Chemistry II"; Eds. A. Katritzky, Ch. Rees, E. Scriven; Elsevier 1996, Vol. 3; K. Kirschke in Houben-Weyl, "Methoden der Organischen Chemie" (Methods of Organic Chemistry), Georg Thieme Verlag, Stuttgart, Germany 1994, Vol. E8b Hetarene; T. Nagai et al. Org. Prep. Proced. Int. (1993), 25, 403; M. Elnagdi et al. Heterocycles (1985) 23, 3121; K. Makino et al. J. Heterocycl. Chem. (1998) 35, 489; K. Makino et al. J. Heteterocycl. Chem. (1999) 36, 321.

If starting pyrazole derivatives are not commercially available and have to be synthesized this can be done, for example, according to the well-known pyrazole syntheses mentioned above. In the following procedures of particular interest for the embodiment of this invention are listed and referenced briefly, however, they are standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modern separation techniques like, for example, preparative HPLC.
1) N. Kudo et al. Chem. Pharm. Bull. (1999) 47, 857.
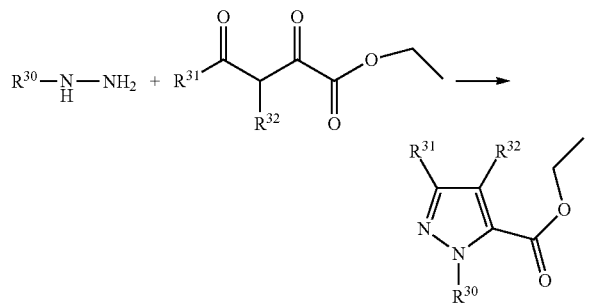
2) A. Padwa, J. Heterocycl. Chem. (1987) 24, 1225.
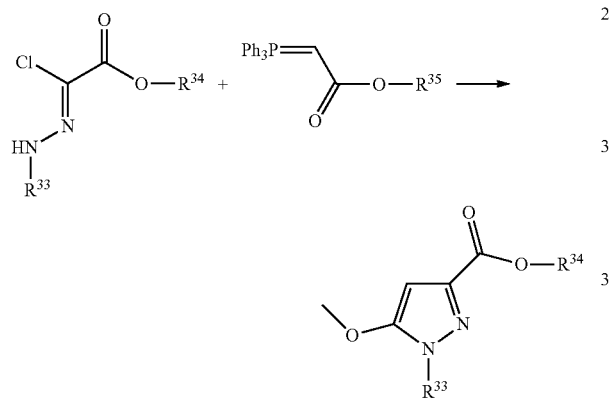
3) N. K. Markova et al., Zh. Org. Khim. (1983) 19, 2281.
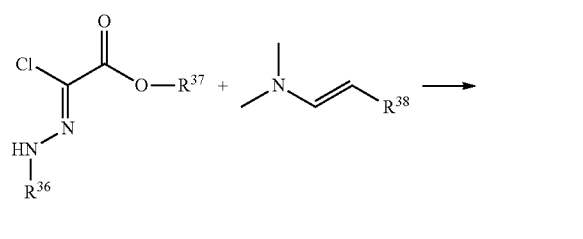
4) P. Bravo et al., Tetrahedron (1994) 50, 8827.
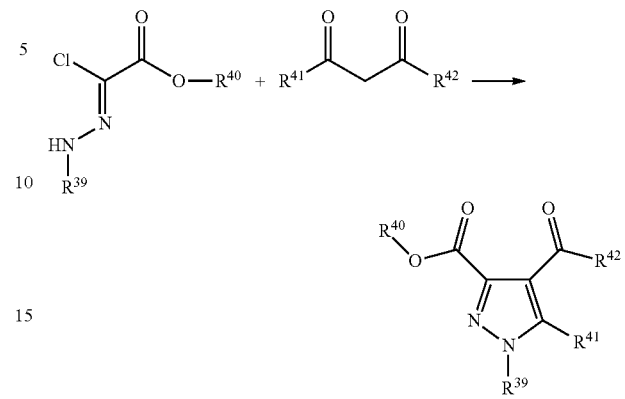
5) M. A. Martins et al., Synthesis (1995) 12, 1491.
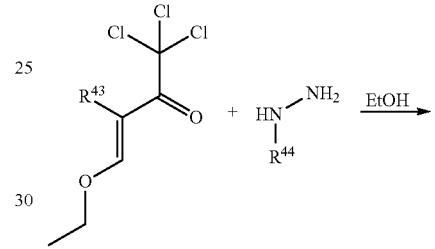
6) R. G. Jones et al., J. Org. Chem. (1955) 20, 1342.
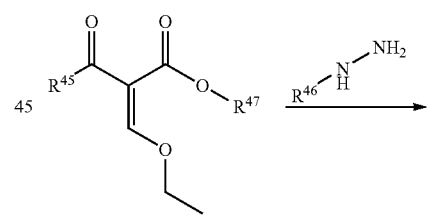
7) W. T. Ashton et al., J. Heterocycl. Chem. (1993) 30, 307.
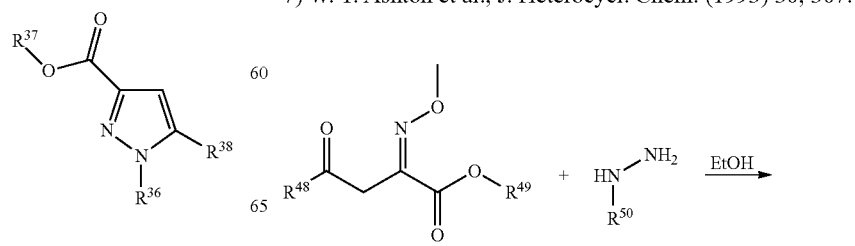

-continued
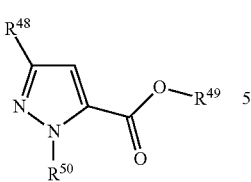
8) K. I. Bookermilburn, Synlett, (1992) 327.
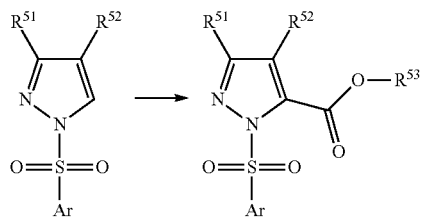
9) F. Farina et al., Heterocycles (1989) 29, 967.
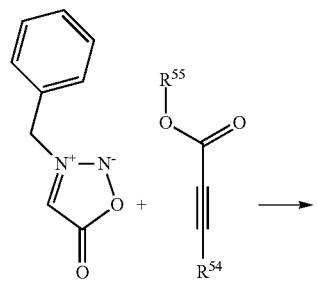
10) T. Hague et al., J. Med. Chem. (2002) 4669.
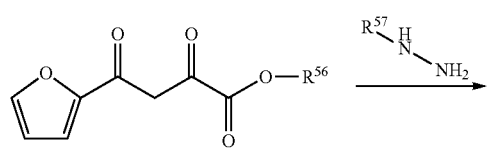
-continued
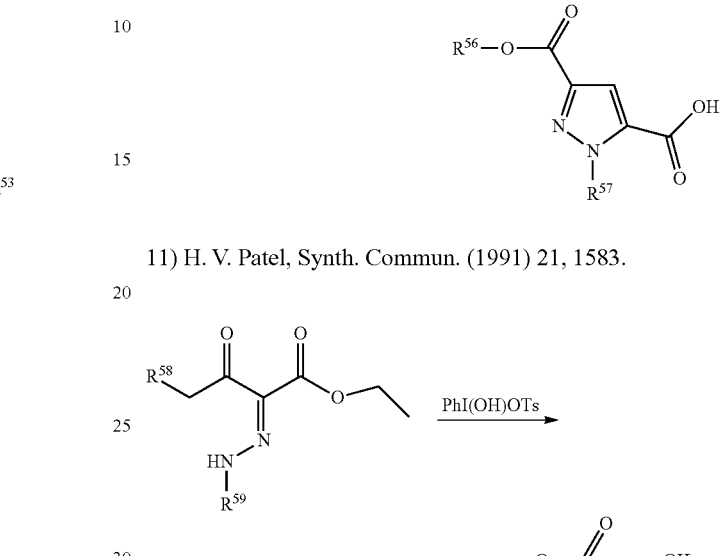
11) H. V. Patel, Synth. Commun. (1991) 21, 1583.
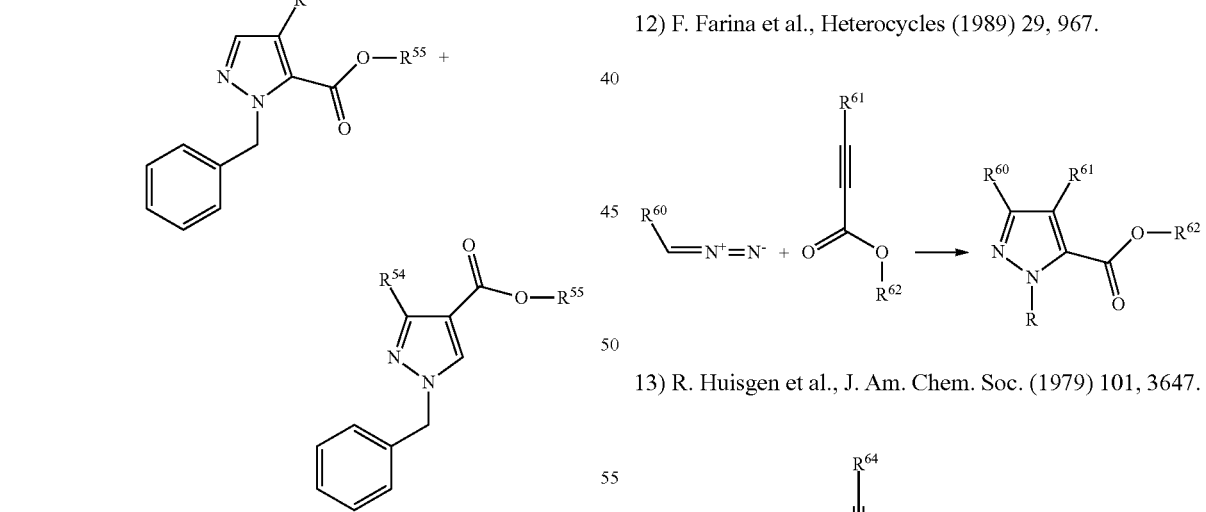
12) F. Farina et al., Heterocycles (1989) 29, 967.
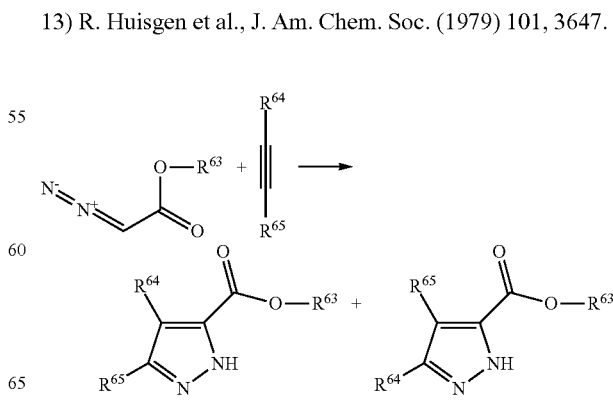
13) R. Huisgen et al., J. Am. Chem. Soc. (1979) 101, 3647.

14) W. Sucrow et al., Angew. Chem., Int. Ed. (1975) 14, 560.
15) C. Baldoli et al., J. Heterocycl. Chem. (1989), 26, 241.
16) G. M. Pilling et al., Tetrahedron Lett. (1988) 29, 1341.
17) D. Sauer et al., J. Org. Chem. (1990) 55, 5535.
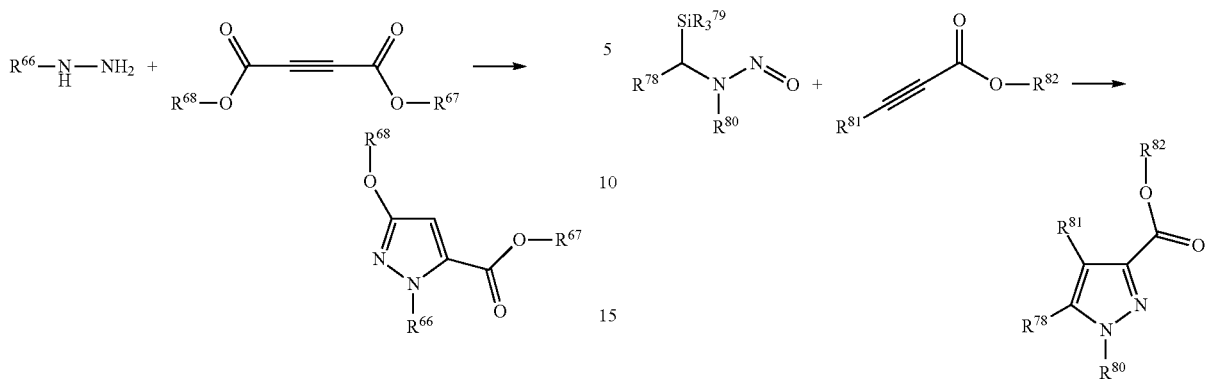
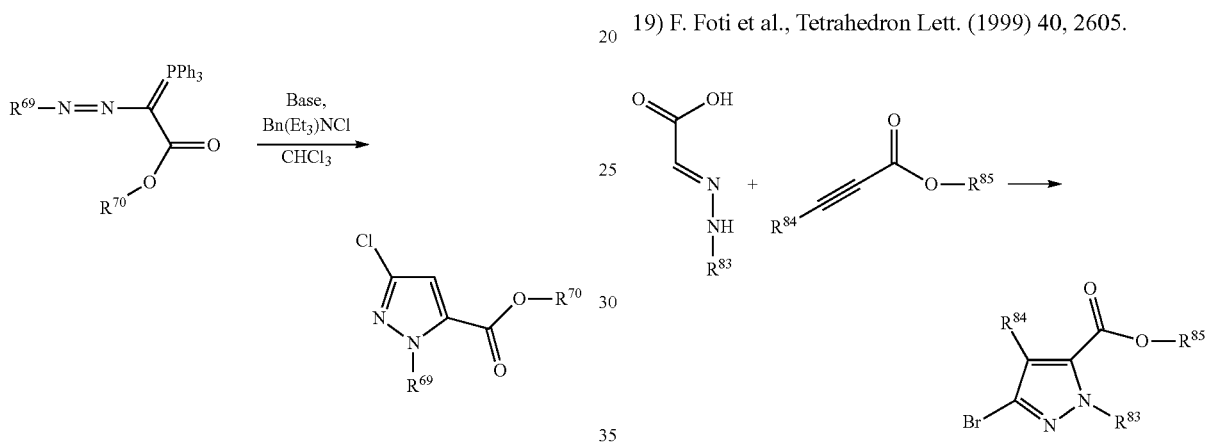
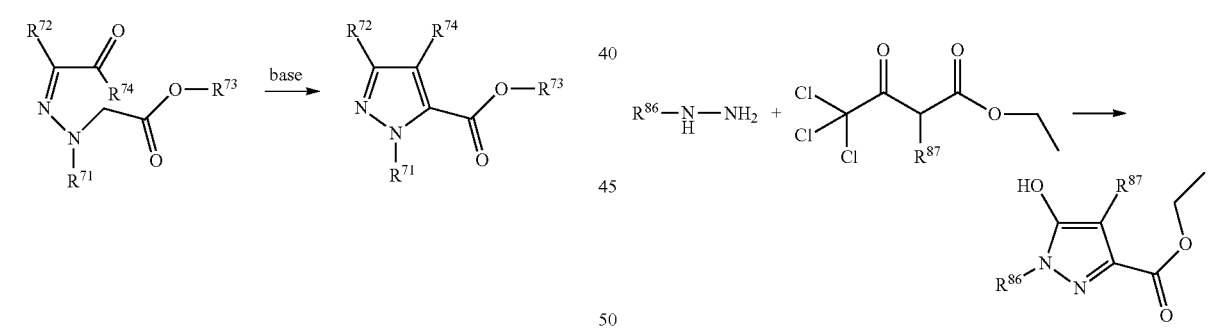
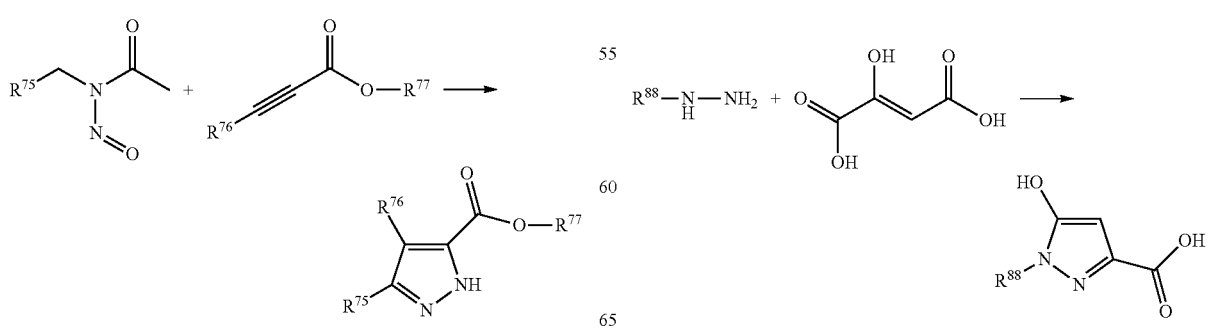
18) K. Washizuka et al., Tetrahedron Lett. (1999) 40, 8849.
19) F. Foti et al., Tetrahedron Lett. (1999) 40, 2605.
20) M. Martins et al., Synthesis (2003) 15, 2353.
21) J. Nef, Liebigs Ann. Chem. (1893) 276, 231.

22) Leighton, J. Am. Chem. Soc. (1898) 20, 677.

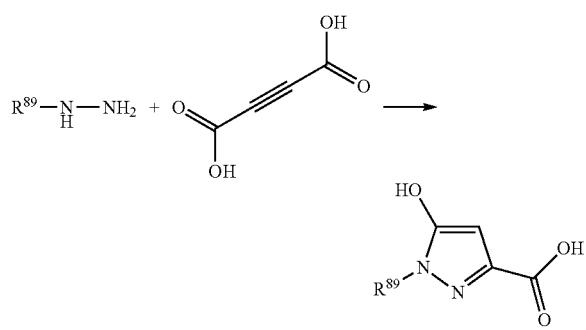

23) H. Ochi et al., Chem. Pham. Bull. (1983) 31, 1228.

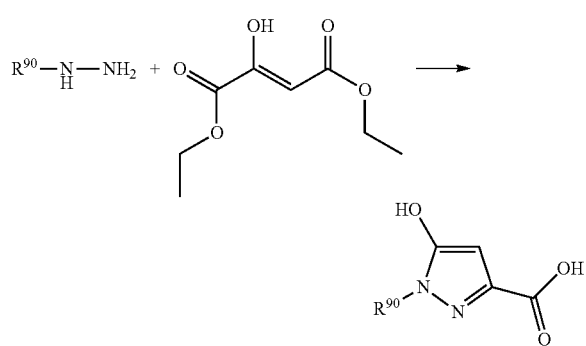

Depending on the substituents in the starting materials, in certain pyrazole syntheses mixtures of positional isomers may be obtained, which, however, can be separated by modern separation techniques like, for example, preparative HPLC.

Further, in order to obtain the desired substituents at the pyrazole ring system in the formula I, the functional groups introduced into the ring system during the pyrazole synthesis can be chemically modified. Especially the substituents present on the pyrazole ring system can be modified by a variety of reactions and thus the desired residues can be obtained. For example, a pyrazole carrying a hydrogen atom in the 4-position can also be obtained by saponification and subsequent decarboxylation of pyrazole carrying an ester group in the relevant position. In addition, carboxylic acid groups and acetic acid groups in the 3-position, the 4-position and the 5-position can be converted into their homologues by usual reactions for chain elongation of carboxylic acids. Halogen atoms can be introduced into the 3-position, the 4-position and the 5-position, for example according to procedures like the following described in the literature. For the fluorination of pyrazoles N-fluoro-2,4,6-trimethylpyridinium triflate is the reagent of choice (T. Umemoto, S. Fukami, G. Tomizawa, K. Harasawa, K. Kawada, K. Tomita, J. Am. Chem. Soc. (1990) 112, 8563 see also K. Manko et al., J. Fluorine Chem. (1988) 39, 435; R. Storer et al. Nucleosides Nucleotides (1999) 18; 203). However, other suitable fluorinating reagents may also be employed where appropriate. The chlorination, bromination, or iodination of pyrazoles can be accomplished by the reaction with elemental halogens or by the use of NCS, NBS or NIS and many other reagents well known to those skilled in the art. In addition suitable procedures are for example reported by M. Rodriguez-Franco et al., Tetrahedron Lett. (2001) 42, 863; J. Pawlas et al., J. Org. Chem. (2000) 65, 9001; Y. Huang et al., Org Lett (2000) 2, 2833; W. Holzer et al., J. Heterocycl. Chem. (1995) 32, 1351; N. Kudo et al., Chem. Pharm. Bull. (1999) 47, 857; G. Auzzi et al., Farmaco, Ed Sci (1979) 34, 743; K. Morimoto et al., J. Heterocycl. Chem. (1997) 34, 537; D. Jeon et al., Synth. Commun. (1998) 28, 2159.

Depending on the reaction conditions, reagent, stochiometry and substitution pattern the halogen is introduced in the 3-position and/or 4-position and/or 5-position. By selective halogen/metal exchange or metalation by selective hydrogen/metal exchange and subsequent reaction with a wide range of electrophiles various substituents can be introduced at the heterocyclic nucleus. (M. R. Grimmett, Heterocycles (1994) 37, 2087; V. D. Gardner et al., J. Heterocycl. Chem. (1984), 21, 121; D. Butler et al., J. Org. Chem. (1971) 36, 2542). Among others the corresponding pyrazolones can be useful precursors for the introduction of halogen atoms. For example a 1H-pyrazol-3-ol can be converted to 5-chloro-1H-pyrazole by using for example phosphorous oxychloride. The 5-bromo-1H-pyrazole can be obtained from 1H-pyrazol-3-ol by similar standard procedures using phosphorous oxybromide, phosphorous tribromide or phosphorous pentabromide. Halogens, hydroxy groups (via the triflate or nonaflate) or primary amines (via the diazonium salt) or after interconversion to the corresponding stannane, or boronic acid—present in the pyrazole structure can be converted into a variety of other functional groups like for example —CN, —CF$_3$, —C$_2$F$_5$, ethers, acids, amides, amines, alkyl- or aryl-groups mediated by means of transition metals, such as palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem., 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. I 1997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108; A. F. Littke, G. F. Fu, Angew. Chem. Int. Ed. 2002, 41, 4176-4211; A. R. Muci, S. L. Buchwald, Topics in Current Chemistry 2002, 219, 131-209.

For example, nitro groups can be reduced to amino groups with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce these residues, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the pyrazole nucleus can be hydrolyzed to the corresponding carboxylic acids, which after activation can then be reacted with amines or alcohols under standard conditions. Furthermore these ester or acid groups can be reduced to the corresponding alcohols by many standard procedures. Ether groups present at the pyrazole, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{100}$ or $R^{102}$ attached to the pyrazole ring system by application of parallel synthesis methodology, beside a variety of reactions, palladium, nickel or copper catalysis can be extremely useful. Such reactions are described for example in F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; P. Lam, C. Clark, S. Saubern, J. Adams, M. Winters, D. Chan, A. Combs, Tetrahedron Lett. 1998, 39, 2941; D. Chan, K. Monaco, R. Wang, M. Winters, Tetrahedron Lett. 1998, 39, 2933; J. Wolfe, H. Tomori, J. Sadight, J. Yin, S. Buchwald, J. Org. Chem. 2000, 65, 1158; V. Farina, V. Krishnamurthy, W. Scott, The Stille Reaction, Wiley, 1994; S. Buchwald et al., J. Am. Chem. Soc. 2001, 123, 7727; S. Kang et al., Synlett 2002, 3, 427; S. Buchwald et al., Org. Lett. 2002, 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to a pyrazole ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art.

The structural elements present in the residues at the 5-position of the pyrazole ring in the compounds of the formula I and in the $COR^{102}$ group present in the 3-position of the pyrazole ring can be introduced into the starting pyrazole derivative using the methods outlined above by consecutive reaction steps using parallel synthesis methodologies like those outlined below using procedures which per se are well known to one skilled in the art.

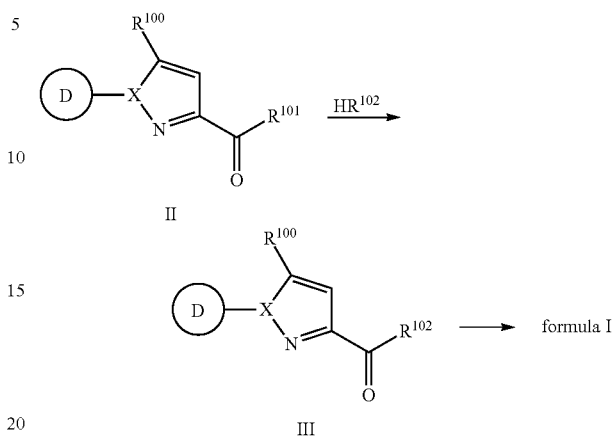

The residues $R^{102}$ can be introduced in compounds of the formula II, for example, by condensing a corresponding carboxylic acid of the formula II with a compound of the formula $HR^{102}$, whereby $HR^{102}$ is an amine of the formula IV, to give a compound of the formula III.

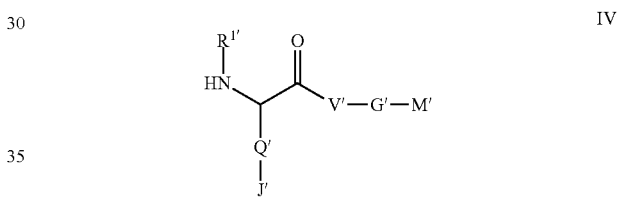

The compound of the formula III thus obtained can already contain the desired final groups, i.e. the groups $R^{102}$ and $R^{100}$ can be the groups of the formulae V and VI, respectively, as defined in formula I, or optionally in the compound of the formula III thus obtained the residue $R^{102}$ or the residues $R^{102}$ and $R^{100}$ are subsequently converted into the residues of the formulae V and VI, respectively, to give the desired compound of the formula I.

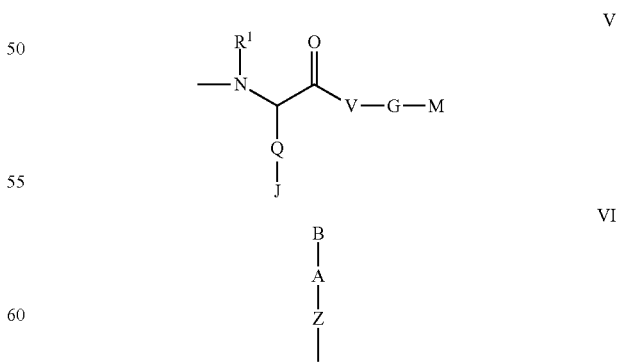

Thus, the residues $R^{102}$ and the residues V', G', Q', J' and M' contained in formula IV can have the denotations of residues of the formula V, respectively, given above or in addition in the residues of the formula IV functional groups can also be present in the form of groups that can subsequently be transformed into the final groups of the formula V, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Examples of precursor groups are cyano groups and nitro groups. The cyano group can, in a later step, be transformed into carboxylic acid derivatives or by reduction into aminomethyl groups. Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA or other acids at a later stage of the synthesis.

The residue $R^{100}$ in the compounds of the formulae II and III can denote the group of formula VI as defined above which finally is to be present in the desired target molecule of the formula I, or it can denote a group which can subsequently be transformed into the group of formula VI, for example a precursor group or a derivative of the group of formula VI in which functional groups are present in protected form, or $R^{100}$ can denote a hydrogen, a oxygen atom, or a nitrogen, or a sulfur atom or a protective group masking the aforementioned atoms of the pyrazole ring.

The residue $R^{101}$ in the compounds of the formula II which can be identical or different, can be, for example, hydroxy or $(C_1-C_4)$-alkoxy, i.e., the groups $COR^{101}$ present in the compounds of the formula II can be, for example, the free carboxylic acids or esters thereof like alkyl esters as can be the groups $COR^{102}$ in the compounds of the formula III. The groups $COR^{101}$ can also be any other activated derivative of a carboxylic acid which allows amide formation with a compound of the formula $HR^{102}$. The group $COR^{101}$ can be, for example, an acid chloride, an activated ester like a substituted phenyl ester or thioester, an azolide like an imidazolide, an azide or a mixed anhydride, for example a mixed anhydride with a carbonic acid ester or with a sulfonic acid. These derivatives can all be prepared from the carboxylic acid by standard procedures and can be reacted with an amine of the formula $HR^{102}$ under standard conditions. A carboxylic acid group COOH representing $COR^{101}$ in a compound of the formula II can be obtained, for example by standard hydrolysis procedures, from an ester group introduced into the pyrazole system during a pyrazole synthesis.

Compounds of the formula I in which a group $COR^{102}$ is an amide group can be prepared from amines and compounds of the formula II in which $COR^{101}$ is a carboxylic acid group or an ester or thioester thereof by common amination reactions. Especially for the preparation of amides the compounds of the formula II in which $COR^{101}$ is a carboxylic acid group can be condensed under standard conditions with compounds of the formula $HR^{102}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), bromo-tris-pyrrolidino-phosphonium hexafluorophosphate (Pybrop) and many others.

The activation of the carboxylic acid function may also favourably be carried out, for example, by conversion of the carboxylic acid group into the pentafluorophenyl ester using dicyclohexylcarbodiimide and pentafluorophenol or by using reagents like pentafluorophenyl trifluoroacetate, tert-butyl pentafluorophenyl carbonate, bis(pentafluorophenyl)carbonate, 2,3,4,5,6-pentafluorophenyl 4-methylbenzenesulfonate, pentafluorophenol-tetramethyluronium hexafluorophosphate, octafluoroacetophenone.

The activation of the carboxylic function by conversion to other phenylesters like for example 4-nitro-phenyl esters or 2-nitro-phenyl esters can be also effective. The activation and the subsequent reaction with a group of the formula IX are usually carried out in the presence of an inert solvent or diluent, for example DCM, chloroform, THF, diethyl ether, n-heptane, n-hexane, n-pentane, cyclohexane, diisopropyl ether, methyl tBu ether, acetonitrile, DMF, DMA, NMP, DMSO, dioxane, toluene, benzene, ethyl acetate or a mixture of these solvents, if appropriate with addition of a base such as, for example, potassium tert-butoxide or tributylamine or triethylamine or diisopropylethylamine or N-ethylmorpholine.

VII

If the residue of the formula VI present in a pyrazole of the formula I or the residue $R^{100}$ present in a pyrazole of the formula II or formula III, or a residue in which functional groups within the residue of the formula VI or $R^{100}$ are present in protected form or in the form of a precursor group, have not already been introduced during a preceding step, for example during a synthesis of the pyrazole nucleus, these residues can, for example, be introduced into the 5-position of the pyrazole system by standard alkylation procedures well-known to one skilled in the art. The starting pyrazole derivative that is to be employed in such a reaction carries an oxygen, or a nitrogen, or a sulfur atom in the 5-position. Alkylation of the aforementioned atom can, for example, be performed under standard conditions, preferably in the presence of a base like $K_2CO_3$, $Cs_2CO_3$, NaH or KO$^t$Bu, using an alkylating compound of the formula VII or of the formula $R^{100}$-LG, wherein the atom in the group A' of the formula VII or in the group $R^{100}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. These standard procedures are for example described in treatises like M.

Smith, J. March, March's Advanced Organic Chemistry, Wiley-VCH, 2001; Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991. LG may, for example, also be a hydroxy group which, in order to achieve the alkylation reaction, is activated under the well-known conditions of the Mitsunobu procedure (O. Mitsunobu, Synthesis 1981, 1) or by further modified procedures (A. Tunoori, D. Dutta, G. Gunda, Tetrahedron Lett. 39 (1998) 8751; J. Pelletier, S. Kincaid, Tetrahedron Lett. 41 (2000) 797; D. L. Hughes, R. A. Reamer, J. J. Bergan, E. J. J. Grabowski, J. Am. Chem. Soc. 110 (1998) 6487; D. J. Camp, I. D. Jenkins, J. Org. Chem. 54 (1989) 3045; D. Crich, H. Dyker, R. J. Harris, J. Org. Chem. 54 (1989) 257) of even greater use.

The residue of the formula VI present in a pyrazole of the formula I or the residue $R^{100}$ present in a pyrazole of the formula II, or a residue in which functional groups within the residue of the formula VI or $R^{100}$ are present in protected form or in the form of a precursor group, can be for example introduced into the 5-position of the pyrazole system by conventional literature procedures for the amination, etherification or thioetherification of pyrazoles well-known to those skilled in the art. The appropriately substituted pyrazole useful for these reactions carries a leaving group in the 5-position of the pyrazole like for example halogen, triflate, nonaflate, tosylate, azide, or a diazonium salt. Preferably the reaction is carried out in the presence of a base like $K_2CO_3$, $Cs_2CO_3$, NaH or KO$^t$Bu. The desired transformation can also be accomplished with halogens, hydroxy groups (via the triflate or nonaflate) or primary amines (via the diazonium salt) or after interconversion to the corresponding stannane, or boronic acid—present in the 5-position of pyrazole structure—can be converted into a variety of other functional groups like for example —CN, —$CF_3$, —$C_2F_5$, ethers, acids, amides, amines, alkyl- or aryl-groups mediated by means of transition metals, such as palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem., 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. I 1997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108.). A. F. Littke, G. F. Fu, Angew. Chem. Int. Ed. 2002, 41, 4176-4211; A. R. Muci, S. L. Buchwald, Topics in Current Chemistry 2002, 219, 131-209.

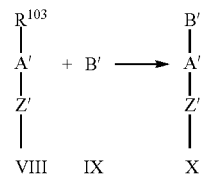

The residues $R^{103}$ in the compounds of the formula VIII which can be identical or different, can be, for example, hydroxy or ($C_1$-$C_4$)-alkoxy, i.e., the groups present in the residues of the formula VIII can be, for example, the free carboxylic acid group or esters thereof like alkyl esters. These groups can also be any other activated derivative of a carboxylic acid group which allows amide bond formation with a compound of the formula IX. The group A'—$R^{103}$ can be, for example, an acyl chloride, an activated ester like a substituted phenyl ester, an azolide like an imidazolide, an acyl azide or a mixed anhydride, for example a mixed anhydride with a carbonic acid ester or with a sulfonic acid. These derivatives can all be prepared from the carboxylic acid group by standard procedures and can be reacted with an amine of the formula IX under standard conditions. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others. O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), bromo-tris-pyrrolidino-phosphonium hexafluorophosphate (Pybrop). The activation of the carboxylic acid function may also favourably be carried, for example, by conversion of the carboxylic acid group into the pentafluorophenyl ester using dicyclohexylcarbodiimide and pentafluorophenol or by using reagents like pentafluorophenyl trifluoroacetate, tert-butyl pentafluorophenyl carbonate, bis(pentafluorophenyl)carbonate, 2,3,4,5,6-pentafluorophenyl 4-methylbenzenesulfonate, pentafluorophenol-tetramethyluronium hexafluorophosphate, octafluoroacetophenone. The activation of the carboxylic function by conversion to other phenylesters like for example 4-nitro-phenyl esters or 2-nitro-phenyl esters can be also effective. The activation and the subsequent reaction with the compound of the formula IX are usually carried in the presence of an inert solvent or diluent, for example DCM, chloroform, THF, diethyl ether, n-heptane, n-hexane, n-pentane, cyclohexane, diisopropyl ether, methyl tBu ether, acetonitrile, DMF, DMA, NMP, DMSO, dioxane, toluene, benzene, ethyl acetate or a mixture of these solvents, if appropriate with addition of a base such as, for example, potassium tert-butoxide or tributylamine or triethylamine or diisopropylethylamine or N-ethylmorpholine. A carboxylic acid group —COOH representing A'-$R^{103}$ in a residue of the formula VIII can be obtained, for example, from an ester group introduced into the pyrazole system during a pyrazole synthesis by standard deprotection procedures like hydrolysis or hydrogenation. For the formation of an amide bond with residues of the formula VIII in which A'—$R^{103}$ is a carboxylic acid group can be condensed under standard conditions with compounds of the formula IX which are amines by means of common coupling reagents used in peptide synthesis.

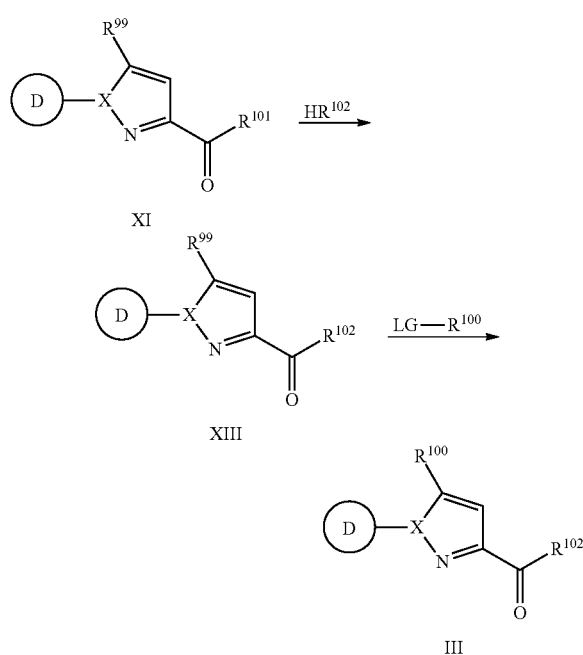

The residues of the formulae VII, VIII, IX and X thus obtained can already contain the desired final groups, i.e. the groups Z', A', B', V, G' and M' can be the groups of the formulae V and VI as defined in the formula I, or optionally in the compound of the formula III thus obtained subsequently the residue or the residues $R^{102}$ and $R^{100}$ are converted into the residues of the formulae V and VI, respectively, to give the desired compound of the formula I. Thus, the residues of the formulae VII, VIII, IX and X contained therein can have the denotations of residues of the formulae V and VI, respectively, given above or in addition in the residues of the formulae VII, VIII, IX and X can also be present in the form of groups that can subsequently be transformed into the final groups of the formulae V and VI, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000).

During the above-mentioned transformations positional isomers may occur, nevertheless these mixtures of positional isomers can be separated by modern separation techniques like, for example, preparative HPLC.

The compounds of the present invention are platelet ADP P2Y12 receptor antagonists, which antagonize the platelet aggregating effect of the activation of the platelet ADP P2Y12 receptors. In particular, they are highly active antagonists of the P2Y12 receptor. They are specific platelet ADP receptor antagonists inasmuch as they do not substantially inhibit or promote the activity of other receptors whose activation or inhibition is not desired. The activity of the compounds of the formula I can be determined, for example, in the assays described below or in other in vitro, ex vivo or in vivo assays known to those skilled in the art. For example, the ability of the compounds to bind to the P2Y12 receptor may be measured by methods similar to those described in Gachet, C. et al., Br. J. Haemotol. (1995), 91, 434-444 and Mills, D. C., Thromb. Haemost (1996), 76, 835-856, and by the assay described below. With respect to P2Y12 binding affinity, a preferred embodiment of the invention comprises compounds which have an IC50<1 mM for P2Y12 binding affinity as determined in the assay described, and which preferably do not substantially influence the activity of other receptors involved in platelet aggregation and fibrinolysis whose inhibition or activation is not desired (using the same concentration of the antagonist). The ability of the compounds to inhibit ADP-induced aggregation of platelets may be measured by methods similar to those described in R. G. Humphries et al., Br. J. Pharm. (1995), Vol. 115, pp. 1110-1116 and J. F. Mustard et al. Methods in Enzymology, Vol. 169, p. 3 and by the method described below. The ability of the compounds to inhibit thrombus formation in vivo or ex vivo may be measured by methods similar to those described in J. M. Herbert et al., Cardiovasc. Drug Rev. (1993), 11, 180-198 or J. D. Folts et al., Circulation (1976), 54, 365. The results of these assays clearly demonstrate that the compounds of the invention are functional antagonists of the platelet adenosine diphosphate receptor and are therefore useful for inhibiting platelet aggregation and thrombus formation.

As platelet ADP P2Y12 receptor antagonists the compounds of the formula I and/or their physiologically tolerable salts and/or their prodrugs are generally suitable for the therapy and prophylaxis of conditions in which the activity of platelet ADP P2Y12 receptor plays a role or has an undesired extent, or which can favorably be influenced by inhibiting P2Y12 receptor or decreasing the activity, or for the prevention, alleviation or cure of which an inhibition of platelet ADP P2Y12 receptor or a decrease in the activity is desired by the physician. As inhibition of the platelet ADP P2Y12 receptor influences platelet activation, platelet aggregation and platelet degranulation and promote platelet disaggregation, the compounds of the formula I and/or their physiologically tolerable salts and/or their prodrugs are generally suitable for reducing blood thrombus formation, or for the therapy and prophylaxis of conditions in which the activity of the platelet aggregation and thus blood coagulation system plays a role or has an undesired extent, or which can favorably be influenced by reducing thrombus formation, or for the prevention, alleviation or cure of which a decreased activity of the platelet aggregation system is desired by the physician. A specific subject of the present invention thus are the reduction or inhibition of unwanted thrombus formation, in particular in an individual, by administering an effective amount of a compound of the formula I and/or a physiologically tolerable salt and/or a prodrug thereof, as well as pharmaceutical preparations thereof.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of the P2Y12 receptor or for influencing platelet activation, platelet aggregation and platelet degranulation and promote platelet disaggregation, inflammatory response or for the therapy or prophylaxis of the diseases mentioned above or below, for example for the production of pharmaceuticals for the therapy and prophylaxis of cardiovascular disorders, thromboembolic diseases or restenosis. The invention also relates to the use of the compounds of the formula I and/or their physiologically tolerable salts and/or their prodrugs for the inhibition of P2Y12 receptor or for influencing platelet activation, platelet aggregation and platelet degranulation and promote platelet disaggregation or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatine capsules it is possible to use, for example, lactose, cornstarch or derivatives thereof, talc, stearic acid or its salts, etc. Carriers for soft gelatine capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a physiologically tolerable salt and/or its prodrug, the pharmaceutical preparations can also contain one or more other therapeutically or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

The compounds of the present invention can be administered alone or in combination with one or more additional therapeutic agents. These other agents include, but are not limited to, anticoagulant or coagulation inhibitory agents, other antiplatelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Examples of suitable anti-arrhythmic agents for use in combination with the present compounds include: Class I agents (such as propafenone); Class II agents (such as carvadiol and propranolol); Class HI agents (such as sotalol, dofetilide, amiodarone, azimilide, and ibutilide); Class IV agents (such as ditiazem and verapamil); K+ channel openers such as IAch inhibitors, and Iκur inhibitors (e.g., compounds such as those disclosed in WO01/40231).

Examples of suitable antihypertensive agents for use in combination with the compounds of the present invention include: alpha adrenergic blockers; beta adrenergic blockers; calcium channel blockers (e.g. diltiazem, verapamil, nifedipine, amlodipine, and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, muzolimine, bumetanide, triamterene, amiloride, spironolactone); renin inhibitors; angiotensin-converting enzyme (ACE) inhibitors (e.g., captopril, zofenopril, fosinopril, enalapril, ceranopril, cilazopril, delapril, pentopril, quinapril, ramipril, lisinopril); angiotensin AT-I receptor antagonists (e.g., losartan, irbesartan, valsartan); ET-A receptor antagonists (e.g., sitaxsentan, atrsentan, and compounds disclosed in U.S. Pat. Nos. 5,612,359 and 6,043,265); Dual ET-A/AT-I antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat, and nitrates); and β-blockers (e.g., propanolol, nadolol, or carvedilol).

Examples of other suitable anti-platelet agents for use in combination with the compounds of the present invention, include, but are not limited to, the various known non-steroidal anti-inflammatory drugs (NSAIDS) such as acetaminophen, aspirin, codeine, diclofenac, droxicam, fentanyl, ibuprofen, indomethacin, ketorolac-, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicyclic acid or ASA) and piroxicam are preferred. Other suitable platelet inhibitory agents include glycoprotein IIb/IIIa blockers (e.g., abciximab, eptifibatide, tirofiban, integrelin), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), protease-activated receptor 1 (PAR-I) antagonists (e.g., SCH-530348, SCH-203099, SCH-529153, and SCH-205831), and pharmaceutically acceptable salts or prodrugs thereof.

Examples of suitable anticoagulants for use in combination with the compounds of the present invention include warfarin and heparin (either unfractionated heparin such as enoxaparin and dalteparin or any commercially available low molecular weight heparin, for example LOVENOX™), synthetic pentasaccharide, direct acting thrombin inhibitors including hirudin and argatroban, factor VIla inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art. The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (INK), lanoteplase (nPA), factor VIla inhibitors, thrombin inhibitors, inhibitors of factors EKa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain. Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, muzolimine, bumetanide, triamterene, amiloride, and spironolactone. Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; nicotonic acid; fenofibric acid derivatives (e.g., gemfibrozil, clofibrat, fenofibrate and benzafibrate); probucol; choesterol absorption inhibitors; and cholesterol ester transfer protein inhibitors (e.g., CP-529414). Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone, and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-I), and dipeptidyl peptidase IV (DPP4) inhibitors.

Examples of suitable anti-depressant agents for use in combination with the compounds of the present invention include nefazodone and sertraline. Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-I and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene. Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat, aP2 inhibitors (such as those disclosed in WO00/59506), and cannabinoid receptor CBI antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

A compound of the formula I can also advantageously be used as an antiaggregant outside an individual. For example, an effective amount of a compound of the invention can be contacted with a freshly drawn blood sample to prevent aggregation of the blood sample. Further, a compound of the formula I or its salts can be used for diagnostic purposes, for example in in vitro diagnoses, and as an auxiliary in biochemical investigations. For example, a compound of the formula I can be used in an assay to identify the presence of the P2Y12 receptor or to isolate the P2Y12 receptor containing tissue in a substantially purified form. A compound of the invention can be labelled with, for example, a radioisotope, and the labelled compound bound to the P2Y12 receptor is then detected using a routine method useful for detecting the particular label. Thus, a compound of the formula I or a salt thereof can be used as a probe to detect the location or amount of P2Y12 receptors activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to an acidlabile protecting group (eg. a tBu group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center, like for example a basic nitrogen, were either obtained and used as free base or in salt form like, for example, a trifluoroacetic acid salt, a hydrobromic acid salt, sulfuric acid salt, or a hydrochloric acid salt.

| Abbreviations used: | |
|---|---|
| tert-Butyl | tBu |
| 2,2'-bis(diphenylphoshino-1,1'-binaphthyl | Binap |
| Bis-(oxo-3-oxazolidinyl)-phosphoryl chloride | BOP-Cl |
| Dibenzylidenacetone | dba |
| Dichloromethane | DCM |
| Dicyclohexyl-carbodiimide | DCC |
| Diethylphosphoryl cyanide | DEPC |
| Diisopropylethyl amine | DIPEA |
| 4-Dimethyaminopyridine | DMAP |
| N,N-Dimethylformamide | DMF |
| Dimethylsulfoxide | DMSO |
| 1,1'-Bis(diphenylphosphino)ferrocene | DPPF |
| 1-(3-Dimethylaminopropyl)-3-ethylcarbodiimide hydrochloride | EDC |
| O-(7-Azabenzotriazol-1-yl)-N,N,N',N'-Tetramethyluronium-hexafluorophosphate | HATU |
| 1-Hydroxy-7-azabenzotriazole | HOAT |
| 1-Hydroxybenzotriazole | HOBT |
| N-Bromosuccinimide | NBS |
| N-Chlorosuccinimide | NCS |
| N-Iodosuccinimide | NIS |
| N-Ethylmorpholine | NEM |
| Methanol | MeOH |
| Room temperature 20° C. to 25° C. | RT |
| Saturated | sat. |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

Example 1

4-((S)-4-Carboxy-2-{[5-(1-ethoxycarbonyl-cyclobutoxy)-1-phenyl-1H-pyrazole-3-carbonyl]-amino}-butyryl)-piperazine-1-carboxylic acid ethyl ester (i) 4-((S)-2-Benzyloxycarbonylamino-4-tert-butoxycarbonyl-butyryl)-piperazine-1-carboxylic acid ethyl ester To a solution of 15 g of (S)-2-Benzyloxycarbonylaminopentanedioic acid 5-tert-butyl ester, 20.4 g of NEM and 14.5 g of TOTU in 75 ml of DMF, 7.4 g of piperazine-1-carboxylic acid ethyl ester was added at RT and stirred for 16 h. The reaction mixture was then diluted with saturated aqueous sodium hydrogen carbonate solution and then extracted with 300 ml of ethyl acetate. The organic phase was washed with diluted saturated aqueous sodium hydrogen carbonate solution and dried over $MgSO_4$. The solvents were removed under reduced pressure. The crude product was purified by chromatography on silica gel eluting with n-heptane/ethyl acetate (1/1). The fractions containing the product were combined and the solvent evaporated under reduced pressure. Yield: 20.6 g.

(ii) 4-((S)-2-Amino-4-tert-butoxycarbonyl-butyryl)-piperazine-1-carboxylic acid ethyl ester A solution of 20.6 g of 4-((S)-2-Benzyloxycarbonylamino-4-tert-butoxycarbonyl-butyryl)-piperazine-1-carboxylic acid ethyl ester in 200 ml of ethanol was purged with argon. Then, 2 g of Pd/C (5-10%) was added and the mixture stirred under a hydrogen atmosphere (4 bar). After 16 h the reaction mixture was filtered through a pad of celite and the solvents were removed under reduced pressure. After drying under reduced pressure the product was used in the subsequent reaction. Yield: 14.4 g.

(iii) 4-{(S)-4-tert-Butoxycarbonyl-2-[(5-hydroxy-1-phenyl-1H-pyrazole-3-carbonyl)-amino]-butyryl}-piperazine-1-carboxylic acid ethyl ester To a solution of 1.3 g of 5-Hydroxy-1-phenyl-1H-pyrazole-3-carboxylic acid and 2.2 g of 4-((S)-2-Amino-4-tert-butoxycarbonyl-butyryl)-piperazine-1-carboxylic acid ethyl ester in 80 ml of DMF, 0.9 g of HOBT and 1.3 g of EDC was added and the reaction mixture was stirred for 2 h at RT. Then, the reaction mixture was diluted with water and extracted with DCM. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 2.7 g.

(iv) 4-((S)-4-tert-Butoxycarbonyl-2-{[5-(1-ethoxycarbonyl-cyclobutoxy)-1-phenyl-1H-pyrazole-3-carbonyl]-amino}-butyryl)-piperazine-1-carboxylic acid ethyl ester To a solution of 1.5 g of 4-{(S)-4-tert-Butoxycarbonyl-2-[(5-hydroxy-1-phenyl-1H-pyrazole-3-carbonyl)-amino]-butyryl}-piperazine-1-carboxylic acid ethyl ester in 20 ml of DMF, 1.8 g of cesium carbonate and 1.2 g of 1-Bromocyclobutanecarboxylic acid ethyl ester was added and heated to 100° C. for 2 h. Then, the reaction mixture was diluted with water and extracted with ethyl acetate (3×150 ml). The combined organic phases were dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 860 mg.

(v) 4-((S)-4-Carboxy-2-{[5-(1-ethoxycarbonyl-cyclobutoxy)-1-phenyl-1H-pyrazole-3-carbonyl]-amino}-butyryl)-piperazine-1-carboxylic acid ethyl ester To a solution of 860 mg of 4-((S)-4-tert-Butoxycarbonyl-2-{[5-(1-ethoxycarbonyl-cyclobutoxy)-1-phenyl-1H-pyrazole-3-carbonyl]-amino}-butyryl)-piperazine-1-carboxylic acid ethyl ester in 5 ml of DCM, 0.8 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. Yield: 320 mg MS (ES$^+$): m/e=600.

Example 2

4-{(S)-2-[(5-Benzyloxy-1-phenyl-1H-pyrazole-3-carbonyl)-amino]-4-carboxy-butyryl}-piperazine-1-carboxylic acid ethyl ester The title compound was prepared by adapting the procedures described in example 1 with the difference that Bromomethyl-benzene was used instead of 1-Bromo-cyclobutanecarboxylic acid ethyl ester. MS (ES$^+$): m/e=564.

Example 3

4-((S)-4-Carboxy-2-{[5-(ethoxycarbonyl-phenyl-methoxy)-1-phenyl-1H-pyrazole-3-carbonyl]-amino}-butyryl)-piperazine-1-carboxylic acid ethyl ester The title compound was prepared by adapting the procedures described in example 1 with the difference that Bromo-phenyl-acetic acid ethyl ester was used instead of 1-Bromo-cyclobutanecarboxylic acid ethyl ester. MS (ES$^+$): m/e=636.

Example 4

4-((S)-4-Carboxy-2-{[5-(1-ethoxycarbonyl-1-methyl-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Bromo-2-methyl-propionic acid ethyl ester was used instead of 1-Bromo-cyclobutanecarboxylic acid ethyl ester. MS (ES$^+$): m/e=588.

Example 5

4-{(S)-4-Carboxy-2-[(5-ethoxycarbonylmethoxy-1-phenyl-1H-pyrazole-3-carbonyl)-amino]-butyryl}-piperazine-1-carboxylic acid ethyl ester (i) 4-{(S)-4-tert-Butoxycarbonyl-2-[(5-ethoxycarbonylmethoxy-1-phenyl-1H-pyrazole-3-carbonyl)-amino]-butyryl}-piperazine-1-carboxylic acid ethyl ester To a solution of 60 mg of 4-{(S)-4-tert-Butoxycarbonyl-2-[(5-hydroxy-1-phenyl-1H-pyrazole-3-carbonyl)-amino]-butyryl}-piperazine-1-carboxylic acid ethyl ester in 20 ml of DMF, 73 mg of cesium carbonate and 38 mg of Bromo-acetic acid ethyl ester was added and heated to 100° C. for 4 h. Then, the reaction mixture was diluted with water and extracted with ethyl acetate. The combined organic phases were dried over MgSO$_4$ and the solvents were removed under reduced pressure. The crude product was used in the subsequent reaction.
Yield: 73 mg.

(ii) 4-{(S)-4-Carboxy-2-[(5-ethoxycarbonylmethoxy-1-phenyl-1H-pyrazole-3-carbonyl)-amino]-butyryl}-piperazine-1-carboxylic acid ethyl ester To a solution of 73 mg of 4-{(S)-4-tert-Butoxycarbonyl-2-[(5-ethoxycarbonylmethoxy-1-phenyl-1H-pyrazole-3-carbonyl)-amino]-butyryl}-piperazine-1-carboxylic acid ethyl ester in 1 ml of DCM, 0.2 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid.
Yield: 37 mg MS (ES+): m/e=560.

Example 6

4-((S)-4-Carboxy-2-{[5-(2-ethoxycarbonyl-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that 3-Bromo-propionic acid ethyl ester was used instead of 1-Bromo-cyclobutanecarboxylic acid ethyl ester. MS (ES$^+$): m/e=574.

Example 7

4-((S)-4-Carboxy-2-{[5-(1-carboxy-cyclobutoxy)-1-phenyl-1H-pyrazole-3-carbonyl]-amino}-butyryl)-piperazine-1-carboxylic acid ethyl ester To a solution of 70 mg of 4-((S)-4-Carboxy-2-{[5-(1-ethoxycarbonyl-cyclobutoxy)-1-phenyl-1H-pyrazole-3-carbonyl]-amino}-butyryl)-piperazine-1-carboxylic acid ethyl ester in 2 ml of THF, 0.3 ml of a 1 M aqueous NaOH solution was added. After stirring for 1 h at RT additional 0.3 ml of a 1 M aqueous NaOH solution was added and allowed to stir upon completion of the reaction. Then, the reaction was acidified to pH 1 with diluted aqueous hydrochloric acid and extracted with DCM (3×50 ml). The combined organic phases were dried over MgSO$_4$ and the solvents were removed under reduced pressure. Yield: 49 mg MS (ES+): m/e=572.

Example 8

2-{5-[(S)-3-Carboxy-1-(4-ethoxycarbonyl-piperazine-1-carbonyl)-propylcarbamoyl]-2-phenyl-2H-pyrazol-3-yloxy}-malonic acid diethyl ester The title compound was prepared by adapting the procedures described in example 1 with the difference that 2-Bromo-malonic acid diethyl ester was used instead of 1-Bromo-cyclobutanecarboxylic acid ethyl ester. MS (ES$^+$): m/e=632.

Example 9

4-((S)-4-Carboxy-2-{[5-(2-oxo-tetrahydro-furan-3-yloxy)-1-phenyl-1H-pyrazole-3-carbonyl]-amino}-butyryl)-piperazine-1-carboxylic acid ethyl ester The title compound was prepared by adapting the procedures described in example 1 with the difference that 3-Bromo-dihydro-furan-2-one was used instead of 1-Bromo-cyclobutanecarboxylic acid ethyl ester. MS (ES$^+$): m/e=558.

Example 10

4-((S)-4-Carboxy-2-{[5-(1-carboxy-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Bromo-propionic acid was used instead of 1-Bromo-cyclobutanecarboxylic acid ethyl ester. MS (ES+): m/e=546.

Example 11

4-{(S)-4-Carboxy-2-[(5-carboxymethoxy-1-phenyl-1H-pyrazole-3-carbonyl)-amino]-butyryl}-piperazine-1-carboxylic acid ethyl ester The title compound was prepared by adapting the procedures described in example 1 with the difference that Bromoacetic acid was used instead of 1-Bromo-cyclobutanecarboxylic acid ethyl ester. MS (ES+): m/e=532.

Example 12

4-((S)-4-Carboxy-2-{[5-(1-ethoxycarbonyl-cyclobutoxy)-1-(3-methoxy-phenyl)-1H-pyrazole-3-carbonyl]-amino}-butyryl)-piperazine-1-carboxylic acid ethyl ester (i) 5-Hydroxy-1-(3-methoxy-phenyl)-1H-pyrazole-3-carboxylic acid ethyl ester To a solution of 1.2 g of 2-Oxo-succinic acid diethyl ester monosodium salt in 10 ml acetic acid, 900 mg of (3-Methoxy-phenyl)-hydrazine hydrochloride was added and the reaction mixture was heated to 100° C. for 2 h. Then, the reaction mixture was diluted with water and extracted with ethylacetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure.
Yield: 300 mg.

(ii) 5-Hydroxy-1-(3-methoxy-phenyl)-1H-pyrazole-3-carboxylic acid

To a solution of 300 mg of 5-Hydroxy-1-(3-methoxy-phenyl)-1H-pyrazole-3-carboxylic acid ethyl ester in 5 ml of THF, 1 ml of a 1 M aqueous NaOH solution was added. After 3 h the reaction was acidified to pH 1 with diluted aqueous hydrochloric acid and the organic solvent was removed under reduced pressure. The precipitated product was collected by filtration and was used in the subsequent reaction. Yield: 267 mg.

(iii) 4-((S)-4-tert-Butoxycarbonyl-2-{[5-hydroxy-1-(3-methoxy-phenyl)-1H-pyrazole-3-carbonyl]-amino}-butyryl)-piperazine-1-carboxylic acid ethyl ester To a solution of 150 mg of 5-Hydroxy-1-(3-methoxy-phenyl)-1H-pyrazole-3-carboxylic acid and 220 mg of 4-((S)-2-Amino-4-tert-butoxycarbonyl-butyryl)-piperazine-1-carboxylic acid ethyl ester in 3 ml of DMF, 98 mg of HOBT and 122 mg of EDC was added and the reaction mixture was stirred for 16 h at RT. Then, the reaction mixture was diluted with water and filtered through a Chem Elut® cartridge by eluting with ethyl acetate. The solvents were removed under reduced pressure. The crude product was purified by chromatography on silica gel eluting with a gradient of n-heptane/ethyl acetate. The fractions containing the product were combined and the solvent evaporated under reduced pressure.
Yield: 260 mg.

(iv) 4-((S)-4-tert-Butoxycarbonyl-2-{[5-(1-ethoxycarbonyl-cyclobutoxy)-1-(3-methoxy-phenyl)-1H-pyrazole-3-carbonyl]-amino}-butyryl)-piperazine-1-carboxylic acid ethyl ester To a solution of 100 mg of 4-((S)-4-tert-Butoxycarbonyl-2-{[5-hydroxy-1-(3-methoxy-phenyl)-1H-pyrazole-3-carbonyl]-amino}-butyryl)-piperazine-1-carboxylic acid ethyl ester in 4 ml of DMF, 116 mg of cesium carbonate and 74 mg of 1-Bromo-cyclobutanecarboxylic acid ethyl ester was added and heated to 100° C. for 3 h. Then, the reaction mixture was diluted with water and filtered through a Chem Elut® cartridge by eluting with ethyl acetate. The solvents were removed under reduced pressure. The crude product was used in the subsequent reaction. Yield: 90 mg.

(v) 4-((S)-4-Carboxy-2-{[5-(1-ethoxycarbonyl-cyclobutoxy)-1-(3-methoxy-phenyl)-1H-pyrazole-3-carbonyl]-amino}-butyryl)-piperazine-1-carboxylic acid ethyl ester To a solution of 90 mg of 4-((S)-4-tert-Butoxycarbonyl-2-{[5-(1-ethoxycarbonyl-cyclobutoxy)-1-(3-methoxy-phenyl)-1H-pyrazole-3-carbonyl]-amino}-butyryl)-piperazine-1-carboxylic acid ethyl ester in 3 ml of DCM, 0.3 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. Yield: 15 mg
MS (ES+): m/e=630.

Example 13

4-((S)-4-Carboxy-2-{[1-(2,5-dimethyl-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (2,5-Dimethyl-phenyl)-hydrazine was used instead of (3-Methoxy-phenyl)-hydrazine. MS (ES+): m/e=628.

Example 14

4-((S)-4-Carboxy-2-{[5-(1-ethoxycarbonyl-cyclobutoxy)-1-(4-trifluoromethoxy-phenyl)-1H-pyrazole-3-carbonyl]-amino}-butyryl)-piperazine-1-carboxylic acid ethyl ester The title compound was prepared by adapting the procedures described in example 12 with the difference that (4-Trifluoromethoxy-phenyl)-hydrazine was used instead of (3-Methoxy-phenyl)-hydrazine. MS (ES+): m/e=684.

Example 15

4-((S)-4-Carboxy-2-{[5-(1-ethoxycarbonyl-cyclobutoxy)-1-m-tolyl-1H-pyrazole-3-carbonyl]-amino}-butyryl)-piperazine-1-carboxylic acid ethyl ester The title compound was prepared by adapting the procedures described in example 12 with the difference that m-Tolyl-hydrazine was used instead of (3-Methoxy-phenyl)-hydrazine. MS (ES+): m/e=614.

Example 16

4-((S)-4-Carboxy-2-{[5-ethoxycarbonylmethoxy-1-(3-methoxy-phenyl)-1H-pyrazole-3-carbonyl]-amino}-butyryl)-piperazine-1-carboxylic acid ethyl ester (i) 5-Hydroxy-1-(3-methoxy-phenyl)-1H-pyrazole-3-carboxylic acid ethyl ester To a solution of 1.2 g of 2-Oxo-succinic acid diethyl ester monosodium salt in 10 ml acetic acid, 900 mg of (3-Methoxy-phenyl)-hydrazine hydrochloride was added and the reaction mixture was heated to 100° C. for 2 h. Then, the reaction mixture was diluted with water and extracted with ethylacetate. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure.
Yield: 300 mg.

(ii) 5-Hydroxy-1-(3-methoxy-phenyl)-1H-pyrazole-3-carboxylic acid

To a solution of 300 mg of 5-Hydroxy-1-(3-methoxy-phenyl)-1H-pyrazole-3-carboxylic acid ethyl ester in 5 ml of THF, 1 ml of a 1 M aqueous NaOH solution was added. After 3 h the reaction was acidified to pH 1 with diluted aqueous hydrochloric acid and the organic solvents was removed under reduced pressure. The precipitated product was collected by filtration and was used in the subsequent reaction. Yield: 267 mg.

(iii) 4-((S)-4-tert-Butoxycarbonyl-2-{[5-hydroxy-1-(3-methoxy-phenyl)-1H-pyrazole-3-carbonyl]-amino}-butyryl)-piperazine-1-carboxylic acid ethyl ester To a solution of 150 mg of 5-Hydroxy-1-(3-methoxy-phenyl)-1H-pyrazole-3-carboxylic acid and 220 mg of 4-((S)-2-Amino-4-tert-butoxycarbonyl-butyryl)-piperazine-1-carboxylic acid ethyl ester in 3 ml of DMF, 98 mg of HOBT and 122 mg of EDC was added and the reaction mixture was stirred for 16 h at RT. Then, the reaction mixture was diluted with water and filtered through a Chem Elut® cartridge by eluting with ethyl acetate. The solvents were removed under reduced pressure. The crude product was purified by chromatography on silica gel eluting with a gradient of n-heptane/ethyl acetate. The fractions containing the product were combined and the solvent evaporated under reduced pressure.
Yield: 260 mg.

(iv) 4-((S)-4-tert-Butoxycarbonyl-2-{[5-ethoxycarbonylmethoxy-1-(3-methoxy-phenyl)-1H-pyrazole-3-carbonyl]-amino}-butyryl)-piperazine-1-carboxylic acid ethyl ester To a solution of 100 mg of 4-((S)-4-tert-Butoxycarbonyl-2-{[5-hydroxy-1-(3-methoxy-phenyl)-1H-pyrazole-3-carbonyl]-amino}-butyryl)-piperazine-1-carboxylic acid ethyl ester in 4 ml of DMF, 116 mg of cesium carbonate and 59 mg of Bromo-acetic acid ethyl ester was added and heated to 100° C. for 3 h. Then, the reaction mixture was diluted with water and filtered through a Chem Elut® cartridge by eluting with ethyl acetate. The solvents were removed under reduced pressure. The crude product was used in the subsequent reaction.
Yield: 95 mg.

(v) 4-((S)-4-Carboxy-2-{[5-ethoxycarbonylmethoxy-1-(3-methoxy-phenyl)-1H-pyrazole-3-carbonyl]-amino}-butyryl)-piperazine-1-carboxylic acid ethyl ester To a solution of 90 mg of 4-((S)-4-tert-Butoxycarbonyl-2-{[5-ethoxycarbonylmethoxy-1-(3-methoxy-phenyl)-1H-pyrazole-3-carbonyl]-amino}-butyryl)-piperazine-1-carboxylic acid ethyl ester in 3 ml of DCM, 0.3 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. Yield: 22 mg
MS (ES+): m/e=590.

Example 17

4-{(S)-4-Carboxy-2-[(5-ethoxycarbonylmethoxy-1-m-tolyl-1H-pyrazole-3-carbonyl)-amino]-butyryl}-piperazine-1-carboxylic acid ethyl ester The title compound was prepared by adapting the procedures described in example 16 with the difference that m-Tolyl-hydrazine was used instead of (3-Methoxy-phenyl)-hydrazine. MS (ES+): m/e=574.

Example 18

4-((S)-4-Carboxy-2-{[1-(3-chloro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (3-Chloro-phenyl)-hydrazine was used instead of (3-Methoxy-phenyl)-hydrazine. MS (ES+): m/e=634.

Example 19

4-((S)-4-Carboxy-2-{[1-(3-chloro-4-methyl-phenyl)-5-ethoxycarbonylmethoxy-1H-pyrazole-3-carbonyl]-amino}-butyryl)-piperazine-1-carboxylic acid ethyl ester The title compound was prepared by adapting the procedures described in example 16 with the difference that (3-Chloro-4-methyl-phenyl)-hydrazine was used instead of (3-Methoxy-phenyl)-hydrazine. MS (ES+): m/e=608, chloro pattern.

Example 20

4-((S)-4-Carboxy-2-{[5-(1-ethoxycarbonyl-cyclobutoxy)-1-p-tolyl-1H-pyrazole-3-carbonyl]-amino}-butyryl)-piperazine-1-carboxylic acid ethyl ester The title compound was prepared by adapting the procedures described in example 12 with the difference that p-Tolyl-hydrazine was used instead of (3-Methoxy-phenyl)-hydrazine.
MS (ES+): m/e=614.

Example 21

4-((S)-4-Carboxy-2-{[1-(3-chloro-4-fluoro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (3-Chloro-4-fluoro-phenyl)-hydrazine was used instead of (3-Methoxy-phenyl)-hydrazine. MS (ES$^+$): m/e=652, chloro pattern.

Example 22

4-((S)-4-Carboxy-2-{[1-(3-chloro-phenyl)-5-ethoxycarbonylmethoxy-1H-pyrazole-3-carbonyl]-amino}-butyryl)-piperazine-1-carboxylic acid ethyl ester The title compound was prepared by adapting the procedures described in example 16 with the difference that (3-Chloro-phenyl)-hydrazine was used instead of (3-Methoxy-phenyl)-hydrazine. MS (ES$^+$): m/e=594, chloro pattern.

Example 23

4-{(S)-4-Carboxy-2-[(5-ethmcarbonylmethoxy-1-p-tolyl-1H-pyrazole-3-carbonyl)-amino]-butyryl}-piperazine-1-carboxylic acid ethyl ester The title compound was prepared by adapting the procedures described in example 16 with the difference that p-Tolyl-hydrazine was used instead of (3-Methoxy-phenyl)-hydrazine. MS (ES$^+$): m/e=574.

Example 24

4-((S)-4-Carboxy-2-{[1-(3-cyano-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that 3-Hydrazino-benzonitrile was used instead of (3-Methoxy-phenyl)-hydrazine. MS (ES$^+$): m/e=625.

Example 25

4-((S)-4-Carboxy-2-{[1-(3,5-dimethyl-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (3,5-Dimethyl-phenyl)-hydrazine was used instead of (3-Methoxy-phenyl)-hydrazine. MS (ES$^+$): m/e=628.

Example 26

4-((S)-4-Carboxy-2-{[1-(3-cyano-phenyl)-5-ethoxycarbonylmethoxy-1H-pyrazole-3-carbonyl]-amino}-butyryl)-piperazine-1-carboxylic acid ethyl ester The title compound was prepared by adapting the procedures described in example 16 with the difference that 3-Hydrazino-benzonitrile was used instead of (3-Methoxy-phenyl)-hydrazine. MS (ES$^+$): m/e=585.

Example 27

4-((S)-4-Carboxy-2-{[1-(3-chloro-4-methyl-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (3-Chloro-4-methyl-phenyl)-hydrazine was used instead of (3-Methoxy-phenyl)-hydrazine. MS (ES$^+$): m/e=648, chloro pattern.

Example 28

4-((S)-4-Carboxy-2-{[1-(3,5-dimethyl-phenyl)-5-ethoxycarbonylmethoxy-1H-pyrazole-3-carbonyl]-amino}-butyryl)-piperazine-1-carboxylic acid ethyl ester The title compound was prepared by adapting the procedures described in example 16 with the difference that (3,5-Dimethyl-phenyl)-hydrazine was used instead of (3-Methoxy-phenyl)-hydrazine. MS (ES$^+$): m/e=588.

Example 29

4-((S)-4-Carboxy-2-{[5-(1-ethoxycarbonyl-cyclobutoxy)-1-(4-isopropyl-phenyl)-1H-pyrazole-3-carbonyl]-amino}-butyryl)-piperazine-1-carboxylic acid ethyl ester The title compound was prepared by adapting the procedures described in example 12 with the difference that (4-Isopropyl-phenyl)-hydrazine was used instead of (3-Methoxy-phenyl)-hydrazine. MS (ES$^+$): m/e=642.

Example 30

4-((S)-4-Carboxy-2-{[5-(1-ethoxycarbonyl-cyclobutoxy)-1-(2-ethyl-phenyl)-1H-pyrazole-3-carbonyl]-amino}-butyryl)-piperazine-1-carboxylic acid ethyl ester The title compound was prepared by adapting the procedures described in example 12 with the difference that (2-Ethyl-phenyl)-hydrazine was used instead of (3-Methoxy-phenyl)-hydrazine. MS (ES$^+$): m/e=628.

Example 31

4-((S)-4-Carboxy-2-{[5-(1-ethoxycarbonyl-cyclobutoxy)-1-(3-trifluoromethyl-phenyl)-1H-pyrazole-3-carbonyl]-amino}-butyryl)-piperazine-1-carboxylic acid ethyl ester The title compound was prepared by adapting the procedures described in example 12 with the difference that (3-Trifluoromethyl-phenyl)-hydrazine was used instead of (3-Methoxy-phenyl)-hydrazine. MS (ES$^+$): m/e=668.

Example 32

4-((S)-4-Carboxy-2-{[1-(3-chloro-2-fluoro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (3-Chloro-2-fluoro-phenyl)-hydrazine was used instead of (3-Methoxy-phenyl)-hydrazine. MS (ES$^+$): m/e=652, chloro pattern.

Example 33

4-((S)-4-Carboxy-2-{[5-(1-ethoxycarbonyl-cyclobutoxy)-1-naphthalen-1-yl-1H-pyrazole-3-carbonyl]-amino}-butyryl)-piperazine-1-carboxylic acid ethyl ester The title compound was prepared by adapting the procedures described in example 12 with the difference that Naphthalen-1-yl-hydrazine was used instead of (3-Methoxy-phenyl)-hydrazine. MS (ES$^+$): m/e=650.

Example 34

4-((S)-4-Carboxy-2-{[5-(1-ethoxycarbonyl-cyclobutoxy)-1-(3-nitro-phenyl)-1H-pyrazole-3-carbonyl]-amino}-butyryl)-piperazine-1-carboxylic acid ethyl ester The title compound was prepared by adapting the procedures described in example 12 with the difference that (3-Nitro-phenyl)-hydrazine was used instead of (3-Methoxy-phenyl)-hydrazine. MS (ES$^+$): m/e=645.

Example 35

4-((S)-4-Carboxy-2-{[1-(2,3-dimethyl-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (2,3-Dimethyl-phenyl)-hydrazine was used instead of (3-Methoxy-phenyl)-hydrazine. MS (ES$^+$): m/e=628.

Example 36

4-((S)-4-Carboxy-2-{[1-(3,4-difluoro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (3,4-Difluoro-phenyl)-hydrazine was used instead of (3-Methoxy-phenyl)-hydrazine. MS (ES$^+$): m/e=636.

Example 37

4-((S)-4-Carboxy-2-{[5-(1-ethoxycarbonyl-cyclobutoxy)-1-(4-ethyl-phenyl)-1H-pyrazole-3-carbonyl]-amino}-butyryl)-piperazine-1-carboxylic acid ethyl ester The title compound was prepared by adapting the procedures described in example 12 with the difference that (4-Ethyl-phenyl)-hydrazine was used instead of (3-Methoxy-phenyl)-hydrazine. MS (ES$^+$): m/e=628.

Example 38

4-((S)-4-Carboxy-2-{[1-(2-chloro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (2-Chloro-phenyl)-hydrazine was used instead of (3-Methoxy-phenyl)-hydrazine. MS (ES$^+$): m/e=634, chloro pattern.

Example 39

4-((S)-4-Carboxy-2-{[1-(2,6-dichloro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (2,6-Dichloro-phenyl)-hydrazine was used instead of (3-Methoxy-phenyl)-hydrazine. MS (ES$^+$): m/e=668, chloro pattern.

Example 40

4-((S)-4-Carboxy-2-{[1-(2,4-difluoro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (2,4-Difluoro-phenyl)-hydrazine was used instead of (3-Methoxy-phenyl)-hydrazine. MS (ES$^+$): m/e=636.

Example 41

4-((S)-4-Carboxy-2-{[5-(1-ethoxycarbonyl-cyclobutoxy)-1-(4-methylsulfanyl-phenyl)-1H-pyrazole-3-carbonyl]-amino}-butyryl)-piperazine-1-carboxylic acid ethyl ester The title compound was prepared by adapting the procedures described in example 12 with the difference that (4-Methylsulfanyl-phenyl)-hydrazine was used instead of (3-Methoxy-phenyl)-hydrazine. MS (ES$^+$): m/e=646.

Example 42

4-((S)-4-Carboxy-2-{[5-(1-ethoxycarbonyl-cyclobutoxy)-1-(4-trifluoromethyl-phenyl)-1H-pyrazole-3-carbonyl]-amino}-butyryl)-piperazine-1-carboxylic acid ethyl ester The title compound was prepared by adapting the procedures described in example 12 with the difference that (4-Trifluoromethyl-phenyl)-hydrazine was used instead of (3-Methoxy-phenyl)-hydrazine. MS (ES$^+$): m/e=668.

Example 43

4-((S)-4-Carboxy-2-{[1-(3-chloro-2-methyl-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (3-Chloro-2-methyl-phenyl)-hydrazine was used instead of (3-Methoxy-phenyl)-hydrazine. MS (ES$^+$): m/e=648, chloro pattern.

Example 44

4-((S)-4-Carboxy-2-{[5-(1-ethoxycarbonyl-cyclobutoxy)-1-thiazol-2-yl-1H-pyrazole-3-carbonyl]-amino}-butyryl)-piperazine-1-carboxylic acid ethyl ester The title compound was prepared by adapting the procedures described in example 12 with the difference that Thiazol-2-yl-hydrazine was used instead of (3-Methoxy-phenyl)-hydrazine. MS (ES$^+$): m/e=607.

Example 45

4-((S)-4-Carboxy-2-{[5-(1-ethoxycarbonyl-cyclobutoxy)-1-(2-fluoro-phenyl)-1H-pyrazole-3-carbonyl]-amino}-butyryl)-piperazine-1-carboxylic acid ethyl ester The title compound was prepared by adapting the procedures described in example 12 with the difference that (2-Fluoro-phenyl)-hydrazine was used instead of (3-Methoxy-phenyl)-hydrazine. MS (ES$^+$): m/e=618.

Example 46

4-((S)-4-Carboxy-2-{[5-(1-ethoxycarbonyl-cyclobutoxy)-1-(4-sulfamoyl-phenyl)-1H-pyrazole-3-carbonyl]-amino}-butyryl)-piperazine-1-carboxylic acid ethyl ester The title compound was prepared by adapting the procedures described in example 12 with the difference that 4-Hydrazino-benzenesulfonamide was used instead of (3-Methoxy-phenyl)-hydrazine. MS (ES$^+$): m/e=679.

Example 47

4-((S)-4-Carboxy-2-{[5-(3-methoxy-propoxy)-1-phenyl-1H-pyrazole-3-carbonyl]-amino}-butyryl)-piperazine-1-carboxylic acid ethyl ester The title compound was prepared by adapting the procedures described in example 1 with the difference that 1-Bromo-3-methoxy-propane was used instead of 1-Bromo-cyclobutanecarboxylic acid ethyl ester. MS (ES$^+$): m/e=546.

Example 48

4-((S)-4-Carboxy-2-{[5-(2-ethoxy-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that 1-Bromo-2-ethoxy-ethane was used instead of 1-Bromo-cyclobutanecarboxylic acid ethyl ester. MS (ES$^+$): m/e=546.

Example 49

4-{(S)-4-Carboxy-2-[(5-cyclobutoxy-1-phenyl-1H-pyrazole-3-carbonyl)-amino]butyryl}-piperazine-1-carboxylic acid ethyl ester To a solution of 50 mg of 4-{(S)-4-tert-Butoxycarbonyl-2-[(5-hydroxy-1-phenyl-1H-pyrazole-3-carbonyl)-amino]-butyryl}-piperazine-1-carboxylic acid ethyl ester and 8 mg of Cyclobutanol in 2 ml of THF, 37 mg of polymerbound triphenyl phosphine (Fluka, 3 mmol triphenylphosphine/g resin) and 20 mg of Diethyl azodicarboxylate was added and stirred for 16 h. Then, the reaction mixture was filtered and the solvents were removed under reduced pressure. The residue was dissolved in 1 ml of DCM and 0.2 ml TFA. After 4 h 10 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. Yield: 2 mg MS (ES+): m/e=528.

Example 50

4-((S)-4-Carboxy-2-{[5-(2-hydroxy-2-methoxycarbonyl-propoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Methyl-oxirane-2-carboxylic acid methyl ester was used instead of 1-Bromo-cyclobutanecarboxylic acid ethyl ester. MS (ES$^+$): m/e=590.

Example 51

4-{(S)-4-Carboxy-2-[(5-cyclopropylmethoxy-1-phenyl-1H-pyrazole-3-carbonyl)-amino]-butyryl}-piperazine-1-carboxylic acid ethyl ester The title compound was prepared by adapting the procedures described in example 1 with the difference that Bromomethyl-cyclopropane was used instead of 1-Bromo-cyclobutanecarboxylic acid ethyl ester. MS (ES$^+$): m/e=528.

Example 52

4-((S)-4-Carboxy-2-{[5-(4-hydroxy-butoxy)-1-phenyl-1H-pyrazole-3-carbonyl]-amino}-butyryl)-piperazine-1-carboxylic acid ethyl ester The title compound was prepared by adapting the procedures described in example 1 with the difference that 4-Bromo-butan-1-ol was used instead of 1-Bromo-cyclobutanecarboxylic acid ethyl ester. MS (ES$^+$): m/e=546.

Example 53

4-((S)-4-Carboxy-2-{[5-((R)-3-hydroxy-2-methylpropoxy)-1-phenyl-1H-pyrazole-3-carbonyl]-amino}-butyryl)-piperazine-1-carboxylic acid ethyl ester The title compound was prepared by adapting the procedures described in example 1 with the difference that (R)-3-Bromo-2-methyl-propan-1-ol was used instead of 1-Bromo-cyclobutanecarboxylic acid ethyl ester. MS (ES$^+$): m/e=546.

Example 54

4-((S)-4-Carboxy-2-{[5-(2,2-difluoro-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that Trifluoro-methanesulfonic acid 2,2-difluoro-ethyl ester was used instead of 1-Bromo-cyclobutanecarboxylic acid ethyl ester. MS (ES$^+$): m/e=538.

Example 55

4-{(S)-2-[(5-Carbamoylmethoxy-1-phenyl-1H-pyrazole-3-carbonyl)-amino]-4-carboxy-butyryl}-piperazine-1-carboxylic acid ethyl ester The title compound was prepared by adapting the procedures described in example 1 with the difference that 2-Bromoacetamide was used instead of 1-Bromo-cyclobutanecarboxylic acid ethyl ester. MS (ES+): m/e=531.

Example 56

4-((S)-4-Carboxy-2-{[5-(isopropylcarbamoyl-methoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Chloro-N-isopropyl-acetamide was used instead of 1-Bromo-cyclobutanecarboxylic acid ethyl ester. MS (ES$^+$): m/e=573.

Example 57

4-{(S)-4-Carboxy-2-[(5-methylcarbamoylmethoxy-1-phenyl-1H-pyrazole-3-carbonyl)-amino]-butyryl}-piperazine-1-carboxylic acid ethyl ester The title compound was prepared by adapting the procedures described in example 1 with the difference that 2-Chloro-N-methyl-acetamide was used instead of 1-Bromo-cyclobutanecarboxylic acid ethyl ester. MS (ES$^+$): m/e=545.

Example 58

4-{(S)-4-Carboxy-2-[(5-diethylcarbamoylmethoxy-1-phenyl-1H-pyrazole-3-carbonyl)-amino]-butyryl}-piperazine-1-carboxylic acid ethyl ester The title compound was prepared by adapting the procedures described in example 1 with the difference that 2-Chloro-N,N-diethyl-acetamide was used instead of 1-Bromo-cyclobutanecarboxylic acid ethyl ester. MS (ES$^+$): m/e=587.

Example 59

4-{(S)-4-Carboxy-2-[(5-dimethylcarbamoyl-methoxy-1-phenyl-1H-pyrazole-3-carbonyl)-amino]-butyryl}-piperazine-1-carboxylic acid ethyl ester The title compound was prepared by adapting the procedures described in example 1 with the difference that 2-Chloro-N,N-dimethyl-acetamide was used instead of 1-Bromo-cyclobutanecarboxylic acid ethyl ester. MS (ES$^+$): m/e=559.

Example 60

4-{(S)-4-Carboxy-2-[(5-isopropoxycarbonyl-methoxy-1-phenyl-1H-pyrazole-3-carbonyl)-amino]-butyryl}-piperazine-1-carboxylic acid ethyl ester The title compound was prepared by adapting the procedures described in example 1 with the difference that Bromoacetic acid isopropyl ester was used instead of 1-Bromo-cyclobutanecarboxylic acid ethyl ester. MS (ES$^+$): m/e=574.

Example 61

2-[(S)-2-{[5-(1-Ethoxycarbonyl-cyclobutoxy)-1-phenyl-1H-pyrazole-3-carbonyl]-amino}-3-(4-ethoxycarbonyl-piperazin-1-yl)-3-oxo-propyl]-malonic acid The title compound was prepared by adapting the procedures described in example 1 with the difference that (S)-2-Benzyloxycarbonylamino-4-tert-butoxycarbonyl-pentanedioic acid 5-tert-butyl ester was used instead of (S)-2-Benzyloxycarbonylamino-pentanedioic acid 5-tert-butyl ester.
MS (ES$^+$): m/e=644.

Example 62

4-((S)-4-Carboxy-2-{[5-(1-isopropylcarbamoyl-cyclobutoxy)-1-phenyl-1H-pyrazole-3-carbonyl]-amino}-butyryl)-piperazine-1-carboxylic acid ethyl ester (i) 4-((S)-4-tert-Butoxycarbonyl-2-{[5-(1-carboxy-cyclobutoxy)-1-phenyl-1H-pyrazole-3-carbonyl]-amino}-butyryl)-piperazine-1-carboxylic acid ethyl ester To a solution of 680 mg of 4-((S)-4-tert-Butoxycarbonyl-2-{[5-(1-ethoxycarbonyl-cyclobutoxy)-1-phenyl-1H-pyrazole-3-carbonyl]-amino}-butyryl)-piperazine-1-carboxylic acid ethyl ester in 6 ml of THF, 1.6 ml of a 1 M aqueous NaOH solution was added. After stirring for 2 h at RT the reaction was acidified to pH 1 with diluted aqueous hydrochloric acid and extracted with DCM (3×50 ml). The combined organic phases were dried over $MgSO_4$ and the solvents were removed under reduced pressure.

Yield: 660 mg.

(ii) 4-((S)-4-Carboxy-2-{[5-(1-isopropylcarbamoyl-cyclobutoxy)-1-phenyl-1H-pyrazole-3-carbonyl]-amino}-butyryl)-piperazine-1-carboxylic acid ethyl ester To a solution of 50 mg of 4-((S)-4-tert-Butoxycarbonyl-2-{[5-(1-carboxy-cyclobutoxy)-1-phenyl-1H-pyrazole-3-carbonyl]-amino}-butyryl)-piperazine-1-carboxylic acid ethyl ester in 0.3 ml of DMF, 28 mg of TOTU, 36 mg of NEM and 10 mg of isopropylamine was added. The reaction mixture was allowed to stir at RT for 16 h. Then, the reaction mixture was diluted with water and filtered through a Chem Elut® cartridge by eluting with ethyl acetate. The solvents were removed under reduced pressure. The residue was purified by preparative HPLC (C18 reverse phase column, elution with a water/MeCN gradient with 0.1% TFA). The fractions containing the product were evaporated and lyophilized to yield a white solid. This residue was dissolved in 1 ml of DCM, 0.2 ml of TFA was added at RT. After 4 h 20 ml of toluene was added and the solvents were removed under reduced pressure. The residue was dissolved in 3 ml of water and lyophilized to yield a white solid.

Yield: 1.4 mg MS (ES+): m/e=613.

Example 63

4-((S)-4-Carboxy-2-{[5-(1-dimethylcarbamoyl-cyclobutoxy)-1-phenyl-1H-pyrazole-3-carbonyl]-amino}-butyryl)-piperazine-1-carboxylic acid ethyl ester The title compound was prepared by adapting the procedures described in example 62 with the difference that Dimethyl-amine was used instead of isopropylamine.
MS (ES$^+$): m/e=599.

Example 64

4-[(S)-2-({5-[1-(Azetidine-1-carbonyl)-cyclobutoxy]-1-phenyl-1H-pyrazole-3-carbonyl}-amino)-4-carboxy-butyryl]-piperazine-1-carboxylic acid ethyl ester The title compound was prepared by adapting the procedures described in example 62 with the difference that Azetidine was used instead of isopropylamine.
MS (ES$^+$): m/e=611.

Example 65

4-[(S)-4-Carboxy-2-({5-[1-(cyclopropylmethyl-carbamoyl)-cyclobutoxy]-1-phenyl-1H-pyrazole-3-carbonyl}-amino)-butyryl]-piperazine-1-carboxylic acid ethyl ester The title compound was prepared by adapting the procedures described in example 62 with the difference that C-Cyclopropyl-methylamine was used instead of isopropylamine.
MS (ES$^+$): m/e=625.

Example 66

4-((S)-4-Carboxy-2-{[5-(1-isobutylcarbamoyl-cyclobutoxy)-1-phenyl-1H-pyrazole-3-carbonyl]-amino}-butyryl)-piperazine-1-carboxylic acid ethyl ester The title compound was prepared by adapting the procedures described in example 62 with the difference that Isobutylamine was used instead of isopropylamine.
MS (ES$^+$): m/e=627.

Example 67

4-((S)-4-Carboxy-2-{[5-(1-diethylcarbamoyl-cyclobutoxy)-1-phenyl-1H-pyrazole-3-carbonyl]-amino}-butyryl)-piperazine-1-carboxylic acid ethyl ester The title compound was prepared by adapting the procedures described in example 62 with the difference that Diethyl-amine was used instead of isopropylamine.
MS (ES$^+$): m/e=627.

Example 68

4-[(S)-4-Carboxy-2-({5-[1-(isopropyl-methyl-carbamoyl)-cyclobutoxy]-1-phenyl-1H-pyrazole-3-carbonyl}-amino)-butyryl]-piperazine-1-carboxylic acid ethyl ester The title compound was prepared by adapting the procedures described in example 62 with the difference that Isopropyl-methyl-amine was used instead of isopropylamine.
MS (ES$^+$): m/e=627.

Example 69

4-[(S)-4-Carboxy-2-({5-[1-(methyl-propyl-carbamoyl)-cyclobutoxy]-1-phenyl-1H-pyrazole-3-carbonyl}-amino)-butyryl]-piperazine-1-carboxylic acid ethyl ester The title compound was prepared by adapting the procedures described in example 62 with the difference that Methyl-propyl-amine was used instead of isopropylamine.
MS (ES$^+$): m/e=627.

Example 70

4-((S)-2-{[5-(1-Butylcarbamoyl-cyclobutoxy)-1-phenyl-1H-pyrazole-3-carbonyl]-amino}-4-carboxy-butyryl)-piperazine-1-carboxylic acid ethyl ester The title compound was prepared by adapting the procedures described in example 62 with the difference that butylamine was used instead of isopropylamine.
MS (ES$^+$): m/e=627.

Example 71

4-[(S)-2-({5-[1-(Carbamoylmethyl-carbamoyl)-cyclobutoxy]-1-phenyl-1H-pyrazole-3-carbonyl}-amino)-4-carboxy-butyryl]-piperazine-1-carboxylic acid ethyl ester The title compound was prepared by adapting the procedures described in example 62 with the difference that 2-Amino-acetamide was used instead of isopropylamine.
MS (ES$^+$): m/e=628.

Example 74

4-((S)-4-Carboxy-2-{[5-(1-ethoxycarbonyl-cyclobutoxy)-1-isopropyl-1H-pyrazole-3-carbonyl]-amino}-butyryl)-piperazine-1-carboxylic acid ethyl ester The title compound was prepared by adapting the procedures described in example 12 with the difference that Isopropyl-hydrazine was used instead of (3-Methoxy-phenyl)-hydrazine.
MS (ES$^+$): m/e=566.

Example 75

4-((S)-4-Carboxy-2-{[5-ethoxycarbonylmethoxy-1-(3-fluoro-phenyl)-1H-pyrazole-3-carbonyl]-amino}-butyryl)-piperazine-1-carboxylic acid ethyl ester The title compound was prepared by adapting the procedures described in example 16 with the difference that (3-Fluoro-phenyl)-hydrazine was used instead of (3-Methoxy-phenyl)-hydrazine. MS (ES$^+$): m/e=578.

Example 76

4-((S)-4-Carboxy-2-{[5-(1-ethoxycarbonyl-cyclobutoxy)-1-(3-fluoro-phenyl)-1H-pyrazole-3-carbonyl]-amino}-butyryl)-piperazine-1-carboxylic acid ethyl ester The title compound was prepared by adapting the procedures described in example 12 with the difference that (3-Fluoro-phenyl)-hydrazine was used instead of (3-Methoxy-phenyl)-hydrazine. MS (ES$^+$): m/e=618.

Example 77

4-{(S)-4-Carboxy-2-[(5-ethoxycarbonylmethoxy-1-isopropyl-1H-pyrazole-3-carbonyl)-amino]-butyryl}-piperazine-1-carboxylic acid ethyl ester The title compound was prepared by adapting the procedures described in example 16 with the difference that Isopropyl-hydrazine was used instead of (3-Methoxy-phenyl)-hydrazine. MS (ES$^+$): m/e=526.

Example 78

4-{(S)-4-Carboxy-2-[(5-carboxy-1-phenyl-1H-pyrazole-3-carbonyl)-amino]-butyryl}-piperazine-1-carboxylic acid ethyl ester (i) 4-{(S)-4-tert-Butoxycarbonyl-2-[(5-carboxy-1-phenyl-1H-pyrazole-3-carbonyl)-amino]-butyryl}-piperazine-1-carboxylic acid ethyl ester To a vigorously stirred mixture of 320 mg of 4-{(S)-4-tert-Butoxycarbonyl-2-[(5-furan-2-yl-1-phenyl-1H-pyrazole-3-carbonyl)-amino]-butyryl}-piperazine-1-carboxylic acid ethyl ester in 2 ml of tetrachloromethane, 2 ml of acetonitrile and 3 ml of water, 531 mg of sodium periodate and 1 mg of ruthenium(III)chloride was added at RT. After 1 h, 20 ml of toluene was added and the solvents were removed under reduced pressure. The crude product was used in the subsequent reaction. Yield: 314 mg.

(ii) 4-{(S)-4-Carboxy-2-[(5-carboxy-1-phenyl-1H-pyrazole-3-carbonyl)-amino]-butyryl}-piperazine-1-carboxylic acid ethyl ester To a solution of 50 mg of 4-{(S)-4-tert-Butoxycarbonyl-2-[(5-carboxy-1-phenyl-1H-pyrazole-3-carbonyl)-amino]-butyryl}-piperazine-1-carboxylic acid ethyl ester in 3 ml of DCM, 0.1 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid.
Yield: 8 mg MS (ES+): m/e=502.

Example 79

4-((S)-4-Carboxy-2-{[5-(1-ethoxycarbonyl-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Bromo-propionic acid ethyl ester was used instead of 1-Bromo-cyclobutanecarboxylic acid ethyl ester. MS (ES$^+$): m/e=574.

Example 80

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid ethyl ester The title compound was prepared by adapting the procedures described in example 1 with the difference that 1-Bromo-3,3-dimethyl-butan-2-one was used instead of 1-Bromo-cyclobutanecarboxylic acid ethyl ester. MS (ES$^+$): m/e=572.

Example 81

4-((S)-4-Carboxy-2-{[5-((E)-3-ethoxycarbonyl-allyloxy)-1-phenyl-1H-pyrazole-3-carbonyl]-amino}-butyryl)-piperazine-1-carboxylic acid ethyl ester The title compound was prepared by adapting the procedures described in example 1 with the difference that (E)-4-Bromo-but-2-enoic acid ethyl ester was used instead of 1-Bromo-cyclobutanecarboxylic acid ethyl ester. MS (ES$^+$): m/e=586.

Example 82

4-((S)-4-Carboxy-2-{[5-(3-ethoxycarbonyl-2-oxo-propoxy)-1-phenyl-1H-pyrazole-3-carbonyl]-amino}-butyryl)-piperazine-1-carboxylic acid ethyl ester The title compound was prepared by adapting the procedures described in example 1 with the difference that 4-Bromo-3-ethoxy-but-2-enoic acid ethyl ester was used instead of 1-Bromo-cyclobutanecarboxylic acid ethyl ester. MS (ES$^+$): m/e=602.

Example 83

4-((S)-4-Carboxy-2-{[5-((E)-3-methoxycarbonyl-allyloxy)-1-phenyl-1H-pyrazole-3-carbonyl]-amino}-butyryl)-piperazine-1-carboxylic acid ethyl ester The title compound was prepared by adapting the procedures described in example 1 with the difference that (E)-4-Bromo-but-2-enoic acid methyl ester was used instead of 1-Bromo-cyclobutanecarboxylic acid ethyl ester. MS (ES$^+$): m/e=572.

Example 84

4-((S)-4-Carboxy-2-{[1-(2,5-difluoro-phenyl)-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that (2,5-Difluoro-phenyl)-hydrazine was used instead of (3-Methoxy-phenyl)-hydrazine. MS (ES$^+$): m/e=636.

Example 85

4-((S)-2-{[5-(1-Ethoxycarbonyl-cyclobutoxy)-1-phenyl-1H-pyrazole-3-carbonyl]-amino}-4-methanesulfonyl-butyryl)-piperazine-1-carboxylic acid ethyl ester (i) 4-((S)-2-tert-Butoxycarbonylamino-4-methanesulfonyl-butyryl)-piperazine-1-carboxylic acid ethyl ester To a solution of 2 g of (S)-2-tert-Butoxycarbonylamino-4-methanesulfonyl-butyric acid, 3.2 g of NEM and 2.3 g of TOTU in 10 ml of DMF, 1.2 g of piperazine-1-carboxylic acid ethyl ester was added at RT and stirred for 2 h. The reaction mixture was diluted with saturated aqueous sodium hydrogen carbonate solution and extracted with 400 ml of ethyl acetate. The organic phase was washed with diluted saturated aqueous sodium hydrogen carbonate solution and dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure.
Yield: 1.9 g.

(ii) 4-((S)-2-Amino-4-methanesulfonyl-butyryl)-piperazine-1-carboxylic acid ethyl ester To 1.9 g of 4-((S)-2-tert-Butoxycarbonylamino-4-methanesulfonyl-butyryl)-piperazine-1-carboxylic acid ethyl ester, 20 ml of methanolic hydrochloric acid was added at RT and stirred for 3 h. Then, 100 ml of toluene was added and the solvents were removed under reduced pressure. The product was obtained as its hydrochloric acid salt. Yield: 1.9 g.

(iii) 4-{(S)-2-[(5-Hydroxy-1-phenyl-1H-pyrazole-3-carbonyl)-amino]-4-methanesulfonyl-butyryl}-piperazine-1-carboxylic acid ethyl ester To a solution of 190 mg of 5-Hydroxy-1-phenyl-1H-pyrazole-3-carboxylic acid and 299 mg of 4-((S)-2-Amino-4-methanesulfonyl-butyryl)-piperazine-1-carboxylic acid ethyl ester in 3 ml of DMF, 142 mg of HOBT, 178 mg of EDC and 0.2 ml DIPEA was added and the reaction mixture was stirred for 16 h at RT. Then, the solvents were removed under reduced pressure and the crude product was purified by chromatography on silica gel eluting with a gradient of n-heptane/ethyl acetate. The fractions containing the product were combined and the solvent evaporated under reduced pressure. Yield: 327 mg.

(iv) 4-((S)-2-{[5-(1-Ethoxycarbonyl-cyclobutoxy)-1-phenyl-1H-pyrazole-3-carbonyl]-amino}-4-methanesulfonyl-butyryl)-piperazine-1-carboxylic acid ethyl ester To a solution of 100 mg of 4-{(S)-2-[(5-Hydroxy-1-phenyl-1H-pyrazole-3-carbonyl)-amino]-4-methanesulfonyl-butyryl}-piperazine-1-carboxylic acid ethyl ester in 2 ml of DMF, 127 mg of cesium carbonate and 81 mg of 1-Bromo-cyclobutanecarboxylic acid ethyl ester was added and heated to 100° C. for 2 h. Then, the reaction mixture was diluted with water and filtered through a Chem Elut® cartridge by eluting with ethyl acetate. The solvents were removed under reduced pressure. The residue was purified by preparative HPLC (C18 reverse phase column, elution with a water/MeCN gradient with 0.1% TFA). The fractions containing the product were evaporated and lyophilized to yield a white solid.
Yield: 20 mg MS (ES$^+$): m/e=634.

Example 86

4-((S)-4-Carboxy-2-{[1-cyclohexyl-5-(1-ethoxycarbonyl-cyclobutoxy)-1H-pyrazole-3-carbonyl]-amino}-butyryl)-piperazine-1-carboxylic acid ethyl ester The title compound was prepared by adapting the procedures described in example 12 with the difference that Cyclohexyl-hydrazine was used instead of (3-Methoxy-phenyl)-hydrazine. MS (ES$^+$): m/e=606.

Example 87

4-((S)-2-{[1-(3-Bromo-phenyl)-5-(1-ethoxycarbonyl-cyclobutoxy)-1H-pyrazole-3-carbonyl]-amino}-4-carboxy-butyryl)-piperazine-1-carboxylic acid ethyl ester The title compound was prepared by adapting the procedures described in example 12 with the difference that (3-Bromo-phenyl)-hydrazine was used instead of (3-Methoxy-phenyl)-hydrazine. MS (ES$^+$): m/e=679.

Example 88

4-{(S)-4-Carboxy-2-[(5-ethoxycarbonyl-1-phenyl-1H-pyrazole-3-carbonyl)-amino]-butyryl}-piperazine-1-carboxylic acid ethyl ester To a solution of 50 mg of 4-{(S)-4-tert-Butoxycarbonyl-2-[(5-carboxy-1-phenyl-1H-pyrazole-3-carbonyl)-amino]butyryl}-piperazine-1-carboxylic acid ethyl ester in 2 ml DCM, 25 mg of BOP-Cl, 20 mg of triethylamine and 5 mg of ethanol was added. Then, after stirring for 16 h at RT, the reaction mixture was concentrated under reduced pressure. The residue was purified by preparative HPLC (C18 reverse phase column, elution with a water/MeCN gradient with 0.1%

TFA). The fractions containing the product were evaporated and lyophilized to yield 13 mg of a white solid. This residue was dissolved in 1 ml of DCM, 0.2 ml of TFA was added at RT. After 4 h 20 ml of toluene was added and the solvents were removed under reduced pressure. The residue was dissolved in 3 ml of water and lyophilized to yield a white solid.

Yield: 6 mg MS (ES+): m/e=530.

Example 89

4-{(S)-4-Carboxy-2-[(5-dimethylcarbamoyl-1-phenyl-1H-pyrazole-3-carbonyl)-amino]-butyryl}-piperazine-1-carboxylic acid ethyl ester To a solution of 50 mg of 4-{(S)-4-tert-Butoxycarbonyl-2-[(5-carboxy-1-phenyl-1H-pyrazole-3-carbonyl)-amino]-butyryl}-piperazine-1-carboxylic acid ethyl ester in 2 ml DCM, 25 mg of BOP-Cl, 20 mg of triethylamine and 8 mg of dimethylamine hydrochloride was added. Then, after stirring for 16 h at RT, the reaction mixture was concentrated under reduced pressure. The residue was purified by preparative HPLC (C18 reverse phase column, elution with a water/MeCN gradient with 0.1% TFA). The fractions containing the product were evaporated and lyophilized to yield 16 mg of a white solid. This residue was dissolved in 1 ml of DCM, 0.2 ml of TFA was added at RT. After 4 h 20 ml of toluene was added and the solvents were removed under reduced pressure. The residue was dissolved in 3 ml of water and lyophilized to yield a white solid. Yield: 4 mg MS (ES+): m/e=529.

Example 90

4-{(S)-2-[(5-Carbamoyl-1-phenyl-1H-pyrazole-3-carbonyl)-amino]-4-carboxy-butyryl}-piperazine-1-carboxylic acid ethyl ester To a solution of 50 mg of 4-{(S)-4-tert-Butoxycarbonyl-2-[(5-carboxy-1-phenyl-1H-pyrazole-3-carbonyl)-amino]-butyryl}-piperazine-1-carboxylic acid ethyl ester in 2 ml DCM, 25 mg of BOP-Cl, 20 mg of triethylamine and 14 mg of ammonium bicarbonate was added. Then, after stirring for 16 h at RT, the reaction mixture was concentrated under reduced pressure. The residue was purified by preparative HPLC (C18 reverse phase column, elution with a water/MeCN gradient with 0.1% TFA). The fractions containing the product were evaporated and lyophilized to yield 47 mg of a white solid. This residue was dissolved in 1 ml of DCM, 0.2 ml of TFA was added at RT. After 4 h 20 ml of toluene was added and the solvents were removed under reduced pressure. The residue was dissolved in 3 ml of water and lyophilized to yield a white solid.

Yield: 6 mg MS (ES+): m/e=501.

Example 91

4-((S)-2-{[5-(Azetidine-1-carbonyl)-1-phenyl-1H-pyrazole-3-carbonyl]-amino}-4-carboxy-butyryl)-piperazine-1-carboxylic acid ethyl ester To a solution of 50 mg of 4-{(S)-4-tert-Butoxycarbonyl-2-[(5-carboxy-1-phenyl-1H-pyrazole-3-carbonyl)-amino]-butyryl}-piperazine-1-carboxylic acid ethyl ester in 2 ml DCM, 25 mg of BOP-Cl, 20 mg of triethylamine and 6 mg of azetidine was added. Then, after stirring for 16 h at RT, the reaction mixture was concentrated under reduced pressure. The residue was purified by preparative HPLC (C18 reverse phase column, elution with a water/MeCN gradient with 0.1% TFA). The fractions containing the product were evaporated and lyophilized to yield 64 mg of a white solid. This residue was dissolved in 1 ml of DCM, 0.2 ml of TFA was added at RT. After 4 h 20 ml of toluene was added and the solvents were removed under reduced pressure. The residue was dissolved in 3 ml of water and lyophilized to yield a white solid. Yield: 7 mg MS (ES+): m/e=541.

Example 92

4-((S)-2-{[5-(1-Carbamoyl-cyclobutoxy)-1-phenyl-1H-pyrazole-3-carbonyl]-amino}-4-carboxy-butyryl)-piperazine-1-carboxylic acid ethyl ester 50 mg of 4-((S)-4-Carboxy-2-{[5-(1-ethoxycarbonyl-cyclobutoxy)-1-phenyl-1H-pyrazole-3-carbonyl]-amino}-butyryl)-piperazine-1-carboxylic acid ethyl ester were dissolved in 1 ml of a 8 M solution of ammonia in methanol. After 16 h at RT the solvents were evaporated under reduced pressure and the residue was purified by preparative HPLC (C18 reverse phase column, elution with a water/MeCN gradient with 0.1% TFA). The fractions containing the product were evaporated and lyophilized to yield a white solid.

Yield: 13 mg MS (ES+): m/e=571.

Example 93

4-((S)-5-Carboxy-2-{[5-(1-ethoxycarbonyl-cyclobutoxy)-1-phenyl-1H-pyrazole-3-carbonyl]-amino}-pentanoyl)-piperazine-1-carboxylic acid ethyl ester (i) 4-((S)-2-Benzyloxycarbonylamino-5-tert-butoxycarbonyl-pentanoyl)-piperazine-1-carboxylic acid ethyl ester To a solution of 2 g of (S)-2-Benzyloxycarbonylamino-hexanedioic acid 6-tert-butyl ester dicyclohexyl-ammonium salt, 1.7 g of NEM and 1.2 g of TOTU in 6 ml of DMF, 0.62 g of piperazine-1-carboxylic acid ethyl ester was added at RT and stirred for 16 h. The reaction mixture was diluted saturated aqueous sodium hydrogen carbonate solution and extracted with 150 ml of ethyl acetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure.

Yield: 2.2 g.

(ii) 4-((S)-2-Amino-5-tert-butoxycarbonyl-pentanoyl)-piperazine-1-carboxylic acid ethyl ester A solution of 2.3 g of 4-((S)-2-Benzyloxycarbonylamino-5-tert-butoxycarbonyl-pentanoyl)-piperazine-1-carboxylic acid ethyl ester in 50 ml of ethanol was purged with argon. Then, 50 mg of Pd/C (5-10%) was added and the mixture stirred under a hydrogen atmosphere (3 bar). After 4 h the reaction mixture was filtered through a pad of celite and the solvents were removed under reduced pressure. After drying under reduced pressure the product was used in the subsequent reaction.

Yield: 1.7 g.

(iii) 4-{(S)-5-tert-Butoxycarbonyl-2-[(5-hydroxy-1-phenyl-1H-pyrazole-3-carbonyl)-amino]-pentanoyl}-piperazine-1-carboxylic acid ethyl ester To a solution of 171 mg of 5-Hydroxy-1-phenyl-1H-pyrazole-3-carboxylic acid and 300 mg of 4-((S)-2-Amino-5-tert-butoxycarbonyl-pentanoyl)-piperazine-1-carboxylic acid ethyl ester in 3 ml of DMF, 128 mg of HOBT and 160 mg of EDC was added and the reaction mixture was stirred for 5 h at RT. Then, the reaction mixture was diluted with water and filtered through a Chem Elut® cartridge by eluting with ethyl acetate. The solvents were removed under reduced pressure. The solid product was triturated with DCM and the precipitate was dried under reduced pressure. The crude product was used in the subsequent reaction.
Yield: 215 mg.

(iv) 4-((S)-5-Carboxy-2-{[5-(1-ethoxycarbonyl-cyclobutoxy)-1-phenyl-1H-pyrazole-3-carbonyl]-amino}-pentanoyl)-piperazine-1-carboxylic acid ethyl ester To a solution of 100 mg of 4-{(S)-5-tert-Butoxycarbonyl-2-[(5-hydroxy-1-phenyl-1H-pyrazole-3-carbonyl)-amino]-pentanoyl}-piperazine-1-carboxylic acid ethyl ester in 2 ml of DMF, 119 mg of cesium carbonate and 76 mg of 1-Bromo-cyclobutanecarboxylic acid ethyl ester was added and heated to 100° C. for 2 h. Then, the reaction mixture was diluted with water and filtered through a Chem Elut® cartridge by eluting with DCM. The solvents were removed under reduced pressure and the residue was dissolved in 1 ml of DCM, 0.2 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid.
Yield: 3 mg MS (ES+): m/e=614.

Example 94

4-((S)-4-Carboxy-2-{[5-(2-oxo-butoxy)-1-phenyl-1H-pyrazole-3-carbonyl]-amino}-butyryl)-piperazine-1-carboxylic acid ethyl ester The title compound was prepared by adapting the procedures described in example 1 with the difference that 1-Bromo-butan-2-one was used instead of 1-Bromo-cyclobutanecarboxylic acid ethyl ester. MS (ES+): m/e=544.

Example 95

4-((S)-4-Carboxy-2-{[5-(1-methyl-2-oxo-propoxy)-1-phenyl-1H-pyrazole-3-carbonyl]-amino}-butyryl)-piperazine-1-carboxylic acid ethyl ester The title compound was prepared by adapting the procedures described in example 1 with the difference that 3-Bromo-butan-2-one was used instead of 1-Bromo-cyclobutanecarboxylic acid ethyl ester. MS (ES+): m/e=544.

Example 96

4-((S)-4-Carboxy-2-{[5-(2-cyclopropyl-2-oxo-ethoxy)-1-phenyl-1H-pyrazole-3-carbonyl]-amino}-butyryl)-piperazine-1-carboxylic acid ethyl ester (i) 2-Bromo-1-cyclopropyl-ethanone To a solution of 985 mg of 1-Cyclopropyl-ethanone in 10 ml methanol, 1.9 g of bromine was added dropwise at 0° C. The reaction mixture was allowed to warm to RT and stirred for 1 h. The reaction mixture was diluted with water and extracted with diethylether (3×100 ml). The organic phase was dried over MgSO$_4$ and the solvents were removed under reduced pressure. The crude product was used for the subsequent alkylation reaction.

(ii) 4-((S)-4-Carboxy-2-{[5-(2-cyclopropyl-2-oxo-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Bromo-1-cyclopropyl-ethanone was used instead of 1-Bromo-cyclobutanecarboxylic acid ethyl ester. MS (ES+): m/e=556.

Example 97

4-[(S)-4-Carboxy-2-({5-[2-(1-methyl-cyclopropyl)-2-oxo-ethoxy]-1-phenyl-1H-pyrazole-3-carbonyl}-amino)-butyryl]-piperazine-1-carboxylic acid ethyl ester (i) 2-Bromo-1-(1-methyl-cyclopropyl)-ethanone To a solution of 1.1 g of 1-(1-Methyl-cyclopropyl)-ethanone in 10 ml methanol, 1.9 g of bromine was added dropwise at 0° C. The reaction mixture was allowed to warm to RT and stirred for 1 h. The reaction mixture was diluted with water and extracted with diethylether (3×100 ml). The organic phase was dried over MgSO$_4$ and the solvents were removed under reduced pressure. The crude product was used for the subsequent alkylation reaction.

(ii) 4-[(S)-4-Carboxy-2-({5-[2-(1-methyl-cyclopropyl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 1 with the difference that 2-Bromo-1-(1-methyl-cyclopropyl)-ethanone was used instead of 1-Bromo-cyclobutanecarboxylic acid ethyl ester. MS (ES+): m/e=570.

Example 98

4-((S)-4-Carboxy-2-{[5-(2-cyclobutyl-2-oxo-ethoxy)-1-phenyl-1H-pyrazole-3-carbonyl]-amino}-butyryl)-piperazine-1-carboxylic acid ethyl ester (i) 2-Bromo-1-cyclobutyl-ethanone To a solution of 1.0 g of 1-Cyclobutyl-ethanone in 10 ml methanol, 1.6 g of bromine was added dropwise at 0° C. The reaction mixture was allowed to warm to RT and stirred for 1 h. The reaction mixture was diluted with water and extracted with diethylether (3×100 ml). The organic phase was dried over MgSO$_4$ and the solvents were removed under reduced pressure. The crude product was used for the subsequent alkylation reaction.

(ii) 4-((S)-4-Carboxy-2-{[5-(2-cyclobutyl-2-oxo-ethoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Bromo-1-cyclobutyl-ethanone was used instead of 1-Bromo-cyclobutanecarboxylic acid ethyl ester. MS (ES$^+$): m/e=570.

Example 99

(S)-4-{[5-(3,3-Dimethyl-2-oxo-butoxy)-1-phenyl-1H-pyrazole-3-carbonyl]-amino}-5-oxo-5-[4-(2-oxo-2-pyrrolidin-1-yl-ethyl)-piperazin-1-yl]-pentanoic acid (i) (S)-2-[(5-Hydroxy-1-phenyl-1H-pyrazole-3-carbonyl)-amino]-pentanedioic acid 5-tert-butyl ester 1-methyl ester To a solution of 8 g of 5-Hydroxy-1-phenyl-1H-pyrazole-3-carboxylic acid and 10 g of (S)-2-Amino-pentanedioic acid 5-tert-butyl ester hydrochloride in 300 ml of DCM, 16 g of triethylamine and 15 g of HATU was added and stirred for 16 h at RT. Then, the reaction mixture was diluted with water and extracted with DCM. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 11 g.

(ii) (S)-2-{[5-(3,3-Dimethyl-2-oxo-butoxy)-1-phenyl-1H-pyrazole-3-carbonyl]-amino}-pentanedioic acid 5-tert-butyl ester 1-methyl ester A solution of 6.5 g of (S)-2-[(5-Hydroxy-1-phenyl-1H-pyrazole-3-carbonyl)-amino]-pentanedioic acid 5-tert-butyl ester 1-methyl ester in 175 ml of DMF was cooled to 0° C. Then, 644 mg of sodium hydride (60% in mineral oil) was added portionwise over 20 min. Further 20 min after completion of the addition 2.9 g of 1-Bromo-3,3-dimethyl-butan-2-one was added and the reaction mixture was allowed to warm to RT. After striring for 16 h the reaction mixture was diluted with brine and extracted with DCM. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 3.3 g.

(iii) (S)-2-{[5-(3,3-Dimethyl-2-oxo-butoxy)-1-phenyl-1H-pyrazole-3-carbonyl]-amino}-pentanedioic acid 5-tert-butyl ester To a solution of 3.4 g of (S)-2-{[5-(3,3-Dimethyl-2-oxo-butoxy)-1-phenyl-1H-pyrazole-3-carbonyl]-amino}-pentanedioic acid 5-tert-butyl ester 1-methyl ester in 15 ml of THF, 6.5 ml of a 1 M aqueous NaOH solution was added. After stirring at RT upon completion of the reaction the mixture was acidified to pH 2 with diluted aqueous hydrochloric acid and extracted with DCM (3×100 ml). The combined organic phases were dried over MgSO$_4$ and the solvents were removed under reduced pressure to yield a crystalline solid. Yield: 3.4 g (iv) (S)-4-{[5-(3,3-Dimethyl-2-oxo-butoxy)-1-phenyl-1H-pyrazole-3-carbonyl]-amino}-5-oxo-5-[4-(2-oxo-2-pyrrolidin-1-yl-ethyl)-piperazin-1-yl]-pentanoic acid To a solution of 80 mg of (S)-2-{[5-(3,3-Dimethyl-2-oxo-butoxy)-1-phenyl-1H-pyrazole-3-carbonyl]-amino}-pentanedioic acid 5-tert-butyl ester and 32 mg of 2-piperazin-1-yl-1-pyrrolidin-1-yl-ethanone in 1 ml of DMF, 25 mg of HOBT and 31 mg of EDC was added and the reaction mixture was stirred for 16 h at RT. Then, the reaction mixture was diluted with water and filtered through a Chem Elut® cartridge by eluting with DCM. The solvents were removed under reduced pressure. The residue was dissolved in 1 ml of DCM, 0.2 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt.
Yield: 54 mg MS (ES+): m/e=611.

Example 100

(S)-5-(4-Benzoyl-piperazin-1-yl)-4-{[5-(3,3-dimethyl-2-oxo-butoxy)-1-phenyl-1H-pyrazole-3-carbonyl]-amino}-5-oxo-pentanoic acid The title compound was prepared by adapting the procedures described in example 99 with the difference that Phenyl-piperazin-1-yl-methanone was used instead of 2-piperazin-1-yl-1-pyrrolidin-1-yl-ethanone. MS (ES$^+$): m/e=604.

Example 101

(S)-4-{[5-(3,3-Dimethyl-2-oxo-butoxy)-1-phenyl-1H-pyrazole-3-carbonyl]-amino}-5-oxo-5-[4-(4-trifluoromethyl-pyridin-2-yl)-piperazin-1-yl]-pentanoic acid The title compound was prepared by adapting the procedures described in example 99 with the difference that 1-(4-Trifluoromethyl-pyridin-2-yl)-piperazine was used instead of 2-piperazin-1-yl-1-pyrrolidin-1-yl-ethanone. MS (ES$^+$): m/e=645.

Example 102

4-((S)-2-{[5-(1-Ethoxycarbonyl-cyclobutoxy)-1-phenyl-1H-pyrazole-3-carbonyl]-amino}-4-methoxycarbonyl-butyryl)-piperazine-1-carboxylic acid ethyl ester To 30 mg of 4-((S)-4-Carboxy-2-{[5-(1-ethoxycarbonyl-cyclobutoxy)-1-phenyl-1H-pyrazole-3-carbonyl]-amino}-butyryl)-piperazine-1-carboxylic acid ethyl ester, 2 ml of methanolic hydrochloric acid was added at RT and stirred for 3 h. Then, 10 ml of toluene was added and the solvents were

Example 103

4-((S)-4-Carboxy-2-{[1-phenyl-5-(3,4,4-trifluoro-but-3-enyloxy)-1H-pyrazole-3-carbonyl]-amino}-butyryl)-piperazine-1-carboxylic acid ethyl ester The title compound was prepared by adapting the procedures described in example 1 with the difference that 4-Bromo-1,1,2-trifluoro-but-1-ene was used instead of 1-Bromo-cyclobutanecarboxylic acid ethyl ester. MS (ES+): m/e=582.

Example 104

4-((S)-4-Carboxy-2-{[5-(1-ethoxycarbonyl-butoxy)-1-phenyl-1H-pyrazole-3-carbonyl]-amino}-butyryl)-piperazine-1-carboxylic acid ethyl ester The title compound was prepared by adapting the procedures described in example 1 with the difference that 2-Bromo-pentanoic acid ethyl ester was used instead of 1-Bromo-cyclobutanecarboxylic acid ethyl ester. MS (ES+): m/e=602.

Example 105

(S)-5-[4-(3,5-Dimethoxy-phenyl)-piperazin-1-yl]-4-{[5-(3,3-dimethyl-2-oxo-butoxy)-1-phenyl-1H-pyrazole-3-carbonyl]-amino}-5-oxo-pentanoic acid The title compound was prepared by adapting the procedures described in example 99 with the difference that 1-(3,5-Dimethoxy-phenyl)-piperazine was used instead of 2-piperazin-1-yl-1-pyrrolidin-1-yl-ethanone. MS (ES+): m/e=636.

Example 106

4-((S)-4-Carboxy-2-{[5-(3,3-dimethyl-2-oxo-butoxy)-1-phenyl-1H-pyrazole-3-carbonyl]-amino}-butyryl)-[1,4]diazepane-1-carboxylic acid ethyl ester The title compound was prepared by adapting the procedures described in example 99 with the difference that [1,4] Diazepane-1-carboxylic acid ethyl ester was used instead of 2-piperazin-1-yl-1-pyrrolidin-1-yl-ethanone. MS (ES+): m/e=586.

Example 107

(S)-4-{[5-(3,3-Dimethyl-2-oxo-butoxy)-1-phenyl-1H-pyrazole-3-carbonyl]-amino}-5-(4-ethoxycarbonylmethyl-piperidin-1-yl)-5-oxo-pentanoic acid The title compound was prepared by adapting the procedures described in example 99 with the difference that Piperidin-4-yl-acetic acid ethyl ester was used instead of 2-piperazin-1-yl-1-pyrrolidin-1-yl-ethanone. MS (ES+): m/e=585.

Example 108

(S)-4-{[5-(3,3-Dimethyl-2-oxo-butoxy)-1-phenyl-1H-pyrazole-3-carbonyl]-amino}-5-oxo-5-(4-m-tolyl-piperidin-1-yl)-pentanoic acid The title compound was prepared by adapting the procedures described in example 99 with the difference that 4-m-Tolyl-piperidine was used instead of 2-piperazin-1-yl-1-pyrrolidin-1-yl-ethanone. MS (ES+): m/e=589.

Example 109

(S)-4-{[5-(3,3-Dimethyl-2-oxo-butoxy)-1-phenyl-1H-pyrazole-3-carbonyl]-amino}-5-oxo-5-(4-phenylsulfanyl-piperidin-1-yl)-pentanoic acid The title compound was prepared by adapting the procedures described in example 99 with the difference that 4-Phenylsulfanyl-piperidine was used instead of 2-piperazin-1-yl-1-pyrrolidin-1-yl-ethanone. MS (ES+): m/e=607.

Example 118

5-(5-{(S)-3-Carboxy-1-[4-(3-trifluoromethyl-phenyl)-piperazine-1-carbonyl]-propylcarbamoyl}-2-phenyl-2H-pyrazol-3-yloxymethyl)-furan-2-carboxylic acid methyl ester (i) (S)-4-Benzyloxycarbonylamino-5-oxo-5-[4-(3-trifluoromethyl-phenyl)-piperazin-1-yl]-pentanoic acid tert-butyl ester 2.53 g of (S)-2-Benzyloxycarbonylamino-pentanedioic acid 5-tert-butyl ester and 2.46 g of TOTU was dissolved in 15 ml of DMF. The, 3.29 ml of N-Methylmorpholine was added and the mixture was stirred for 30 min at RT. 1.72 g of 1-(3-Trifluoromethyl-phenyl)-piperazine was added and stirring was continued for 5 h. The mixture was diluted with ethyl acetate and washed with saturated sodium hydrogen carbonate solution. Drying of the organic phase over sodium sulfate and evaporation of the solvents under reduced pressure afforded a brownish powder that was purified by chromatography over silica gel eluting with ethyl acetate/heptane 1:2 to 100% ethyl acetate to give 7 g of the desired product.

Yield: 7 g MS (ES+): m/e=550.

(ii) (S)-4-Amino-5-oxo-5-[4-(3-trifluoromethyl-phenyl)-piperazin-1-yl]-pentanoic acid tert-butyl ester 7 g of (S)-4-Benzyloxycarbonylamino-5-oxo-5-[4-(3-trifluoromethyl-phenyl)-piperazin-1-yl]-pentanoic acid tert-butyl ester were dissolved in 120 ml of EtOH and 70 mg of Pd/C 10% was added. Hydrogenation under 3 bar of hydrogen was continued until full conversion of the reaction was obtained. After filtration of the catalyst all volatiles were evaporated under reduced pressure to give 4.4 g of the desired product.

Yield: 4.4 g MS (ES+): m/e=416.

(iii) (S)-4-[(5-Hydroxy-1-phenyl-1H-pyrazole-3-carbonyl)-amino]-5-oxo-5-[4-(3-trifluoromethyl-phenyl)piperazin-1-yl]-pentanoic acid tert-butyl ester To 2.2 g of (S)-4-Amino-5-oxo-5-[4-(3-trifluoromethyl-phenyl)-piperazin-1-yl]-pentanoic acid tert-butyl ester in 30 ml of DMF, 892 mg of HOBT, 1.08 g of 5-Hydroxy-1-phenyl-1H-pyrazole-3-carboxylic acid 1.12 g EDC Hydrochlorid and 1.90 ml DIPEA was added. After 3 h at RT the mixture was diluted with ethyl acetate and washed with saturated sodium hydrogen carbonate solution. Drying of the organic layer over sodium sulfate and evaporation under reduced pressure afforded a brownish powder that was purified by chromatography over silica gel eluting with ethyl acetate/ heptane 1:1 to 100% ethyl acetate to give 2.7 g of the desired product. Yield: 2.7 g MS (ES+): m/e=416.

(iv) 5-(5-{(S)-3-tert-Butoxycarbonyl-1-[4-(3-trifluoromethyl-phenyl)-piperazine-1-carbonyl]-propylcarbamoyl}-2-phenyl-2H-pyrazol-3-yloxymethyl)-furan-2-carboxylic acid methyl ester 180 mg of (S)-4-[(5-Hydroxy-1-phenyl-1H-pyrazole-3-carbonyl)-amino]-5-oxo-5-[4-(3-trifluoromethyl-phenyl) piperazin-1-yl]-pentanoic acid tert-butyl ester dissolved in 4 ml DMF was treated with 293 mg of cesium carbonate and 78 mg of Methyl-5-(chlormethyl)furan-2-carboxylate. After 3 h at 70° C. the mixture was diluted with ethyl acetate and washed with saturated sodium hydrogen carbonate solution. Drying of the organic layer over sodium sulfate gave crude 5-(5-{(S)-3-tert-Butoxycarbonyl-1-[4-(3-trifluoromethyl-phenyl)-piperazine-1-carbonyl]-propylcarbamoyl}-2-phenyl-2H-pyrazol-3-yloxymethyl)-furan-2-carboxylic acid methyl ester which was used for the subsequent reaction.

(v) 5-(5-{(S)-3-Carboxy-1-[4-(3-trifluoromethyl-phenyl)-piperazine-1-carbonyl]-propylcarbamoyl}-2-phenyl-2H-pyrazol-3-yloxymethyl)-furan-2-carboxylic acid methyl ester The crude 5-(5-{(S)-3-tert-Butoxycarbonyl-1-[4-(3-trifluoromethyl-phenyl)-piperazine-1-carbonyl]-propylcarbamoyl}-2-phenyl-2H-pyrazol-3-yloxymethyl)-furan-2-carboxylic acid methyl ester was dissolved in a mixture of 2 ml of DCM and 1 ml of TFA. After 2 h at RT all volatiles were removed under reduced pressure and the residue was purified by preparative HPLC (C18 reverse phase column, elution with a water/MeCN gradient with 0.1% TFA). The fractions containing the product were evaporated and lyophilized to yield a white solid.
Yield: 20 mg MS (ES+): m/e=684.

Example 120

(S)-4-{[5-(5-Methyl-isoxazol-3-ylmethoxy)-1-phenyl-1H-pyrazole-3-carbonyl]-amino}-5-oxo-5-[4-(3-trifluoromethyl-phenyl)-piperazin-1-yl]-pentanoic acid The title compound was prepared by adapting the procedures described in example 118 with the difference that 3-Chloromethyl-5-methyl-isoxazole was used instead of Methyl-5-(chloromethyl)furan-2-carboxylate. Yield: 43 mg MS (ES+): m/e=641.

Example 121

(S)-4-[(5-Carbamoylmethoxy-1-phenyl-1H-pyrazole-3-carbonyl)-amino]-5-oxo-5-[4-(3-trifluoromethyl-phenyl)-piperazin-1-yl]-pentanoic acid The title compound was prepared by adapting the procedures described in example 118 with the difference that 2-Bromoacteamide was used instead of Methyl-5-(chloromethyl)furan-2-carboxylate. Yield: 25 mg MS (ES+): m/e=603.

Example 122

(S)-4-[(5-Cyclopropylmethoxy-1-phenyl-1H-pyrazole-3-carbonyl)-amino]-5-oxo-5-[4-(3-trifluoromethyl-phenyl)-piperazin-1-yl]-pentanoic acid The title compound was prepared by adapting the procedures described in example 118 with the difference that Cyclopropylmethylbromide was used instead of Methyl-5-(chloromethyl)furan-2-carboxylate. Yield: 39 mg MS (ES+): m/e=600.

Example 123

(S)-4-[(5-Cyclobutylmethoxy-1-phenyl-1H-pyrazole-3-carbonyl)-amino]-5-oxo-5-[4-(3-trifluoromethyl-phenyl)-piperazin-1-yl]-pentanoic acid The title compound was prepared by adapting the procedures described in example 118 with the difference that Cyclobutylmethylbromide was used instead of Methyl-5-(chloromethyl)furan-2-carboxylate. Yield: 37 mg MS (ES+): m/e=614.

Example 124

1-(5-{(S)-3-Carboxy-1-[4-(3-trifluoromethyl-phenyl)-piperazine-1-carbonyl]-propylcarbamoyl}-2-phenyl-2H-pyrazol-3-yloxy)-cyclobutanecarboxylic acid ethyl ester The title compound was prepared by adapting the procedures described in example 118 with the difference that 1-Bromo-cyclobutanecarboxylic acid ethyl ester was used instead of Methyl-5-(chloromethyl)furan-2-carboxylate. Yield: 20 mg
MS (ES+): m/e=614.

Example 126

(S)-4-{[5-(3,3-Dimethyl-2-oxo-butoxy)-1-phenyl-1H-pyrazole-3-carbonyl]-amino}-5-oxo-5-[4-(2-oxo-2-pyrrolidin-1-yl-ethyl)-piperazin-1-yl]-pentanoic acid (i) 5-(3,3-Dimethyl-2-oxo-butoxy)-1-phenyl-1H-pyrazole-3-carboxylic acid To a solution of 5 g 5-Hydroxy-1-phenyl-1H-pyrazole-3-carboxylic acid ethyl ester in 12 ml of DMF was added at 0° C. 1.29 g of sodium hydride (60% in mineral oil). After 15 min at this temperature 3.85 g of 1-Bromo-3,3-dimethyl-butan-2-one were added. After 2 h at RT the mixture was poured on ice/water and extracted with ethyl acetate. The organic phase was washed with brine and dried over sodium sulfate followed by evaporation. The residue was taken up in 20 ml of THF and treated with 21.5 ml of 2M NaOH. After 2 h, additional 15 ml 2M NaOH were added. Finally, after 3 h the THF was evaporated and the residue acidified with 2M HCl resulting in the precipitation of a gum. The gum was dissolved in ethyl acetate and coevaporated with toluene. Stirring in ethyl acetate/hepatne 1:1 gave a gummy substance which solidified on evaporation.
MS (ES+): m/e=303.

(ii) (S)-4-tert-Butoxycarbonylamino-5-[4-(3,5-dimethyl-phenyl)-piperazin-1-yl]-5-oxo-pentanoic acid tert-butyl ester 75 mg of Boc-Glu(OtBu)—OH and 44 mg HOBT was dissolved in 1 ml of DMF. 52 mg of 1-(3,5-Dimethyl-phenyl)-piperazine and 97 mg of DIPEA in 1 ml of DMF was added, followed by 43 mg of EDC in 0.5 ml of DMF. The mixture was stirred for 16 h at RT (closed tube). The mixture was filtered, and the filter was washed with 20 ml ethyl acetate in

(iii) (S)-4-Amino-5-[4-(3,5-dimethyl-phenyl)-piperazin-1-yl]-5-oxo-pentanoic acid The crude product from the previous step (ii) was dissolved in 2 ml of DCM/TFA 3:1 and stirred at RT for 16 h. The solvents were evaporated under reduced pressure and the residue was dried for 16 h at 10 mbar in a vacuum drying cabinet.

(iv) (S)-4-{[5-(3,3-Dimethyl-2-oxo-butoxy)-1-phenyl-1H-pyrazole-3-carbonyl]-amino}-5-[4-(3,5-dimethyl-phenyl)-piperazin-1-yl]-5-oxo-pentanoic acid 75 mg of 5-(3,3-Dimethyl-2-oxo-butoxy)-1-phenyl-1H-pyrazole-3-carboxylic acid, 44 mg of HOBt and 129 mg of DIPEA was dissolved in 1 ml of DMF. 43 mg of EDC in 0.5 ml of DMF was added and the mixture was stirred for 30 min at RT. The crude product from the previous step (iii) in 0.5 ml of DMF was added and the mixture was stirred for 16 h at RT. After filtration with syringe filter the filtrate was directly purified by preparative HPLC (C18 reverse phase column, elution with a water/MeCN gradient with 0.1% TFA). The fractions containing the product were evaporated and lyophilized to yield a white solid.
Yield: 30 mg MS (ES+): m/e=604.

Example 127

(S)-5-[4-(3-Chloro-benzoyl)-piperidin-1-yl]-4-{[5-(3,3-dimethyl-2-oxo-butoxy)-1-phenyl-1H-pyrazole-3-carbonyl]-amino}-5-oxo-pentanoic acid The title compound was prepared by adapting the procedures described in example 126 with the difference that (3-Chloro-phenyl)-piperidin-4-yl-methanone was used instead of 1-(3,5-Dimethyl-phenyl)-piperazine. Yield: 22 mg MS (ES+): m/e=637.

Example 128

(S)-5-[4-(3,4-Difluoro-benzoyl)-piperidin-1-yl]-4-{[5-(3,3-dimethyl-2-oxo-butoxy)-1-phenyl-1H-pyrazole-3-carbonyl]-amino}-5-oxo-pentanoic acid The title compound was prepared by adapting the procedures described in example 126 with the difference that (3,4-Difluoro-phenyl)-piperidin-4-yl-methanone was used instead of 1-(3,5-Dimethyl-phenyl)-piperazine. Yield: 27 mg MS (ES+): m/e=639.

Example 129

(S)-4-{[5-(3,3-Dimethyl-2-oxo-butoxy)-1-phenyl-1H-pyrazole-3-carbonyl]-amino}-5-[4-(6-fluoro-benzo[d]isoxazol-3-yl)-piperidin-1-yl]-5-oxo-pentanoic acid The title compound was prepared by adapting the procedures described in example 126 with the difference that 6-Fluoro-3-piperidin-4-yl-benzo[d]isoxazole was used instead of 1-(3,5-Dimethyl-phenyl)-piperazine. Yield: 27 mg MS (ES+): m/e=634.

Example 130

(S)-5-(4-Acetyl-4-phenyl-piperidin-1-yl)-4-{[5-(3,3-dimethyl-2-oxo-butoxy)-1-phenyl-1H-pyrazole-3-carbonyl]-amino}-5-oxo-pentanoic acid The title compound was prepared by adapting the procedures described in example 126 with the difference that 1-(4-Phenyl-piperidin-4-yl)-ethanone was used instead of 1-(3,5-Dimethyl-phenyl)-piperazine. Yield: 28 mg MS (ES+): m/e=617.

Example 131

1-((S)-4-Carboxy-2-{[5-(3,3-dimethyl-2-oxo-butoxy)-1-phenyl-1H-pyrazole-3-carbonyl]-amino}-butyryl)-piperidine-4-carboxylic acid ethyl ester The title compound was prepared by adapting the procedures described in example 126 with the difference that Piperidine-4-carboxylic ethyl ester was used instead of 1-(3,5-Dimethyl-phenyl)-piperazine. Yield: 30 mg MS (ES+): m/e=571.

Example 132

(S)-5-[4-(4,6-Dimethoxy-pyrimidin-2-yl)-piperidin-1-yl]-4-{[5-(3,3-dimethyl-2-oxo-butoxy)-1-phenyl-1H-pyrazole-3-carbonyl]-amino}-5-oxo-pentanoic acid The title compound was prepared by adapting the procedures described in example 126 with the difference that 4,6-Dimethoxy-2-piperidin-4-yl-pyrimidine was used instead of 1-(3,5-Dimethyl-phenyl)-piperazine. Yield: 26 mg
MS (ES+): m/e=637.

Example 133

4-((S)-2-{[5-(3,3-Dimethyl-2-oxo-butoxy)-1-phenyl-1H-pyrazole-3-carbonyl]-amino}-3-methoxycarbonylamino-propionyl)-piperazine-1-carboxylic acid ethyl ester

(i) 4-((S)-2-Benzyloxycarbonylamino-3-tert-butoxycarbonylamino-propionyl)-piperazine-1-carboxylic acid ethyl ester To a solution of 5 g of (S)-2-Benzyloxycarbonylamino-3-tert-butoxycarbonylamino-propionic acid, 3 g of triethylamine, 2.2 g of HOBT and 2.8 g of EDC in 50 ml of DCM, 2.3 g of piperazine-1-carboxylic acid ethyl ester was added at RT and stirred for 16 h. The reaction mixture was then diluted with water and then extracted with 300 ml of DCM. The organic phase was washed with diluted saturated aqueous sodium hydrogen carbonate solution and dried over MgSO$_4$. The solvents were removed under reduced pressure. The crude product was subjected to the next reaction step without further purification.
Yield: 10.7 g.

(ii) 4-((S)-2-Amino-3-tert-butoxycarbonylamino-propionyl)-piperazine-1-carboxylic acid ethyl ester A solution of 10.7 g of 4-((S)-2-Benzyloxycarbonylamino-3-tert-butoxycarbonylamino-propionyl)-piperazine-1-carboxylic acid ethyl ester in 100 ml of ethanol was purged with argon. Then, 1 g of Pd/C (5-10%) was added and the mixture stirred under a hydrogen atmosphere (3 bar). After 16 h the reaction mixture was filtered through a pad of celite and the solvents were removed under reduced pressure. After drying under reduced pressure the product was used in the subsequent reaction.

Yield: 5.6 g.

(iii) 4-((S)-3-tert-Butoxycarbonylamino-2-{[5-(3,3-dimethyl-2-oxo-butoxy)-1-phenyl-1H-pyrazole-3-carbonyl]-amino}-propionyl)-piperazine-1-carboxylic acid ethyl ester To a solution of 1.7 g of 5-(3,3-Dimethyl-2-oxo-butoxy)-1-phenyl-1H-pyrazole-3-carboxylic acid and 2.0 g of 4-((S)-2-Amino-3-tert-butoxycarbonylamino-propionyl)-piperazine-1-carboxylic acid ethyl ester in 10 ml of DMF, 0.9 g of HOBT and 1.1 g of EDC was added and the reaction mixture was stirred for 2 h at RT. Then, the reaction mixture was diluted with water and extracted with DCM. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 3.8 g.

(iv) 4-((S)-3-Amino-2-{[5-(3,3-dimethyl-2-oxo-butoxy)-1-phenyl-1H-pyrazole-3-carbonyl]-amino}-propionyl)-piperazine-1-carboxylic acid ethyl ester To a solution of 3.8 g of 4-((S)-3-tert-Butoxycarbonylamino-2-{[5-(3,3-dimethyl-2-oxo-butoxy)-1-phenyl-1H-pyrazole-3-carbonyl]-amino}-propionyl)-piperazine-1-carboxylic acid ethyl ester in 10 ml of DCM, 2.4 ml of TFA was added at RT. After 4 h 20 ml of toluene was added and the solvents were removed under reduced pressure. The product was obtained as its trifluoroacetate salt. Yield: 6.4 g.

(v) 4-((S)-2-{[5-(3,3-Dimethyl-2-oxo-butoxy)-1-phenyl-1H-pyrazole-3-carbonyl]-amino}-3-methoxycarbonylamino-propionyl)-piperazine-1-carboxylic acid ethyl ester To a solution of 100 mg of 4-((S)-3-Amino-2-{[5-(3,3-dimethyl-2-oxo-butoxy)-1-phenyl-1H-pyrazole-3-carbonyl]-amino}-propionyl)-piperazine-1-carboxylic acid ethyl ester trifluoroacetate in 2 ml DCM and 0.1 ml triethylamine, 20 mg methyl chloroformate was added at RT. After stirring for 4 h, the reaction mixture was concentrated under reduced pressure and purified by preparative HPLC (C18 reverse phase column, elution with a water/MeCN gradient with 0.1% TFA). The fractions containing the product were evaporated and lyophilized to yield a white solid. Yield: 19 mg
MS (ES$^+$): m/e=587.

Example 134

4-[(S)-2-{[5-(3,3-Dimethyl-2-oxo-butoxy)-1-phenyl-1H-pyrazole-3-carbonyl]-amino}-3-(oxalyl-amino)-propionyl]-piperazine-1-carboxylic acid ethyl ester (i) 4-[(S)-2-{[5-(3,3-Dimethyl-2-oxo-butoxy)-1-phenyl-1H-pyrazole-3-carbonyl]-amino}-3-(methoxyoxalyl-amino)-propionyl]-piperazine-1-carboxylic acid ethyl ester To a solution of 100 mg of 4-((S)-3-Amino-2-{[5-(3,3-dimethyl-2-oxo-butoxy)-1-phenyl-1H-pyrazole-3-carbonyl]-amino}-propionyl)-piperazine-1-carboxylic acid ethyl ester trifluoroacetate in 2 ml DCM and 0.1 ml triethylamine, 23 mg Chloro-oxo-acetic acid methyl ester was added at RT. After stirring for 4 h, the reaction mixture was concentrated under reduced pressure and purified by preparative HPLC (C18 reverse phase column, elution with a water/MeCN gradient with 0.1% TFA). The fractions containing the product were evaporated and lyophilized to yield a white solid. Yield: 34 mg.

(ii) 4-[(S)-2-{[5-(3,3-Dimethyl-2-oxo-butoxy)-1-phenyl-1H-pyrazole-3-carbonyl]-amino}-3-(oxalyl-amino)-propionyl]-piperazine-1-carboxylic acid ethyl ester To a solution of 34 mg 4-[(S)-2-{[5-(3,3-Dimethyl-2-oxo-butoxy)-1-phenyl-1H-pyrazole-3-carbonyl]-amino}-3-(methoxyoxalyl-amino)-propionyl]-piperazine-1-carboxylic acid ethyl ester in 2 ml of THF, 0.2 ml of a 1 M aqueous NaOH solution was added. After stirring for 5 h at RT the reaction was acidified to pH 1 with diluted aqueous hydrochloric acid and extracted with DCM (3×50 ml). The combined organic phases were dried over MgSO$_4$ and the solvents were removed under reduced pressure. The product was dissolved in water and lyophilized to yield a white solid. Yield: 13 mg
MS (ES+): m/e=601.

Example 135

4-[(S)-2-{[5-(3,3-Dimethyl-2-oxo-butoxy)-1-phenyl-1H-pyrazole-3-carbonyl]-amino}-3-(2-ethoxy-3,4-dioxo-cyclobut-1-enylamino)-propionyl]-piperazine-1-carboxylic acid ethyl ester To a solution of 100 mg of 4-((S)-3-Amino-2-{[5-(3,3-dimethyl-2-oxo-butoxy)-1-phenyl-1H-pyrazole-3-carbonyl]-amino}-propionyl)-piperazine-1-carboxylic acid ethyl ester trifluoroacetate in 2 ml DCM and 0.1 ml triethylamine, 32 mg 3,4-Diethoxy-cyclobut-3-ene-1,2-dione was added at RT. After stirring for 6 h, the reaction mixture was concentrated under reduced pressure and purified by preparative HPLC (C18 reverse phase column, elution with a water/MeCN gradient with 0.1% TFA). The fractions containing the product were evaporated and lyophilized to yield a white solid.

Yield: 10 mg MS (ES+): m/e=653.

Example 136

4-[(S)-2-{[5-(3,3-Dimethyl-2-oxo-butoxy)-1-phenyl-1H-pyrazole-3-carbonyl]-amino}-3-(2-hydroxy-3,4-dioxo-cyclobut-1-enylamino)-propionyl]-piperazine-1-carboxylic acid ethyl ester To a solution of 40 mg 4-[(S)-2-{[5-(3,3-Dimethyl-2-oxo-butoxy)-1-phenyl-1H-pyrazole-3-carbonyl]-amino}-3-(2-ethoxy-3,4-dioxo-cyclobut-1-enylamino)-propionyl]-piperazine-1-carboxylic acid ethyl ester in 2 ml of THF, 0.2 ml of a 1 M aqueous NaOH solution was added. After stirring for 5 h at RT the reaction was acidified to pH 1 with diluted aqueous hydrochloric acid and extracted with DCM (3×50 ml). The combined organic phases were dried over MgSO$_4$ and the solvents were removed under reduced pressure. The product was dissolved in water and lyophilized to yield a white solid.

Yield: 6 mg MS (ES+): m/e=625.

Example 137

4-[(S)-4-Carboxy-2-({5-[(1-carboxy-1-methyl-ethyl-carbamoyl)-methoxy]-1-phenyl-1H-pyrazole-3-carbonyl}-amino)-butyryl]-piperazine-1-carboxylic acid ethyl ester

(i) 4-{(S)-4-tert-Butoxycarbonyl-2-[(5-hydroxy-1-phenyl-1H-pyrazole-3-carbonyl)-amino]butyryl}-piperazine-1-carboxylic acid ethyl ester To a solution of 7.2 g 1-phenyl-3-carboxy-5-pyrazolone and 12.1 g 4-((S)-2-amino-4-tert-butoxycarbonyl-butyryl)-piperazine-1-carboxylic acid ethyl ester (prepared as described earlier) in 100 ml DMF 5.4 g HOBT and 6.7 g EDC were added and the reaction mixture was stirred for 12 h at RT. Then the reaction mixture was diluted with ethyl acetate and subsequently extracted with aqueous LiCl (4% w/w), 0.1 M HCl and aqueous NaHCO$_3$. The organic layer was dried over MgSO$_4$ and the solvent was removed under reduced pressure. The crude product thus obtained was used in the subsequent reaction.

Yield: 14.8 g.

(ii) 4-{(S)-2-[(5-Benzyloxycarbonylmethoxy-1-phenyl-1H-pyrazole-3-carbonyl)-amino]-4-tert-butoxycarbonyl-butyryl}-piperazine-1-carboxylic acid ethyl ester To a solution of 14.5 g 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 110 ml DMF were added 4.5 ml benzyl bromoacetate and 17.8 g cesium carbonate. After stirring at RT for 12 h the solution was reduced to a volume of 50 ml, diluted with 400 ml ethyl acetate and extracted with aqueous LiCl (4% w/w). The crude product obtained after evaporation of the solvent was purified by flash chromatography on silica eluting with a gradient of n-heptane/ethyl acetate. Yield: 13.2 g yellowish amorphous solid.

(iii) 4-{(S)-4-tert-Butoxycarbonyl-2-[(5-carboxymethoxy-1-phenyl-1H-pyrazole-3-carbonyl)-amino]-butyryl}-piperazine-1-carboxylic acid ethyl ester To a solution of 13.2 g 4-{(S)-2-[(5-Benzyloxycarbonylmethoxy-1-phenyl-1H-pyrazole-3-carbonyl)-amino]-4-tert-butoxycarbonyl-butyryl}-piperazine-1-carboxylic acid ethyl ester in 75 ml ethyl acetate were added under argon 1.1 g Pd/C (10%) and the suspension was stirred under an atmosphere of hydrogen (3 bar) for 16 h. The suspension was filtered over a plug of Celite® and washed with ethyl acetate. The crude product obtained after evaporation of the solvent was dried under vacuo at 40° C. for 24 h.

Yield: 12.1 g colorless solid.

(iv) 4-[(S)-4-Carboxy-2-({5-[(1-carboxy-1-methyl-ethylcarbamoyl)-methoxy]-1-phenyl-1H-pyrazole-3-carbonyl}-amino)-butyryl]-piperazine-1-carboxylic acid ethyl ester To a solution of 100 mg 4-{(S)-4-tert-butoxycarbonyl-2-[(5-carboxymethoxy-1-phenyl-1H-pyrazole-3-carbonyl)-amino]-butyryl}-piperazine-1-carboxylic acid ethyl ester in 5 ml DMF were added 39 mg HOBt, 68 µl DIPEA and 41 mg 2-amino-2-methyl-propionic acid tert-butyl ester at RT. Then 49 mg EDC were added portionwise and the solution stirred over a period of 12 h. The solvent was evaporated, the residue dissolved in ethyl acetate and subsequently extracted with aqueous LiCl (4% w/w), 0.1 M HCl and aqueous NaHCO$_3$. The organic layer was dried over MgSO$_4$ and the solvent was removed under reduced pressure. The crude product thus obtained was dissolved in 2 ml DCM and treated with 500 µl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt.

Yield: 60 mg MS (ES+): m/e=617.

Example 138

4-[(S)-4-Carboxy-2-({5-[((S)-1-carboxy-ethylcarbamoyl)-methoxy]-1-phenyl-1H-pyrazole-3-carbonyl}-amino)-butyryl]-piperazine-1-carboxylic acid ethyl ester The title compound was prepared by adapting the procedures described in example 137 with the difference that L-alanine tert-butyl ester hydrochloride was used instead of 2-amino-2-methyl-propionic acid tert-butyl ester. Yield: 55 mg MS (ES+): m/e=603.

Example 139

4-[(S)-4-Carboxy-2-({5-[((R)-1-carboxy-ethylcarbamoyl)-methoxy]-1-phenyl-1H-pyrazole-3-carbonyl}-amino)-butyryl]-piperazine-1-carboxylic acid ethyl ester The title compound was prepared by adapting the procedures described in example 137 with the difference that D-alanine tert-butyl ester hydrochloride was used instead of 2-amino-2-methyl-propionic acid tert-butyl ester. Yield: 23 mg MS (ES$^+$): m/e=603.

Example 140

4-[(S)-4-Carboxy-2-({5-[(carboxymethyl-methyl-carbamoyl)-methoxy]-1-phenyl-1H-pyrazole-3-carbonyl}-amino)-butyryl]-piperazine-1-carboxylic acid ethyl ester The title compound was prepared by adapting the procedures described in example 137 with the difference that sarcosine tert-butyl ester hydrochloride was used instead of 2-amino-2-methyl-propionic acid tert-butyl ester.

Yield: 55 mg MS (ES+): m/e=603.

Example 141

4-{(S)-4-Carboxy-2-[(5-cyclopropylcarbamoyl-methoxy-1-phenyl-1H-pyrazole-3-carbonyl)-amino]-butyryl}-piperazine-1-carboxylic acid ethyl ester The title compound was prepared by adapting the procedures described in example 137 with the difference that cyclopropylamine was used instead of 2-amino-2-methyl-propionic acid tert-butyl ester. Yield: 40 mg MS (ES+): m/e=571.

Example 142

4-[(S)-4-Carboxy-2-({5-[(cyclopropylcarbamoylm-ethyl-carbamoyl)-methoxy]-1-phenyl-1H-pyrazole-3-carbonyl}-amino)-butyryl]-piperazine-1-carboxylic acid ethyl ester The title compound was prepared by adapting the procedures described in example 137 with the difference that 2-amino-N-cyclopropyl-acetamide trifluoroacetate was used instead of 2-amino-2-methyl-propionic acid tert-butyl ester. Yield: 38 mg MS (ES+): m/e=628.

Example 143

4-((S)-4-Carboxy-2-{[5-(1-cyclopropylcarbamoyl-1-methyl-ethoxy)-1-phenyl-1H-pyrazole-3-carbonyl]-amino}-butyryl)-piperazine-1-carboxylic acid ethyl ester (i) 4-((S)-4-tert-Butoxycarbonyl-2-{[5-(1-carboxy-1-methyl-ethoxy)-1-phenyl-1H-pyrazole-3-carbonyl]-amino}-butyryl)-piperazine-1-carboxylic acid ethyl ester To a solution of 1 g 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 100 ml DMF were subsequently added 646 µl methyl 2-bromoisobutyrate and 1.8 g cesium carbonate over a period of 4 h. After stirring at RT for 2 h the solution was acidified with 1 M HCl, diluted with 100 ml ethyl acetate and extracted with aqueous LiCl (4% w/w). The crude product obtained after evaporation of the solvent was purified by flash chromatography on silica eluting with a gradient of n-heptane/ethyl acetate yield the corresponding methyl ester as yellowish oil (710 mg). The ester was taken up in THF/MeOH/$H_2O$ 4/1/1 (6 ml) and treated with 45 mg LiOH at 0° C. After complete conversion it was acidified to pH5 and the reaction mixture was reduced. The crude product thus obtained (610 mg) was not further purified.

(ii) 4-((S)-4-Carboxy-2-{[5-(1-cyclopropylcarbamoyl-1-methyl-ethoxy)-1-phenyl-1H-pyrazole-3-carbonyl]-amino}-butyryl)-piperazine-1-carboxylic acid ethyl ester To a solution of 100 mg 4-((S)-4-tert-butoxycarbonyl-2-{[5-(1-carboxy-1-methyl-ethoxy)-1-phenyl-1H-pyrazole-3-carbonyl]-amino}-butyryl)-piperazine-1-carboxylic acid ethyl ester in 5 ml DMF were added 37 mg HOBt, 47 mg EDC and 65 µl DIPEA. After 20 minutes 17 µl cyclopropylamine were added and the mixture stirred at RT for 6 h. The solvent was evaporated, the residue dissolved in ethyl acetate and subsequently extracted with aqueous LiCl (4% w/w), 0.1 M HCl and aqueous $NaHCO_3$. The organic layer was dried over $MgSO_4$ and the solvent was removed under reduced pressure. The crude product was dissolved in 2.5 ml DCM and treated with 400 µl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt.

Yield: 50 mg MS (ES+): m/e=599.

Example 144

4-[(S)-4-Carboxy-2-({5-[1-(cyclopropylcarbamoyl-methyl-carbamoyl)-1-methyl-ethoxy]-1-phenyl-1H-pyrazole-3-carbonyl}-amino)-butyryl]-piperazine-1-carboxylic acid ethyl ester The title compound was prepared by adapting the procedures described in example 143 with the difference that 2-amino-N-cyclopropyl-acetamide trifluoroacetate was used instead of cyclopropylamine. Yield: 45 mg MS (ES+): m/e=656.

Example 145

4-((S)-4-Carboxy-2-{[5-(1-cyclopropylcarbamoyl-ethoxy)-1-phenyl-1H-pyrazole-3-carbonyl]-amino}-butyryl)-piperazine-1-carboxylic acid ethyl ester (i) 4-((S)-4-Carboxy-2-{[5-(1-carboxy-ethoxy)-1-phenyl-1H-pyrazole-3-carbonyl]-amino}-butyryl)piperazine-1-carboxylic acid ethyl ester To a solution of 1.50 g 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 12 ml DMF were added 670 µl ethyl 2-bromopropionate and 3.2 g cesium carbonate. After stirring at RT for 24 h the solution was diluted with ethyl acetate and extracted with aqueous LiCl (4% w/w). The crude product obtained after evaporation of the solvent was dissolved in THF and treated with 1 N NaOH. When conversion was complete (4 h) Amberlite IR-120® was added, the suspension filtrated and the filtrate evaporated to give the crude product (1.56 g)

(ii) 4-((S)-4-Carboxy-2-{[5-(1-cyclopropylcarbamoyl-ethoxy)-1-phenyl-1H-pyrazole-3-carbonyl]-amino}-butyryl)-piperazine-1-carboxylic acid ethyl ester To a solution of 100 mg 4-((S)-4-tert-butoxycarbonyl-2-{[5-(1-carboxy-ethoxy)-1-phenyl-1H-pyrazole-3-carbonyl]-amino}-butyryl)-piperazine-1-carboxylic acid ethyl ester in 2 ml DMF were added 38 mg HOBt, 47 mg EDC and 63 µl DIPEA. After 20 minutes 17 µl cyclopropylamine were added and the mixture stirred at RT for 16 h. Saturated $NaHCO_3$ solution (1.5 ml) was added and the mixture passed through a Chem Elute® cartridge eluting with DCM. The crude product obtained after evaporation of the solvent was dissolved in 1 ml DCM and treated with 100 µl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt.

Yield: 3 mg MS (ES+): m/e=585.

Example 146

4-[(S)-4-Carboxy-2-({5-[1-(cyclopropylcarbamoyl-methyl-carbamoyl)-ethoxy]-1-phenyl-1H-pyrazole-3-carbonyl}-amino)-butyryl]-piperazine-1-carboxylic acid ethyl ester The title compound was prepared by adapting the procedures described in example 145 with the difference that 2-amino-N-cyclopropyl-acetamide trifluoroacetate was used instead of cyclopropylamine. Yield: 2 mg MS (ES+): m/e=642.

Example 147

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid butyl ester (i) (S)-2-[(5-Hydroxy-1-phenyl-1H-pyrazole-3-carbonyl)-amino]-pentanedioic acid 5-tert-butyl ester 1-methyl ester To a solution of 12.1 g 1-phenyl-3-carboxy-5-pyrazolone, 15 g (S)-2-amino-pentanedioic acid 5-tert-butyl ester 1-methyl ester and 22.5 g HATU in 200 ml DCM were added 34 ml triethylamine. After 2 h the mixture was extracted with water and the crude product obtained after evaporation of the solvent reacted without further purification.

(ii) (S)-2-{[5-(3,3-Dimethyl-2-oxo-butoxy)-1-phenyl-1H-pyrazole-3-carbonyl]-amino}-pentanedioic acid 5-tert-butyl ester 1-methyl ester Crude (S)-2-[(5-Hydroxy-1-phenyl-1H-pyrazole-3-carbonyl)-amino]-pentanedioic acid 5-tert-butyl ester 1-methyl ester (44 g) was dissolved in DMF and treated with 12.2 g potassium tert-butoxide and 14.7 ml 1-bromopinacolone. After 2 h the solvent was removed in vacuo, the residue taken up in DCM and extracted with water. The crude product obtained after evaporation of the solvent was purified by flash column chromatography on silica eluting with heptane/ethyl acetate giving the title compound as colorless oil (45 g).

(iii) (S)-2-{[5-(3,3-Dimethyl-2-oxo-butoxy)-1-phenyl-1H-pyrazole-3-carbonyl]-amino}-pentanedioic acid 5-tert-butyl ester 1 M aqueous NaOH was added to a solution of 11.8 g (S)-2-{[5-(3,3-dimethyl-2-oxo-butoxy)-1-phenyl-1H-pyrazole-3-carbonyl]-amino}-pentanedioic acid 5-tert-butyl ester 1-methyl ester in 31 ml THF at RT. After 2 h 5 M HCl was added to bring the reaction mixture to pH 5. Extraction with DCM yielded the product as colorless solid (10.8 g).

(iv) 4-((S)-4-tert-Butoxycarbonyl-2-{[5-(3,3-dimethyl-2-oxo-butoxy)-1-phenyl-1H-pyrazole-3-carbonyl]-amino}-butyryl)-piperazine-1-carboxylic acid benzyl ester To a solution of 3.5 g (S)-2-{[5-(3,3-dimethyl-2-oxo-butoxy)-1-phenyl-1H-pyrazole-3-carbonyl]-amino}-pentanedioic acid 5-tert-butyl ester in 11 ml DMF were added 1.36 ml benzyl 1-piperazinecarboxylate, 3.61 ml N-ethylmorpholine and 2.3 g TOTU. After 2 h the reaction mixture was diluted with ethyl acetate and extracted with aqueous NaHCO$_3$ and aqueous LiCl (4% w/w). The crude product product obtained after evaporation of the solvent (4.4 g) was used in the subsequent reaction.

(v) (S)-4-{[5-(3,3-Dimethyl-2-oxo-butoxy)-1-phenyl-1H-pyrazole-3-carbonyl]-amino}-5-oxo-5-piperazin-1-yl-pentanoic acid tert-butyl ester To a solution of 4.4 g 4-((S)-4-tert-Butoxycarbonyl-2-{[5-(3,3-dimethyl-2-oxo-butoxy)-1-phenyl-1H-pyrazole-3-carbonyl]-amino}-butyryl)-piperazine-1-carboxylic acid benzyl ester in 40 ml ethanol were added 0.9 g Pd/C (10%) and the suspension stirred under an atmosphere of hydrogen (3 bar) for 24 h. It was filtrated, washed with ethanol and the solvent evaporated to give the title compound as colorless oil (4.1 g).

(vi) 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid butyl ester To a solution of 75 mg (S)-4-{[5-(3,3-Dimethyl-2-oxo-butoxy)-1-phenyl-1H-pyrazole-3-carbonyl]-amino}-5-oxo-5-piperazin-1-yl-pentanoic acid tert-butyl ester in 1.5 ml DCM were added 21 µl triethylamine and 19 µl butyl chloroformate at 0° C. The solution was allowed to warm to RT over 24 h before TFA (0.35 ml) was added. After stirring for 24 h the solvents were evaporated and the residue was purified by preparative HPLC (C18 reverse phase column, elution with a water/MeCN gradient with 0.1% TFA). The product was obtained as its trifluoroacetate salt. Yield: 40 mg MS (ES+): m/e=600.

Example 148

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid p-tolyl ester The title compound was prepared by adapting the procedures described in example 147 with the difference that p-tolyl chloroformate was used instead of butyl chloroformate.

Yield: 40 mg MS (ES+): m/e=634.

Example 149

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid methyl ester The title compound was prepared by adapting the procedures described in example 147 with the difference that methyl chloroformate was used instead of butyl chloroformate.

Yield: 22 mg MS (ES+): m/e=558.

Example 150

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid propyl ester The title compound was prepared by adapting the procedures described in example 147 with the difference that propyl chloroformate was used instead of butyl chloroformate.

Yield: 50 mg MS (ES+): m/e=586.

Example 151

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid isopropyl ester The title compound was prepared by adapting the procedures described in example 147 with the difference that isopropyl chloroformate was used instead of butyl chloroformate.

Yield: 50 mg MS (ES+): m/e=586.

Example 152

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 2,2-dimethyl-propyl ester The title compound was prepared by adapting the procedures described in example 147 with the difference that neopentyl chloroformate was used instead of butyl chloroformate.

Yield: 34 mg MS (ES+): m/e=614.

Example 153

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 4-fluorophenyl ester The title compound was prepared by adapting the procedures described in example 147 with the difference that 4-fluorophenyl chloroformate was used instead of butyl chloroformate. Yield: 59 mg MS (ES+): m/e=638.

Example 154

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid phenyl ester The title compound was prepared by adapting the procedures described in example 147 with the difference that phenyl chloroformate was used instead of butyl chloroformate.

Yield: 42 mg MS (ES+): m/e=620.

Example 155

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 3,3,3-trifluoropropyl ester To a solution of 19 μl 3,3,3-trifluoropropan-1-ol and 14 mg triphosgene in 2 ml DCM were slowly added 19 μl triethylamine at 0° C. After 2 h additional 18 μl triethylamine and a solution of 58 mg (S)-4-{[5-(3,3-dimethyl-2-oxo-butoxy)-1-phenyl-1H-pyrazole-3-carbonyl]-amino}-5-oxo-5-piperazin-1-yl-pentanoic acid tert-butyl ester in 100 μl DCM were added at 0° C. The suspension was allowed to warm to RT over a period of 12 h. It was diluted with DCM, 3 equivalents of aqueous NaOH (0.1 M) were added and after 10 minutes the mixture was extracted with 1 M HCl. The product obtained after evaporation of the solvent was treated with TFA in DCM. After stirring for 24 h the solvents were evaporated and the residue was purified by preparative HPLC (C18 reverse phase column, elution with a water/MeCN gradient with 0.1% TFA). The product was obtained as its trifluoroacetate salt.

Yield: 14 mg MS (ES+): m/e=640.

Example 156

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 3-methylsulfanyl-propyl ester The title compound was prepared by adapting the procedures described in example 155 with the difference that 3-(methylthio)-1-propanol was used instead of 3,3,3-trifluoropropan-1-ol. Yield: 13 mg MS (ES+): m/e=632.

Example 157

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid cyclopropylmethyl ester The title compound was prepared by adapting the procedures described in example 155 with the difference that cyclopropylcarbinol was used instead of 3,3,3-trifluoropropan-1-ol.

Yield: 12 mg MS (ES+): m/e=598.

Example 158

4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid cyclobutyl ester The title compound was prepared by adapting the procedures described in example 155 with the difference that cyclobutanol was used instead of 3,3,3-trifluoropropan-1-ol.
Yield: 16 mg MS (ES+): m/e=598.

Example 159

4-((S)-4-Carboxy-2-{[5-(3-methylsulfanyl-propoxy)-1-phenyl-1H-pyrazole-3-carbonyl]-amino}-butyryl)-piperazine-1-carboxylic acid ethyl ester To a solution of 120 mg 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 6 ml DMF were added 38 mg 1-bromo-3-methylsulfanyl-propane (prepared by standard procedure using 3-(methylthio)-1-propanol and phosphorous tribromide) and 74 mg cesium carbonate. After stirring at RT for 12 h it was acidified with 1 M HCl, diluted with ethyl acetate and extracted with aqueous LiCl (4% w/w). The product obtained after evaporation of the solvent was treated with TFA in DCM. After stirring for 24 h the solvents were evaporated and the residue was purified by preparative HPLC (C18 reverse phase column, elution with a water/MeCN gradient with 0.1% TFA). The product was obtained as its trifluoroacetate salt.

Yield: 100 mg MS (ES+): m/e=562.

Example 160

4-((S)-4-Carboxy-2-{[1-phenyl-5-(3,3,3-trifluoropropoxy)-1H-pyrazole-3-carbonyl]-amino}-butyryl)-piperazine-1-carboxylic acid ethyl ester The title compound was prepared by adapting the procedures described in example 159 with the difference that 1-bromo-3,3,3-trifluoropropane was used instead of 1-bromo-3-methylsulfanyl-propane. Yield: 11 mg MS (ES+): m/e=570.

Example 161

4-((S)-4-Carboxy-2-{[1-phenyl-5-(2,2,2-trifluoro-ethoxy)-1H-pyrazole-3-carbonyl]-amino}-butyryl)-piperazine-1-carboxylic acid ethyl ester The title compound was prepared by adapting the procedures described in example 159 with the difference that 1-bromo-3,3,3-trifluoroethane was used instead of 1-bromo-3-methylsulfanyl-propane. Yield: 9 mg MS (ES+): m/e=556.

Example 162

4-((S)-4-Carboxy-2-{[1-phenyl-5-(3,3,3-trifluoro-butoxy)-1H-pyrazole-3-carbonyl]-amino}-butyryl)-piperazine-1-carboxylic acid ethyl ester The title compound was prepared by adapting the procedures described in example 159 with the difference that 1-bromo-3,3,3-trifluorobutane was used instead of 1-bromo-3-methylsulfanyl-propane. Yield: 20 mg MS (ES+): m/e=584.

Example 163

4-((S)-3-Carboxy-2-{[5-(3,3-dimethyl-2-oxo-butoxy)-1-phenyl-1H-pyrazole-3-carbonyl]-amino}-propionyl)-piperazine-1-carboxylic acid ethyl ester (i) 4-((S)-2-Benzyloxycarbonylamino-3-tert-butoxycarbonyl-propionyl)-piperazine-1-carboxylic acid ethyl ester To a solution of 15.4 g (S)-2-Benzyloxycarbonylamino-succinic acid 4-tert-butyl ester, 24.4 ml NEM and 15.6 g TOTU in 80 ml DMF 7.5 g piperazine-1-carboxylic acid ethyl ester were added at RT and stirred for 16 h. The reaction mixture was then diluted with ethyl acetate and washed with aqueous LiCl (4 w/w) and saturated aqueous sodium hydrogen carbonate. The organic phase was dried over MgSO$_4$ and the solvents were removed under reduced pressure. The crude product was used in the subsequent reaction. Yield: 23.0 g.

(ii) 4-((S)-2-Amino-3-tert-butoxycarbonyl-propionyl)-piperazine-1-carboxylic acid ethyl ester To a solution of 23.0 g 4-((S)-2-Benzyloxycarbonylamino-3-tert-butoxycarbonyl-propionyl)-piperazine-1-carboxylic acid ethyl ester in 90 ml ethanol and after purging with argon 2 g Pd/C (10%) were added and the mixture stirred under a hydrogen atmosphere (3 bar) for 16 h. Then the reaction mixture was filtered through a pad of Celite®, washed and the solvents were removed under reduced pressure. After drying under reduced pressure the product was used in the subsequent reaction.
Yield: 16.0 g.

(iii) 4-((S)-3-Carboxy-2-{[5-(3,3-dimethyl-2-oxo-butoxy)-1-phenyl-1H-pyrazole-3-carbonyl]-amino}-propionyl)-piperazine-1-carboxylic acid ethyl ester To a solution of 0.91 g 5-(3,3-dimethyl-2-oxo-butoxy)-1-phenyl-1H-pyrazole-3-carboxylic acid in 40 ml were added 0.51 g HOBt, 0.64 g EDC, 1.7 ml triethylamine and 1.09 g 4-((S)-2-amino-3-tert-butoxycarbonyl-propionyl)-piperazine-1-carboxylic acid ethyl ester. After stirring at RT for 16 h it was diluted with ethyl acetate and subsequently extracted with aqueous LiCl (4% w/w), 0.1 M HCl and aqueous NaHCO$_3$. The organic layer was dried over MgSO$_4$ and the solvent was removed under reduced pressure. The crude product was dissolved in 12 ml DCM and treated with 2 ml TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt. Yield: 0.74 g MS (ES+): m/e=558.

Example 164

4-((S)-2-{[5-(3,3-Dimethyl-2-oxo-butoxy)-1-phenyl-1H-pyrazole-3-carbonyl]-amino}-4-methanesulfonylamino-4-oxo-butyryl)-piperazine-1-carboxylic acid ethyl ester To a solution of 25 mg 4-((S)-3-Carboxy-2-{[5-(3,3-dimethyl-2-oxo-butoxy)-1-phenyl-1H-pyrazole-3-carbonyl]-amino}-propionyl)-piperazine-1-carboxylic acid ethyl ester in 1 ml DMF were added 16 µl DIPEA, 18 mg HATU and 5 mg methanesulfonamide. After stirring at RT for 24 h the solvent was evaporated and the crude product purified by preparative HPLC (C18 reverse phase column, elution with a water/MeCN gradient with 0.1% TFA). The product was obtained as its trifluoroacetate salt. Yield: 2 mg
MS (ES+): m/e=635.

Example 165

4-[(S)-4-Carboxy-2-({5-[(1-cyclopropylcarbamoyl-cyclobutylcarbamoyl)-methoxy]-1-phenyl-1H-pyrazole-3-carbonyl}-amino)-butyryl]-piperazine-1-carboxylic acid ethyl ester i) 1-tert-Butoxycarbonylamino-cyclobutanecarboxylic acid benzyl ester To a solution of 2.0 g N-Boc-1-aminocyclobutane carboxylic acid in 100 ml dichloromethane were added 2.1 g EDC, 1.4 g DMAP, 2.2 ml pyridine and 4.8 ml benzyl alcohol. After stirring for 16 h the mixture was diluted with dichloromethane and washed with 0.1 M HCl and saturated aqueous NaHCO$_3$. The crude product obtained after evaporation of the solvent was purified by chromatography on silica using heptane/ethyl acetate 2/1 as eluent.
Yield: 2.2 g ii) 1-Amino-cyclobutanecarboxylic acid benzyl ester To a solution of 2.2 g 1-tert-Butoxycarbonylamino-cyclobutanecarboxylic acid benzyl ester in 20 ml dichloromethane were added 8 ml TFA. After stirring for 4 h the mixture was concentrated and the residue codistilled with toluene. The free amine was obtained by treatment with (Polystyrylmethyl)trimethylammonium bicarbonate in MeCN. Yield: 1.7 g iii) 4-[(S)-2-({5-[(1-Benzyloxycarbonyl-cyclobutyl-carbamoyl)-methoxy]-1-phenyl-1H-pyrazole-3-carbonyl}-amino)-4-tert-butoxycarbonyl-butyryl]-piperazine-1-carboxylic acid ethyl ester To a solution of 4.9 g 4-{(S)-4-tert-butoxycarbonyl-2-[(5-carboxymethoxy-1-phenyl-1H-pyrazole-3-carbonyl)- amino]-butyryl}-piperazine-1-carboxylic acid ethyl ester in 35 ml DMF were added 1.3 g HOBt, 1.6 g EDC, 2.7 ml DIPEA and 1.7 g 1-Amino-cyclobutanecarboxylic acid benzyl ester. After 12 h the mixture was diluted with ethyl acetate and subsequently extracted with aqueous LiCl (4% w/w), 0.1 M HCl and saturated aqueous NaHCO$_3$. The organic layer was dried over MgSO$_4$ and the solvent was removed under reduced pressure. The crude product thus obtained was used in the subsequent reaction. Yield: 4.7 g iv) 4-[(S)-4-tert-Butoxycarbonyl-2-({5-[(1-carboxy-cyclobutylcarbamoyl)-methoxy]-1-phenyl-1H-pyrazole-3-carbonyl}-amino)-butyryl]-piperazine-1-carboxylic acid ethyl ester To a solution of 4.7 g 4-[(S)-2-({5-[(1-Benzyloxycarbonyl-cyclobutylcarbamoyl)-methoxy]-1-phenyl-1H-pyrazole-3-carbonyl}-amino)-4-tert-butoxycarbonyl-butyryl]-piperazine-1-carboxylic acid ethyl ester in 100 ml ethyl acetate were added under argon 0.5 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 3.7 g v) 4-[(S)-4-Carboxy-2-({5-[(1-cyclopropylcarbamoyl-cyclobutylcarbamoyl)-methoxy]-1-phenyl-1H-pyrazole-3-carbonyl]-amino)-butyryl}-piperazine-1-carboxylic acid ethyl ester To a solution of 100 mg 4-[(S)-4-Carboxy-2-({5-[(1-carboxy-cyclobutylcarbamoyl)-methoxy]-1-phenyl-1H-pyrazole-3-carbonyl}-amino)-butyryl]-piperazine-1-carboxylic acid ethyl ester in 5 ml DMF were added 36 µl DIPEA and 55 mg HATU. After 20 minutes 10 µl cyclopropylamine were added and the reaction mixture was stirred for 12 h. The solvent was removed under reduced pressure and the residue thus obtained redissolved in 2 ml dichloromethane and 320 µl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt. Yield: 65 mg MS (ES+): m/e=668.

Example 166

4-{(S)-4-Carboxy-2-[(5-{[1-(cyclopropylmethyl-carbamoyl)-cyclobutylcarbamoyl]-methoxy}-1-phenyl-1H-pyrazole-3-carbonyl)-amino]-butyryl}-piperazine-1-carboxylic acid ethyl ester The title compound was prepared by adapting the procedures described in example 165 with the difference that aminomethylcyclopropane was used instead of cyclopropylamine.
Yield: 66 mg MS (ES+): m/e=682.

Example 167

4-{(S)-4-Carboxy-2-[(5-{[1-(cyclobutyl-carbamoyl)-cyclobutylcarbamoyl]-methoxy}-1-phenyl-1H-pyrazole-3-carbonyl)-amino]-butyryl}-piperazine-1-carboxylic acid ethyl ester The title compound was prepared by adapting the procedures described in example 165 with the difference that cyclobutylamine was used instead of cyclopropylamine.
Yield: 58 mg MS (ES+): m/e=682.

Example 168

4-{(S)-4-Carboxy-2-[(5-{[1-(2-fluoro-ethylcarbamoyl)-cyclobutylcarbamoyl]-methoxy}-1-phenyl-1H-pyrazole-3-carbonyl)-amino]-butyryl}-piperazine-1-carboxylic acid ethyl ester The title compound was prepared by adapting the procedures described in example 165 with the difference that 2-fluoroethylamine hydrochloride was used instead of cyclopropylamine. Yield: 60 mg MS (ES+): m/e=674.

Example 169

4-[(S)-4-Carboxy-2-({5-[(1-cyclopentylcarbamoyl-cyclobutylcarbamoyl)-methoxy]-1-phenyl-1H-pyrazole-3-carbonyl}-amino)-butyryl]-piperazine-1-carboxylic acid ethyl ester The title compound was prepared by adapting the procedures described in example 165 with the difference that cyclopentylamine was used instead of cyclopropylamine.
Yield: 62 mg MS (ES+): m/e=696.

Example 170

4-{(S)-4-Carboxy-2-[(5-{[1-(cyclobutyl-methyl-carbamoyl)-cyclobutylcarbamoyl]-methoxy}-1-phenyl-1H-pyrazole-3-carbonyl)-amino]-butyryl}-piperazine-1-carboxylic acid ethyl ester The title compound was prepared by adapting the procedures described in example 165 with the difference that N-methyl-N-cyclobutylamine was used instead of cyclopropylamine.
Yield: 45 mg MS (ES+): m/e=695.
Pharmacological Testing The ability of the compounds of the formula I to inhibit the P2Y12 receptor can be assessed by determining the concentration of the compound of the formula I that binds to the human P2Y12 Recombinant Cell Membrane Binding Assay with 33P 2MeS-ADP.
Human P2Y12 Recombinant Cell Membrane Binding Assay The ability of a test compound to bind to the P2Y12 receptor was evaluated in a recombinant cell membrane binding assay. In this competitive binding assay, the test compound competed against a radiolabeled agonist for binding to the P2Y12 receptor, expressed on the cell membrane. Inhibition of binding of the labeled material was measured and correlated to the amount and potency of the test compound. This binding assay is a modification of the procedure described by Takasaki, J. et. al, Mol. Pharmacol., 2001, Vol. 60, pg. 432.

As source of P2Y12, a membrane preparation was prepared from Chinese Hamster Ovary (CHO) cells with recombinant expression of the human P2Y12 receptor according to standard procedures.

To a 96-well microtiterplate the following were added: a) 24 µl of assay buffer (10 mM HEPES, 138 mM NaCl, 2.9 mN KCl, 12 mM NaHCO$_3$, 1 mM EDTA-Na, 0.1% BSA, pH 7.4) b) 1 µL compound in DMSO c) 50 µL P2Y12 CHO membrane (20 µg/ml) and after 15 min at RT d) 25 µL of 1.61 nM 33P 2MeS-ADP (Perkin Elmer NEN custom synthesis, specific activity ~2100Ci/mmol) made in assay buffer.

After 20 min incubation at RT samples were transferred to 96-well microtiter filterplates (Millipore HTS GF/B), prewetted for 20 min with 300 μL of stop buffer (10 mM HEPES, 138 mM NaCl pH 7.4) and then filtered through completely with a Millipore plate vacuum. Next, wells were washed four times with 400 μl/well of stop buffer on a plate vacuum. The plate was disassembled and allowed to air dry overnight with the filter side up overnight. The filter plates were snapped into adapter plates and 0.1 mL of Microscint 20 Scintillation Fluid (Perkin Elmer #6013621) was added to each well. The top of the filterplate was sealed with plastic plate covers. The sealed filterplate were incubated 2 hours at RT. A Microbeta Scintillation Counter was used to measure counts. The binding of compound is expressed as a % inhibition of specific binding, defined by subtraction of the background with 1 mM ADP.

Compounds were diluted as 10 mM DMSO stocks and tested in a four-point, five-fold dilution series run in triplicate beginning at 10 μM, final concentration. Data were analyzed using a four-parameter curve fit with a fixed minimum and maximum experimentally defined as the average positive and negative controls on each plate. The $IC_{50}$ data of the above described human P2Y12 recombinant cell membrane binding assay for exemplary compounds of the present invention are shown in table 1.

TABLE 1

| Example | IC50 [mikro M] |
|---------|----------------|
| 7 | 0.601 |
| 61 | 0.379 |
| 105 | 1.4 |
| 120 | 3.5 |
| 127 | 2.8 |
| 134 | 0.501 |
| 136 | 3.5 |
| 147 | 0.095 |
| 158 | 0.266 |
| 163 | 0.20 |
| 164 | 1.6 |

Inhibition of Human Platelet Aggregation

Alternatively to a binding assay which measures a compound's ability to bind to the P2Y12 receptor, the effect on cellular function was also determined. This ability of the compound was evaluated in two platelet aggregation assays: in 96-well plates and with the "Born"-method using single cuvettes.

96-Well Assay:

Whole blood was collected from healthy volunteers using 20 ml syringes containing 2 ml of ACD-A Aqua-Citrat-Dextrose-A, Fresenius). The anticoagulated whole blood was transferred into 15 ml polypropylene conical tubes (10 ml per tube). The tubes were centrifuged for 15 minutes at 150×g at RT without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in 96-well plates using a microtiter plate reader (SpectraMax Plus 384 with SoftMax Pro software from Molecular Devices). In the plate 15 μl of test compound at 10× final concentration in NaCl is mixed with 120 μl fresh PRP and incubated for 5 minutes. Following that incubation period, 15 μl of 40 μM ADP is added to the reaction mix. This addition of ADP is sufficient to induce aggregation in the absence of an inhibitor. The plates are then transferred to the microplate reader and aggregation is measured over 20 minutes. The instrument settings include: Absorbance at 650 nm, run time 20 minutes with readings in 1-minute intervals and 50 seconds shaking between readings all performed at 37° C. Results of the assay are expressed as % inhibition, and are calculated using area under curve (AUC) of the absorbance over 20 minutes.

The $IC_{50}$ data of the above described platelet aggregation 96-well assay using human platelet rich plasma for exemplary compounds of the present invention are shown in table 2.

TABLE 2

| Example | IC50 [mikro M] |
|---------|----------------|
| 96 | 2.6 |
| 138 | 1.48 |
| 139 | 1.85 |
| 167 | 2.19 |

"Born"-Method:

Whole blood was collected from healthy volunteers using 20 ml syringes containing 2 ml of buffered Citrate. The anticoagulated whole blood was transferred into 15 ml polypropylene conical tubes (10 ml per tube). The tubes were centrifuged for 15 minutes at 340×g at RT without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in single use cuvettes using the platelet aggregation profiler (PAP-4 or -8, Bio/Data corporation).

In the assay cuvette 4 μl of test compound at 100× final concentration in DMSO is mixed with 392 μl fresh PRP and incubated for 2 minutes at 37° C. with 1.200 rpm stirring. Following that incubation period, 4 μl of 250 μM ADP is added to the reaction mix. This addition of ADP is sufficient to induce aggregation in the absence of an inhibitor. After that aggregation is measured over 6 minutes at 37° C. with 1.200 rpm stirring. Results of the assay are expressed as % inhibition, and are calculated using maximum aggregation (Tmax) or area under curve (AUC) of the absorbance over 6 minutes.

The $IC_{50}$ data of the above described platelet aggregation assay using human platelet rich plasma for exemplary compounds of the present invention are shown in table 3.

TABLE 3

| Example | IC$_{50}$ [mikro M] |
|---|---|
| 1 | 2.93 |
| 5 | 2.48 |
| 80 | 2.46 |

What is claimed is:
1. A compound of formula I,

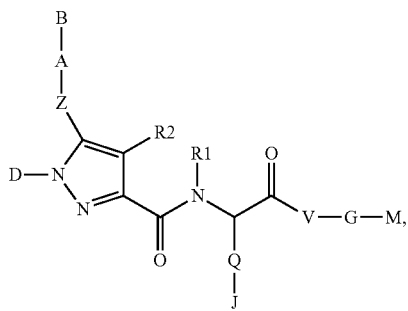

wherein
D is selected from phenyl, naphthyl, and thiazolyl, wherein said phenyl or naphthyl residue is unsubstituted or substituted 1, 2, 3 or 4 times by R4,
Q is 1) -(C$_0$-C$_4$)-alkylene-C(O)—O—(C$_0$-C$_4$)-alkylene-, wherein alkylene is unsubstituted or mono-, di- or trisubstituted independently of one another by R13,
J is 1) hydrogen atom,
Z is 1) —(C$_0$-C$_4$)-alkylene-O—(C$_0$-C$_4$)-alkylene-,
2) —(C$_0$-C$_4$)-alkylene-O—(C$_0$-C$_4$)-alkylene-C(O)—(C$_0$-C$_4$)-alkylene-, or
3) —(C$_0$-C$_4$)-alkylene-O—(C$_0$-C$_4$)-alkylene-C(O)—N(R10)-(C$_0$-C$_4$)-alkylene-,
A is 1) a covalent bond,
2) —(C$_1$-C$_8$)-alkylene-,
3) —(C$_2$-C$_{10}$)-alkenylene-, or
4) —(C$_3$-C$_8$)-cycloalkylene-,
B is
6) —(C$_0$-C$_4$)-alkylene-C(O)—(C$_1$-C$_4$)-alkyl,
7) —(C$_0$-C$_4$)-alkylene-C(O)—O—(C$_1$-C$_4$)-alkyl,
8) —(C$_0$-C$_4$)-alkylene-C(O)—N(R10)-(C$_1$-C$_4$)-alkyl,
and
each of B is further unsubstituted or mono-, di- or trisubstituted independently of one another by R3,
V is piperazinyl,
G is 1) a covalent bond,
2) —(C$_0$-C$_4$)-alkylene-C(O)—(C$_0$-C$_4$)-alkylene-,
3) —(C$_0$-C$_4$)-alkylene-C(O)—O—(C$_0$-C$_4$)-alkylene-, or
4) —(C$_0$-C$_4$)-alkylene-S—(C$_0$-C$_4$)-alkylene-,
M is 1) a hydrogen atom,
2) —(C$_1$-C$_8$)-alkyl, wherein alkyl is unsubstituted or mono-, di- or trisubstituted independently of one another by R14,
3) —C(O)—O—R12,
4) —(C$_3$-C$_8$)-cycloalkyl, wherein said cycloalkyl is unsubstituted or mono-, di- or trisubstituted independently of one another by R14,
5) phenyl, wherein phenyl is unsubstituted or mono-, di- or trisubstituted independently of one another by R14, or
6) heterocyclyl selected from benzoisoxazolyl, furanyl, isoxazolyl, pyridyl, pyrimidinyl, pyrrolidinyl, tetrahydrofuranyl, thiadiazolyl or thiazolyl, wherein heterocyclyl is unsubstituted or substituted by R14,
R1 is hydrogen atom,
R2 is hydrogen atom,
R3 is 1) hydrogen atom,
2) halogen,
3) —(C$_1$-C$_6$)-alkyl, wherein alkyl is unsubstituted or mono-, di- or trisubstituted independently of one another by R13,
4) —(C$_0$-C$_4$)-alkylene-O—R19, wherein R19 is
a) hydrogen atom,
b) —(C$_1$-C$_4$)-alkyl, wherein alkyl is unsubstituted or mono-, di- or trisubstituted independently of one another by R13,
c) —(C$_3$-C$_8$)-cycloalkyl, wherein alkyl is unsubstituted or mono-, di- or trisubstituted independently of one another by R13,
d) —CF$_3$, or
e) —CHF$_2$, or
5) —(C$_0$-C$_4$)-alkylene-C(O)—O—R11,
R4 is 1) hydrogen atom,
2) —(C$_0$-C$_6$)-alkyl, wherein alkyl is unsubstituted or mono-, di- or trisubstituted independently of one another by R13,
3) —(C$_0$-C$_4$)-alkylene-O—R10,
4) halogen,
5) —(C$_1$-C$_3$)-fluoroalkyl,
6) —CN,
7) —NO$_2$,
8) —S—CH$_3$, or
9) —SO$_2$—NH$_2$,
R10 is hydrogen atom, —(C$_1$-C$_4$)-alkyl or —(C$_1$-C$_3$)-fluoroalkyl,
R11 and R12 are independently of one another identical or different and are
1) hydrogen atom,
2) —(C$_1$-C$_6$)-alkyl, wherein alkyl is unsubstituted or mono-, di- or trisubstituted independently of one another by R13,
3) —(C$_1$-C$_3$)-fluoroalkyl, or
4) —(C$_0$-C$_6$)-alkylene-(C$_3$-C$_8$)-cycloalkyl, wherein alkylene and cycloalkyl independently from one another are unsubstituted or mono-, di- or trisubstituted independently of one another by R13,
R13 is hydrogen atom, —(C$_1$-C$_8$)-alkyl, —(C$_3$-C$_8$)-cycloalkyl, —(C$_1$-C$_8$)-alkoxy, halogen, —C(O)—O—R10, —C(O)—N(R10)-R20, or —(C$_1$-C$_3$)-fluoroalkyl,
R14 is hydrogen atom, halogen, —OH, =O, —NO$_2$, —CN, —NH$_2$, —S—R18, —(C$_1$-C$_8$)-alkyl, —(C$_1$-C$_4$)-alkoxy, —C(O)—O—(C$_1$-C$_4$)-alkyl, —(C$_1$-C$_4$)-alkylene-C(O)—OH, or —(C$_1$-C$_3$)-fluoroalkyl,
wherein R18 is hydrogen atom, —(C$_1$-C$_3$)-fluoroalkyl or —(C$_1$-C$_6$)-alkyl, and
R20 is hydrogen atom, —(C$_1$-C$_4$)-alkyl or —(C$_1$-C$_3$)-fluoroalkyl,
in all its stereoisomeric forms and mixtures thereof in any ratio, and its physiologically tolerable salts.
2. The compound as claimed in claim 1, wherein
Q is 1) —(C$_0$-C$_4$)-alkylene-C(O)—O—(C$_0$-C$_2$)-alkylene-, wherein alkylene is unsubstituted or mono- or disubstituted independently of one another by R13,
Z-A form a residue selected from —O—(C$_1$-C$_8$)-alkylene- or —O—(C$_3$-C$_8$)-cycloalkylene-, wherein said residue is bound via the oxygen atom to pyrazole residue and by the alkylene or cycloalkylene carbon atom to B,
G is 1) a covalent bond,
2) —(C$_0$-C$_4$)-alkylene-C(O)—, 3) —(C₀-C₄)-alkylene-C(O)—O—, or
4) —S—,
M is 1) a hydrogen atom,
2) —(C₁-C₆)-alkyl, wherein alkyl is unsubstituted or mono-, di- or trisubstituted independently of one another by R14,
3) —C(O)—O—R12,
4) —(C₃-C₈)-cycloalkyl, wherein said cycloalkyl is unsubstituted or mono-, di- or trisubstituted independently of one another by R14,
5) phenyl, wherein phenyl is unsubstituted or mono-, di- or trisubstituted independently of one another by R14, or
6) a heterocyclyl selected from benzoisoxazolyl, furanyl, isoxazolyl, pyridyl, pyrimidinyl, pyrrolidinyl, tetrahydrofuranyl, thiadiazolyl or thiazolyl, wherein heterocyclyl is unsubstituted or substituted by R14,
R3 is 1) hydrogen atom,
2) halogen,
3) —(C₁-C₆)-alkyl, wherein alkyl is unsubstituted or mono-, di- or trisubstituted independently of one another by R13,
4) —(C₀-C₄)-alkylene-O—R19, wherein R19 is hydrogen atom or —(C₁-C₄)-alkyl, wherein alkyl is unsubstituted or mono-, di- or trisubstituted independently of one another by R13, or
5) —(C₀-C₄)-alkylene-C(O)—O—R11,
R11 and R12 are independently of one another identical or different and are
1) hydrogen atom,
2) —(C₁-C₆)-alkyl, wherein alkyl is unsubstituted or mono-, di- or trisubstituted independently of one another by R13,
3) —(C₁-C₃)-fluoroalkyl, or
4) —(C₀-C₆)-alkylene-(C₃-C₈)-cycloalkyl, wherein alkylene and cycloalkyl independently from one another are unsubstituted or mono-, di- or trisubstituted independently of one another by R13,
R13 is hydrogen atom, —(C₁-C₈)-alkyl, —(C₃-C₈)-cycloalkyl, —(C₁-C₈)-alkoxy, halogen, —C(O)—O—R10, —C(O)—N(R10)-R20, or —(C₁-C₃)-fluoroalkyl,
R14 is hydrogen atom, halogen, —OH, =O, —NO₂, —CN, —NH₂, —S—R18, —(C₁-C₈)-alkyl, —(C₁-C₄)-alkoxy, —C(O)—O—(C₁-C₄)-alkyl, —(C₁-C₄)-alkylene-C(O)—OH, or —(C₁-C₃)-fluoroalkyl,
wherein R18 is hydrogen atom, —(C₁-C₃)-fluoroalkyl or —(C₁-C₆)-alkyl, and
R20 is hydrogen atom or —(C₁-C₄)-alkyl,
in all its stereoisomeric forms and mixtures thereof in any ratio, and its physiologically tolerable salts.

3. A compound selected from:
4-((S)-4-Carboxy-2-{[5-(1-ethoxycarbonyl-cyclobutoxy)-1-phenyl-1H-pyrazole-3-carbonyl]-amino}-butyryl)-piperazine-1-carboxylic acid ethyl ester,
4-((S)-4-Carboxy-2-{[5-(1-ethoxycarbonyl-1-methyl-ethoxy)-1-phenyl-1H-pyrazole-3-carbonyl]-amino}-butyryl)-piperazine-1-carboxylic acid ethyl ester,
4-{(S)-4-Carboxy-2-[(5-ethoxycarbonylmethoxy-1-phenyl-1H-pyrazole-3-carbonyl)-amino]-butyryl}-piperazine-1-carboxylic acid ethyl ester,
4-((S)-4-Carboxy-2-{[5-(2-ethoxycarbonyl-ethoxy)-1-phenyl-1H-pyrazole-3-carbonyl]-amino}-butyryl)-piperazine-1-carboxylic acid ethyl ester,
4-((S)-4-Carboxy-2-{[5-(1-carboxy-cyclobutoxy)-1-phenyl-1H-pyrazole-3-carbonyl]-amino}-butyryl)-piperazine-1-carboxylic acid ethyl ester,
2-{5-[(S)-3-Carboxy-1-(4-ethoxycarbonyl-piperazine-1-carbonyl)-propylcarbamoyl]-2-phenyl-2H-pyrazol-3-yloxy}-malonic acid diethyl ester,
4-((S)-4-Carboxy-2-{[5-(1-carboxy-ethoxy)-1-phenyl-1H-pyrazole-3-carbonyl]-amino}-butyryl)-piperazine-1-carboxylic acid ethyl ester,
4-{(S)-4-Carboxy-2-[(5-carboxymethoxy-1-phenyl-1H-pyrazole-3-carbonyl)-amino]-butyryl}-piperazine-1-carboxylic acid ethyl ester,
4-((S)-4-Carboxy-2-{[5-(1-ethoxycarbonyl-cyclobutoxy)-1-(3-methoxy-phenyl)-1H-pyrazole-3-carbonyl]-amino}-butyryl)-piperazine-1-carboxylic acid ethyl ester,
4-((S)-4-Carboxy-2-{[1-(2,5-dimethyl-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(4-trifluoromethoxy-phenyl)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-m-tolyl-1H-pyrazole-3-carbonyl]-amino}-butyryl)-piperazine-1-carboxylic acid ethyl ester,
4-((S)-4-Carboxy-2-{[5-ethoxycarbonylmethoxy-1-(3-methoxy-phenyl)-1H-pyrazole-3-carbonyl]-amino}-butyryl)-piperazine-1-carboxylic acid ethyl ester,
4-{(S)-4-Carboxy-2-[(5-ethoxycarbonylmethoxy-1-m-tolyl-1H-pyrazole-3-carbonyl)-amino]-butyryl}-piperazine-1-carboxylic acid ethyl ester,
4-((S)-4-Carboxy-2-{[1-(3-chloro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[1-(3-chloro-4-methyl-phenyl)-5-ethoxycarbonylmethoxy-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-p-tolyl-1H-pyrazole-3-carbonyl]-amino}-butyryl)-piperazine-1-carboxylic acid ethyl ester,
4-((S)-4-Carboxy-2-{[1-(3-chloro-4-fluoro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[1-(3-chloro-phenyl)-5-ethoxycarbonylmethoxy-1H-pyrazole-3-carbonyl]-amino}-butyryl)-piperazine-1-carboxylic acid ethyl ester,
4-{(S)-4-Carboxy-2-[(5-ethoxycarbonylmethoxy-1-p-tolyl-1H-pyrazole-3-carbonyl)-amino]-butyryl}-piperazine-1-carboxylic acid ethyl ester,
4-((S)-4-Carboxy-2-{[1-(3-cyano-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[1-(3,5-dimethyl-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[1-(3-cyano-phenyl)-5-ethoxycarbonylmethoxy-1H-pyrazole-3-carbonyl]-amino}-butyryl)-piperazine-1-carboxylic acid ethyl ester,
4-((S)-4-Carboxy-2-{[1-(3-chloro-4-methyl-phenyl)-5-(1-ethoxycarbonyl-cyclobutoxy)-1H-pyrazole-3-carbonyl]-amino}-butyryl)-piperazine-1-carboxylic acid ethyl ester, 4-((S)-4-Carboxy-2-{[1-(3,5-dimethyl-phenyl)-5-ethoxy-carbonylmethoxy-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(4-isopropyl-phenyl)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(2-ethyl-phenyl)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(3-trifluoromethyl-phenyl)-1H-pyrazole-3-carbonyl]-amino}-butyryl)-piperazine-1-carboxylic acid ethyl ester,
4-((S)-4-Carboxy-2-{[1-(3-chloro-2-fluoro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-naphthalen-1-yl-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(3-nitro-phenyl)-1H-pyrazole-3-carbonyl]-amino}-butyryl)-piperazine-1-carboxylic acid ethyl ester,
4-((S)-4-Carboxy-2-{[1-(2,3-dimethyl-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[1-(3,4-difluoro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(4-ethyl-phenyl)-1H-pyrazole-3-carbonyl]-amino}-butyryl)-piperazine-1-carboxylic acid ethyl ester,
4-((S)-4-Carboxy-2-{[1-(2-chloro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[1-(2,6-dichloro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[1-(2,4-difluoro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(4-methylsulfanyl-phenyl)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(4-trifluoromethyl-phenyl)-1H-pyrazole-3-carbonyl]-amino}-butyryl)-piperazine-1-carboxylic acid ethyl ester,
4-[(S)-4-Carboxy-2-{[1-(3-chloro-2-methyl-phenyl)-5-(1-ethoxycarbonyl-cyclobutoxy)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-thiazol-2-yl-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(2-fluoro-phenyl)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(4-sulfamoyl-phenyl)-1H-pyrazole-3-carbonyl]-amino}-butyryl)-piperazine-1-carboxylic acid ethyl ester,
4-((S)-4-Carboxy-2-{[5-(3-methoxy-propoxy)-1-phenyl-1H-pyrazole-3-carbonyl]-amino}-butyryl)-piperazine-1-carboxylic acid ethyl ester,
4-((S)-4-Carboxy-2-{[5-(2-ethoxy-ethoxy)-1-phenyl-1H-pyrazole-3-carbonyl]-amino}-butyryl)-piperazine-1-carboxylic acid ethyl ester,
4-{(S)-4-Carboxy-2-[(5-cyclobutoxy-1-phenyl-1H-pyrazole-3-carbonyl)-amino]-butyryl}-piperazine-1-carboxylic acid ethyl ester,
4-((S)-4-Carboxy-2-{[5-(2-hydroxy-2-methoxycarbonyl-propoxy)-1-phenyl-1H-pyrazole-3-carbonyl]-amino}-butyryl)-piperazine-1-carboxylic acid ethyl ester,
4-{(S)-4-Carboxy-2-[(5-cyclopropylmethoxy-1-phenyl-1H-pyrazole-3-carbonyl)-amino]-butyryl}-piperazine-1-carboxylic acid ethyl ester,
4-((S)-4-Carboxy-2-{[5-(4-hydroxy-butoxy)-1-phenyl-1H-pyrazole-3-carbonyl]-amino}-butyryl)-piperazine-1-carboxylic acid ethyl ester,
4-((S)-4-Carboxy-2-{[5-((R)-3-hydroxy-2-methyl-propoxy)-1-phenyl-1H-pyrazole-3-carbonyl]-amino}-butyryl)-piperazine-1-carboxylic acid ethyl ester,
4-((S)-4-Carboxy-2-{[5-(2,2-difluoro-ethoxy)-1-phenyl-1H-pyrazole-3-carbonyl]-amino}-butyryl)-piperazine-1-carboxylic acid ethyl ester,
4-{(S)-2-[(5-Carbamoylmethoxy-1-phenyl-1H-pyrazole-3-carbonyl)-amino]-4-carboxy-butyryl}-piperazine-1-carboxylic acid ethyl ester,
4-((S)-4-Carboxy-2-{[5-(isopropylcarbamoyl-methoxy)-1-phenyl-1H-pyrazole-3-carbonyl]-amino}-butyryl)-piperazine-1-carboxylic acid ethyl ester,
4-{(S)-4-Carboxy-2-[(5-methylcarbamoyl-methoxy-1-phenyl-1H-pyrazole-3-carbonyl)-amino]-butyryl}-piperazine-1-carboxylic acid ethyl ester,
4-{(S)-4-Carboxy-2-[(5-diethylcarbamoylmethoxy-1-phenyl-1H-pyrazole-3-carbonyl)-amino]-butyryl}-piperazine-1-carboxylic acid ethyl ester,
4-{(S)-4-Carboxy-2-[(5-dimethylcarbamoylmethoxy-1-phenyl-1H-pyrazole-3-carbonyl)-amino]-butyryl}-piperazine-1-carboxylic acid ethyl ester,
4-{(S)-4-Carboxy-2-[(5-isopropoxycarbonylmethoxy-1-phenyl-1H-pyrazole-3-carbonyl)-amino]-butyryl}-piperazine-1-carboxylic acid ethyl ester,
2-[(S)-2-{[5-(1-Ethoxycarbonyl-cyclobutoxy)-1-phenyl-1H-pyrazole-3-carbonyl]-amino}-3-(4-ethoxycarbonyl-piperazin-1-yl)-3-oxo-propyl]-malonic acid,
4-((S)-4-Carboxy-2-{5-(1-isopropylcarbamoyl-cyclobutoxy)-1-phenyl-1H-pyrazole-3-carbonyl]-amino}-butyryl)-piperazine-1-carboxylic acid ethyl ester,
4-((S)-4-Carboxy-2-{[5-(1-dimethylcarbamoyl-cyclobutoxy)-1-phenyl-1H-pyrazole-3-carbonyl]-amino}-butyryl)-piperazine-1-carboxylic acid ethyl ester,
4-[(S)-4-Carboxy-2-({5-[1-(cyclopropylmethyl-carbamoyl)-cyclobutoxy]-1-phenyl-1H-pyrazole-3-carbonyl}-amino)-butyryl]-piperazine-1-carboxylic acid ethyl ester,
4-((S)-4-Carboxy-2-{[5-(1-isobutylcarbamoyl-cyclobutoxy)-1-phenyl-1H-pyrazole-3-carbonyl]-amino}-butyryl)-piperazine-1-carboxylic acid ethyl ester, 4-((S)-4-Carboxy-2-{[5-(1-diethylcarbamoyl-cyclobutoxy)-1-phenyl-1H-pyrazole-3-carbonyl]-amino}-butyryl)-piperazine-1-carboxylic acid ethyl ester,
4-[(S)-4-Carboxy-2-({5-[1-(isopropyl-methyl-carbamoyl)-cyclobutoxy]-1-phenyl-1H-pyrazole-3-carbonyl}-amino)-butyryl]-piperazine-1-carboxylic acid ethyl ester,
4-[(S)-4-Carboxy-2-({5-[1-(methyl-propyl-carbamoyl)-cyclobutoxy]-1-phenyl-1H-pyrazole-3-carbonyl]-amino}-butyryl)-piperazine-1-carboxylic acid ethyl ester,
4-((S)-2-{[5-(1-Butylcarbamoyl-cyclobutoxy)-1-phenyl-1H-pyrazole-3-carbonyl]-amino}-4-carboxy-butyryl)-piperazine-1-carboxylic acid ethyl ester,
4-[(S)-2-({5-[(1-(Carbamoylmethyl-carbamoyl)-cyclobutoxy]-1-phenyl-1H-pyrazole-3-carbonyl}-amino)-4-carboxy-butyryl]-piperazine-1-carboxylic acid ethyl ester,
4-((S)-4-Carboxy-2-{[5-ethoxycarbonylmethoxy-1-(3-fluoro-phenyl)-1H-pyrazole-3-carbonyl]-amino}-butyryl)-piperazine-1-carboxylic acid ethyl ester,
4-((S)-4-Carboxy-2-{[5-(1-ethoxycarbonyl-cyclobutoxy)-1-(3-fluoro-phenyl)-1H-pyrazole-3-carbonyl]-amino}-butyryl)-piperazine-1-carboxylic acid ethyl ester,
4-{(S)-4-Carboxy-2-[(5-carboxy-1-phenyl-1H-pyrazole-3-carbonyl)-amino]-butyryl}-piperazine-1-carboxylic acid ethyl ester,
4-((S)-4-Carboxy-2-{[5-(1-ethoxycarbonyl-ethoxy)-1-phenyl-1H-pyrazole-3-carbonyl]-amino}-butyryl)-piperazine-1-carboxylic acid ethyl ester,
4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid ethyl ester,
4-((S)-4-Carboxy-2-{[5-((E)-3-ethoxycarbonyl-allyloxy)-1-phenyl-1H-pyrazole-3-carbonyl]-amino}-butyryl)-piperazine-1-carboxylic acid ethyl ester,
4-((S)-4-Carboxy-2-{[5-(3-ethoxycarbonyl-2-oxo-propoxy)-1-phenyl-1H-pyrazole-3-carbonyl]-amino}-butyryl)-piperazine-1-carboxylic acid ethyl ester,
4-((S)-4-Carboxy-2-{[5-((E)-3-methoxycarbonyl-allyloxy)-1-phenyl-1H-pyrazole-3-carbonyl]-amino}-butyryl)-piperazine-1-carboxylic acid ethyl ester,
4-((S)-4-Carboxy-2-{[1-(2,5-difluoro-phenyl)-5-(1-ethoxycarbonyl-cyclobutoxy)-1H-pyrazole-3-carbonyl]-amino}-butyryl)-piperazine-1-carboxylic acid ethyl ester,
4-((S)-2-{[5-(1-Ethoxycarbonyl-cyclobutoxy)-1-phenyl-1H-pyrazole-3-carbonyl]-amino}-4-methanesulfonyl-butyryl)-piperazine-1-carboxylic acid ethyl ester,
4-((S)-2-{[1-(3-Bromo-phenyl)-5-(1-ethoxycarbonyl-cyclobutoxy)-1H-pyrazole-3-carbonyl]-amino}-4-carboxy-butyryl)-piperazine-1-carboxylic acid ethyl ester,
4-{(S)-4-Carboxy-2-[(5-ethoxycarbonyl-1-phenyl-1H-pyrazole-3-carbonyl)-amino]-butyryl}-piperazine-1-carboxylic acid ethyl ester,
4-{(S)-4-Carboxy-2-[(5-dimethylcarbamoyl-1-phenyl-1H-pyrazole-3-carbonyl)-amino]-butyryl}-piperazine-1-carboxylic acid ethyl ester,
4-{(S)-2-[(5-Carbamoyl-1-phenyl-1H-pyrazole-3-carbonyl)-amino]-4-carboxy-butyryl}-piperazine-1-carboxylic acid ethyl ester,
4-((S)-2-{[5-(1-Carbamoyl-cyclobutoxy)-1-phenyl-1H-pyrazole-3-carbonyl]-amino}-4-carboxy-butyryl)-piperazine-1-carboxylic acid ethyl ester,
4-((S)-5-Carboxy-2-{[5-(1-ethoxycarbonyl-cyclobutoxy)-1-phenyl-1H-pyrazole-3-carbonyl]-amino}-pentanoyl)-piperazine-1-carboxylic acid ethyl ester,
4-((S)-4-Carboxy-2-{[5-(2-oxo-butoxy)-1-phenyl-1H-pyrazole-3-carbonyl]-amino}-butyryl)-piperazine-1-carboxylic acid ethyl ester,
4-((S)-4-Carboxy-2-{[5-(1-methyl-2-oxo-propoxy)-1-phenyl-1H-pyrazole-3-carbonyl]-amino}-butyryl)-piperazine-1-carboxylic acid ethyl ester,
4-((S)-4-Carboxy-2-{[5-(2-cyclopropyl-2-oxo-ethoxy)-1-phenyl-1H-pyrazole-3-carbonyl]-amino}-butyryl)-piperazine-1-carboxylic acid ethyl ester,
4-[(S)-4-Carboxy-2-({5-[2-(1-methyl-cyclopropyl)-2-oxo-ethoxy]-1-phenyl-1H-pyrazole-3-carbonyl}-amino)-butyryl]-piperazine-1-carboxylic acid ethyl ester,
4-((S)-4-Carboxy-2-{[5-(2-cyclobutyl-2-oxo-ethoxy)-1-phenyl-1H-pyrazole-3-carbonyl]-amino}-butyryl)-piperazine-1-carboxylic acid ethyl ester,
(S)-4-{[5-(3,3-Dimethyl-2-oxo-butoxy)-1-phenyl-1H-pyrazole-3-carbonyl]-amino}-5-oxo-5-[4-(2-oxo-2-pyrrolidin-1-yl-ethyl)-piperazin-1-yl]-pentanoic acid,
(S)-5-(4-Benzoyl-piperazin-1-yl)-4-{[5-(3,3-dimethyl-2-oxo-butoxy)-1-phenyl-1H-pyrazole-3-carbonyl]-amino}-5-oxo-pentanoic acid,
(S)-4-{[5-(3,3-Dimethyl-2-oxo-butoxy)-1-phenyl-1H-pyrazole-3-carbonyl]-amino}-5-oxo-5-[4-(4-trifluoromethyl-pyridin-2-yl)-piperazin-1-yl]-pentanoic acid,
4-((S)-2-{[5-(1-Ethoxycarbonyl-cyclobutoxy)-1-phenyl-1H-pyrazole-3-carbonyl]-amino}-4-methoxycarbonyl-butyryl)-piperazine-1-carboxylic acid ethyl ester,
4-((S)-4-Carboxy-2-{[1-phenyl-5-(3,4,4-trifluoro-but-3-enyloxy)-1H-pyrazole-3-carbonyl]-amino}-butyryl)-piperazine-1-carboxylic acid ethyl ester,
4-((S)-4-Carboxy-2-{[5-(1-ethoxycarbonyl-butoxy)-1-phenyl-1H-pyrazole-3-carbonyl]-amino}-butyryl)-piperazine-1-carboxylic acid ethyl ester,
(S)-5-[4-(3,5-Dimethoxy-phenyl)-piperazin-1-yl]-4-{[5-(3,3-dimethyl-2-oxo-butoxy)-1-phenyl-1H-pyrazole-3-carbonyl]-amino}-5-oxo-pentanoic acid,
(S)-4-[(5-Carbamoylmethoxy-1-phenyl-1H-pyrazole-3-carbonyl)-amino]-5-oxo-5-[4-(3-trifluoromethyl-phenyl)-piperazin-1-yl]-pentanoic acid,
(S)-4-[(5-Cyclopropylmethoxy-1-phenyl-1H-pyrazole-3-carbonyl)-amino]-5-oxo-5-[4-(3-trifluoromethyl-phenyl)-piperazin-1-yl]-pentanoic acid,
(S)-4-[(5-Cyclobutyl-methoxy-1-phenyl-1H-pyrazole-3-carbonyl)-amino]-5-oxo-5-[4-(3-trifluoromethyl-phenyl)-piperazin-1-yl]-pentanoic acid,
1-(5-{(S)-3-Carboxy-1-[4-(3-trifluoromethyl-phenyl)-piperazine-1-carbonyl]-propylcarbamoyl}-2-phenyl-2H-pyrazol-3-yloxy)-cyclobutanecarboxylic acid ethyl ester,
4-((S)-2-{[5-(3,3-Dimethyl-2-oxo-butoxy)-1-phenyl-1H-pyrazole-3-carbonyl]-amino}-3-methoxycarbonylamino-propionyl)-piperazine-1-carboxylic acid ethyl ester,
4-[(S)-2-{[5-(3,3-Dimethyl-2-oxo-butoxy)-1-phenyl-1H-pyrazole-3-carbonyl]-amino}-3-(oxalyl-amino)-propionyl]-piperazine-1-carboxylic acid ethyl ester,
4-[(S)-2-{[5-(3,3-Dimethyl-2-oxo-butoxy)-1-phenyl-1H-pyrazole-3-carbonyl]-amino}-3-(2-ethoxy-3,4-dioxo-cyclobut-1-enylamino)-propionyl]-piperazine-1-carboxylic acid ethyl ester, 4-[(S)-2-{[5-(3,3-Dimethyl-2-oxo-butoxy)-1-phenyl-1H-pyrazole-3-carbonyl]-amino}-3-(2-hydroxy-3,4-dioxo-cyclobut-1-enylamino)-propionyl]-piperazine-1-carboxylic acid ethyl ester, 4-[(S)-4-Carboxy-2-({5-[(1-carboxy-1-methyl-ethylcarbamoyl)-methoxy]-1-phenyl-1H-pyrazole-3-carbonyl}-amino)-butyryl]-piperazine-1-carboxylic acid ethyl ester, 4-[(S)-4-Carboxy-2-({5-[((S)-1-carboxy-ethylcarbamoyl)-methoxy]-1-phenyl-1H-pyrazole-3-carbonyl}-amino)-butyryl]-piperazine-1-carboxylic acid ethyl ester, 4-[(S)-4-Carboxy-2-({5-[((R)-1-carboxy-ethylcarbamoyl)-methoxy]-1-phenyl-1H-pyrazole-3-carbonyl]-amino}-butyryl)-piperazine-1-carboxylic acid ethyl ester, 4-[(S)-4-Carboxy-2-({5-[(carboxymethyl-methyl-carbamoyl)-methoxy]-1-phenyl-1H-pyrazole-3-carbonyl]-amino}-butyryl)-piperazine-1-carboxylic acid ethyl ester, 4-{(S)-4-Carboxy-2-[(5-cyclopropylcarbamoylmethoxy-1-phenyl-1H-pyrazole-3-carbonyl)-amino]-butyryl}-piperazine-1-carboxylic acid ethyl ester, 4-[(S)-4-Carboxy-2-({5-[(cyclopropylcarbamoylmethyl-carbamoyl)-methoxy]-1-phenyl-1H-pyrazole-3-carbonyl]-amino}-butyryl)-piperazine-1-carboxylic acid ethyl ester, 4-((S)-4-Carboxy-2-{[5-(1-cyclopropylcarbamoyl-1-methyl-ethoxy)-1-phenyl-1H-pyrazole-3-carbonyl]-amino}-butyryl)-piperazine-1-carboxylic acid ethyl ester, 4-[(S)-4-Carboxy-2-({5-[1-(cyclopropylcarbamoylmethyl-carbamoyl)-1-methyl-ethoxy]-1-phenyl-1H-pyrazole-3-carbonyl}-amino)-butyryl]-piperazine-1-carboxylic acid ethyl ester, 4-((S)-4-Carboxy-2-{[5-(1-cyclopropylcarbamoyl-ethoxy)-1-phenyl-1H-pyrazole-3-carbonyl]-amino}-butyryl)-piperazine-1-carboxylic acid ethyl ester, 4-{(S)-4-Carboxy-2-(5-[1-(cyclopropylcarbamoylmethyl-carbamoyl)-ethoxy]-1-phenyl-1H-pyrazole-3-carbonyl}-amino)-butyryl]-piperazine-1-carboxylic acid ethyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid butyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid p-tolyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid methyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid propyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid isopropyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 2,2-dimethylpropyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 4-fluorophenyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid phenyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 3,3,3-trifluoro-propyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid 3-methylsulfanyl-propyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid cyclopropylmethyl ester, 4-((S)-4-Carboxy-2-{[5-(3,3-dimethyl-2-oxo-butoxy)-1-phenyl-1H-pyrazole-3-carbonyl]-amino}-butyryl)-piperazine-1-carboxylic acid cyclobutyl ester, 4-((S)-4-Carboxy-2-{[5-(3-methylsulfanyl-propoxy)-1-phenyl-1H-pyrazole-3-carbonyl]-amino}-butyryl)-piperazine-1-carboxylic acid ethyl ester, 4-((S)-4-Carboxy-2-{[1-phenyl-5-(3,3,3-trifluoro-propoxy)-1H-pyrazole-3-carbonyl]-amino}-butyryl)-piperazine-1-carboxylic acid ethyl ester, 4-((S)-4-Carboxy-2-{[1-phenyl-5-(2,2,2-trifluoro-ethoxy)-1H-pyrazole-3-carbonyl]-amino}-butyryl)-piperazine-1-carboxylic acid ethyl ester, 4-((S)-4-Carboxy-2-{[1-phenyl-5-(3,3,3-trifluoro-butoxy)-1H-pyrazole-3-carbonyl]-amino}-butyryl)-piperazine-1-carboxylic acid ethyl ester, 4-((S)-3-Carboxy-2-{[5-(3,3-dimethyl-2-oxo-butoxy)-1-phenyl-1H-pyrazole-3-carbonyl]-amino}-propionyl)-piperazine-1-carboxylic acid ethyl ester, 4-((S)-2-{[5-(3,3-Dimethyl-2-oxo-butoxy)-1-phenyl-1H-pyrazole-3-carbonyl]-amino}-4-methane-sulfonylamino-4-oxo-butyryl)-piperazine-1-carboxylic acid ethyl ester, 4-[(S)-4-Carboxy-2-({5-[(1-cyclopropylcarbamoyl-cyclobutylcarbamoyl)-methoxy]-1-phenyl-1H-pyrazole-3-carbonyl]-amino)-butyryl}-piperazine-1-carboxylic acid ethyl ester, 4-{(S)-4-Carboxy-2-[(5-{[1-(cyclopropylmethyl-carbamoyl)-cyclobutylcarbamoyl]-methoxy}-1-phenyl-1H-pyrazole-3-carbonyl)-amino]-butyryl}-piperazine-1-carboxylic acid ethyl ester, 4-{(S)-4-Carboxy-2-[(5-(1-(cyclobutyl-carbamoyl)-cyclobutyl-carbamoyl]-methoxy]-1-phenyl-1H-pyrazole-3-carbonyl)-amino]-butyryl}-piperazine-1-carboxylic acid ethyl ester, 4-{(S)-4-Carboxy-2-[(5-{[1-(2-fluoro-ethylcarbamoyl)-cyclobutylcarbamoyl]-methoxy}-1-phenyl-1H-pyrazole-3-carbonyl)-amino]-butyryl}-piperazine-1-carboxylic acid ethyl ester, 4-[(S)-4-Carboxy-2-({5-[(1-cyclopentyl-carbamoyl-cyclobutylcarbamoyl)-methoxy]-1-phenyl-1H-pyrazole-3-carbonyl)-amino]-butyryl}-piperazine-1-carboxylic acid ethyl ester, and 4-{(S)-4-Carboxy-2-[(5-{[1-(cyclobutyl-methyl-carbamoyl)-cyclobutylcarbamoyl]-methoxy}-1-phenyl-1H-pyrazole-3-carbonyl)-amino]-butyryl}-piperazine-1-carboxylic acid ethyl ester.

4. A process for the preparation of a compound of formula I as claimed in claim 1, which comprises reacting a compound of formula II with $HR^2$ to give a compound of formula I,

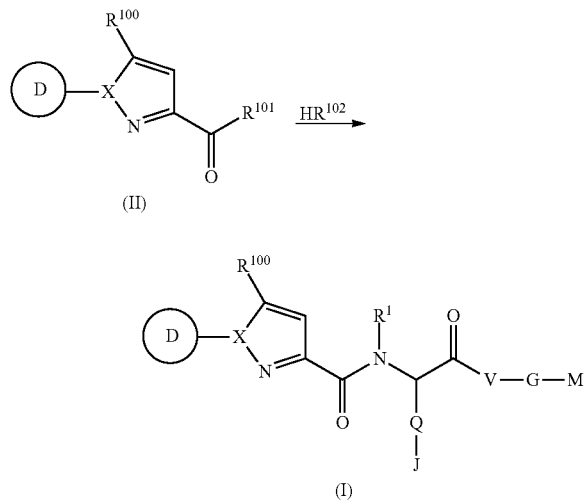

(II)

(I)

wherein X is N, D is as defined in formula I, $R^{101}$ is —OH, $HR^{102}$ is an amine of the formula V, and $R^{100}$ is a residue of formula VI

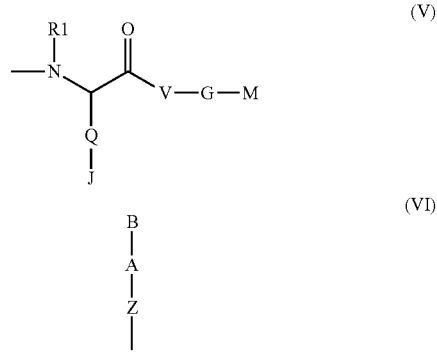

(V)

(VI)

wherein the residues $R^1$, Q, J, V, G, M, Z, A and B are as defined in claim 1.

5. The compound as claimed in claim 1, wherein G is a covalent bond.

6. The compound as claimed in claim 1, wherein M is —C(O)—O—R12.

7. The compound as claimed in claim 1, wherein G is a covalent bond and M is —C(O)—O—R12.

8. A pharmaceutical preparation, comprising at least one compound as claimed in claim 1 in all its stereoisomeric forms and mixtures thereof in any ratio or its physiologically tolerable salts and a pharmaceutically acceptable carrier.

* * * * *